(12) United States Patent
Valle et al.

(10) Patent No.: US 9,447,436 B2
(45) Date of Patent: Sep. 20, 2016

(54) PRODUCTION OF SATURATED FATTY ALCOHOLS FROM ENGINEERED MICROORGANISMS

(71) Applicant: Codexis, Inc., Redwood City, CA (US)

(72) Inventors: Fernando Valle, Burlingame, CA (US); Svetlana Balatskaya, Fremont, CA (US); Yoram Barak, Greenwich, CT (US); Louis Clark, San Francisco, CA (US); Kristian Karlshoej, Naperville, IL (US); Patricia Choudhary, Foster City, CA (US); Catherine Cho, Redwood City, CA (US); Kaman Chan, San Bruno, CA (US); Jonathan Vroom, South San Francisco, CA (US)

(73) Assignee: Codexis, Inc., Redwood City, CA (US)

( * ) Notice: Subject to any disclaimer, the term of this patent is extended or adjusted under 35 U.S.C. 154(b) by 47 days.

(21) Appl. No.: 14/366,517

(22) PCT Filed: Dec. 13, 2012

(86) PCT No.: PCT/US2012/069553
§ 371 (c)(1),
(2) Date: Jun. 18, 2014

(87) PCT Pub. No.: WO2013/096092
PCT Pub. Date: Jun. 27, 2013

(65) Prior Publication Data
US 2014/0336423 A1 Nov. 13, 2014

Related U.S. Application Data

(63) Continuation-in-part of application No. PCT/US2012/069444, filed on Dec. 13, 2012.

(60) Provisional application No. 61/577,756, filed on Dec. 20, 2011, provisional application No. 61/578,673, filed on Dec. 21, 2011, provisional application No. 61/636,044, filed on Apr. 20, 2012, provisional application No. 61/674,053, filed on Jul. 20, 2012.

(51) Int. Cl.
| | |
|---|---|
| C12P 7/04 | (2006.01) |
| C07C 31/125 | (2006.01) |
| A61Q 5/00 | (2006.01) |
| A61Q 19/00 | (2006.01) |
| C12N 9/02 | (2006.01) |
| A61K 8/34 | (2006.01) |

(52) U.S. Cl.
CPC .................. *C12P 7/04* (2013.01); *A61K 8/342* (2013.01); *A61Q 5/00* (2013.01); *A61Q 19/00* (2013.01); *C07C 31/125* (2013.01); *C12N 9/0008* (2013.01); *C12Y 102/0105* (2013.01); *A61K 2800/10* (2013.01); *C12Y 102/01* (2013.01); *C12Y 102/0108* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 4,356,196 | A | 10/1982 | Hultquist |
| 4,461,648 | A | 7/1984 | Foody |
| 4,556,430 | A | 12/1985 | Converse et al. |
| 4,600,590 | A | 7/1986 | Dale |
| 5,037,663 | A | 8/1991 | Dale |
| 5,171,592 | A | 12/1992 | Holtzapple et al. |
| 5,344,771 | A | 9/1994 | Davies et al. |
| 5,512,482 | A | 4/1996 | Voelker et al. |
| 5,723,761 | A | 3/1998 | Voelker et al. |
| 5,910,631 | A | 6/1999 | Topfer et al. |
| 5,939,544 | A | 8/1999 | Karstens et al. |
| 6,106,888 | A | 8/2000 | Dale et al. |
| 6,117,679 | A | 9/2000 | Stemmer |
| 6,143,538 | A | 11/2000 | Somerville et al. |
| 6,150,512 | A | 11/2000 | Yuan |
| 6,176,176 | B1 | 1/2001 | Dale et al. |
| 6,251,674 | B1 | 6/2001 | Tobin et al. |
| 6,309,883 | B1 | 10/2001 | Minshull et al. |
| 6,376,246 | B1 | 4/2002 | Crameri et al. |
| 6,586,182 | B1 | 7/2003 | Patten et al. |
| 7,332,311 | B2 | 2/2008 | Lardizabal et al. |
| 7,465,791 | B1 | 12/2008 | Hallberg et al. |
| 7,754,457 | B2 | 7/2010 | Foody et al. |
| 7,783,428 | B2 | 8/2010 | Gustafsson et al. |
| 7,790,432 | B2 | 9/2010 | Chatterjee et al. |
| 8,110,670 | B2 | 2/2012 | Hu et al. |
| 8,574,878 | B2 | 11/2013 | Behrouzian et al. |
| 2006/0195947 | A1 | 8/2006 | Davis et al. |

(Continued)

FOREIGN PATENT DOCUMENTS

| | | | |
|---|---|---|---|
| DE | EP 2 157 170 | * | 2/2010 |
| EP | 2157170 B1 | | 1/2014 |

(Continued)

OTHER PUBLICATIONS

EPO Proteins Database Accession No. GN095343 dated Apr. 16, 2009.

(Continued)

*Primary Examiner* — Suzanne M Noakes
*Assistant Examiner* — Jae W Lee
(74) *Attorney, Agent, or Firm* — Codexis, Inc.

(57) ABSTRACT

Recombinant bacterial microorganisms are provided which comprise heterologous fatty acyl reductases ("FAR") polypeptides wherein said microorganisms have been engineered to produce increased amounts of saturated fatty alcohols and methods of making saturated fatty alcohols using the recombinant bacterial microorganisms.

12 Claims, 10 Drawing Sheets

(56) References Cited

U.S. PATENT DOCUMENTS

| | | |
|---|---|---|
| 2007/0031953 A1 | 2/2007 | Dunson, Jr. et al. |
| 2008/0104724 A1 | 5/2008 | Sticklen et al. |
| 2008/0220990 A1 | 9/2008 | Fox |
| 2009/0312196 A1 | 12/2009 | Colbeck et al. |
| 2010/0203614 A1 | 8/2010 | Wahlen et al. |
| 2011/0000125 A1 | 1/2011 | McDaniel et al. |
| 2011/0195469 A1 | 8/2011 | Roessler et al. |
| 2011/0229942 A1 | 9/2011 | Campbell et al. |
| 2012/0115195 A1 | 5/2012 | Keasling et al. |
| 2012/0142979 A1 | 6/2012 | Keasling et al. |
| 2012/0184006 A1 | 7/2012 | Willis et al. |

FOREIGN PATENT DOCUMENTS

| | | |
|---|---|---|
| WO | 2007/136762 A2 | 11/2007 |
| WO | 2008/119082 A2 | 10/2008 |
| WO | 2009/045651 A2 | 4/2009 |
| WO | 2010/062480 A2 | 6/2010 |
| WO | 2010/075483 A2 | 7/2010 |
| WO | 2011/008535 A1 | 1/2011 |
| WO | 2011/008565 A1 | 1/2011 |
| WO | 2011/019858 A1 | 2/2011 |
| WO | 2012/006114 A2 | 1/2012 |
| WO | 2013/096082 A1 | 6/2013 |

OTHER PUBLICATIONS

USPTO Proteins Databases Accession No. AFO01933 dated Jul. 23, 2012.

USPTO Proteins Databases Accession No. ABZ47816 dated Feb. 7, 2008.

EPO Proteins Database Accession No. HB413854 dated Jun. 29, 2009.

EPO Proteins Database Accession No. HC499930 dated Apr. 22, 2010.

USPTO Proteins Databases Accession No. ABZ47802 dated Feb. 7, 2008.

Altschul, S., et al., "Basic local alignment search tool," J. Mol. Biol., 215: 403-410 (1990).

Altschul, S.F., et al., "Gapped BLAST and PSI-BLAST: a new generation of protein database search programs," Nucleic Acids Res., 25(17):3389-3402 (1997).

Archer, C.T., et al., "The genome sequence of E. coli W (ATCC 9637): comparative genome analysis and an improved genome-scale reconstruction of E. coli," BMC Genomics, 12:9 [2011].

Baba, T., et al., "Construction of Escherichia coli K-12 in-frame,single-gene knockout mutants: the Keio collection," Mol Syst Biol, 2:1-11 [2006].

Brosius, J., et al., "Spacing of the -10 and -35 Regions in the tac Promoter," J. Biol. Chem., 260(6): 3539-3541 [1985].

Cantu, D.C., et al., "Thioesterases: a new perspective based on their primary and tertiary structures," Protein Science, 19(7):1281-1295 (2010).

Cantu, D.C., et al., "ThYme: a database for thioester-active enzymes," Nucleic Acid Research, 39:D342-D346 (2011).

Carter, P., "Site-directed mutagenesis," Biochem. J., 237:1-7 [1986].

Court, D.L., et al., "Genetic Engineering Using Homologous Recombination," Annual Rev. Genet., 36:361-388 [2002].

Datsenko, K.A., et al., "One-step inactivation of chromosomal genes in Escherichia coli K-12 using PCR products," PNAS, 97(12): 6640-6645 [2000].

Datta, S., et al., "A set of recombineering plasmids for gram-negative bacteria," Gene, 379: 109-115 (2006).

De Boer, H.A., et al., "The tac promoter: A functional hybrid derived from the trp and lac promoters," Proc. Natl Acad. Sci. USA, 80: 21-25 (1983).

Doan, T.T.P., et al., "Functional expression of five Arabidopsis fatty acyl-CoA reductase genes in Escherichia coli," J. Plant Physiol., 166: 787-796 [2009].

Dower, W.J., et al., "High efficiency transformation of E.coli by high voltage electroporation," Nucleic Acids Research, 16(13): 6127-6145 [1988].

Eblen, D.R., et al., "Studies to Select Appropriate Nonpathogenic Surrogate Escherichia coli Strains for Potential Use in Place of Escherichia coli O157:H7 and Salmonella in Pilot Plant Studies," J. of Food Protection, 68(2):282-291 [2005].

Hayashi, K., et al., "Highly accurate genome sequences of Escherichia coli K-12 strains MG1655 and W3110," Mol. Syst. Biol., 2(2006.0007):1-5 [2005].

Heath, R.J., et al., "Enoyl-Acyl Carrier Protein Reductase (fabl) Plays a Determinant Role in Completing Cycles of Fatty Acid Elongation in Escherichia coli," J. Biol. Chem., 270(44): 26538-26542 [1995].

Heath, R.J., et al., "Roles of the FabA and FabZ Beta-Hydroxyacyl-Acyl Carrier Protein Dehydratases in Escherichia coli Fatty Acid Biosynthesis," J. Biol. Chem., 271(44): 27795-27801 [1996].

Henikoff, S., et al., "Amino acid substitution matrices from protein blocks," Proc. Natl. Acad. Sci. USA, 89:10915-10919 [1992].

Hofvander, P., et al., "A prokaryotic acyl-CoA reductase performing reduction of fatty acyl-CoA to fatty alcohol," FEBS Letters, 585(22):3538-3543 (2011).

Ishige, T., et al., "Long-Chain Aldehyde Dehydrogenase That Participates in n-Alkane Utilization and Wax Ester Synthesis in Acinetobacter sp. Strain M-1," Appl. Environ. Microbiol., 66:3481-3486 (2000).

Jones, A., et al., "Palmitoyl-Acyl Carrier Protein (ACP) Thioesterase and the Evolutidnary-Origin of Plant ACyl-ACP Thioesterases," The Plant Cell, 7:359-371 (1995).

Kalscheuer, R., et al., "Neutral Lipid Biosynthesis in Engineered Escherichia coli: Jojoba Oil-Like Wax Esters and Fatty Acid Butyl Esters," Appl. Environ. Microbiol., 72:1373-79 [2006].

Lathe, R., et al., "Plasmid and bacteriophage vectors for excision of intact inserts," Gene, 57:193-201 [1987].

Lerner, C.G., et al., "Low copy number plasmids for regulated low-level expression of cloned genes in Escherichia cofi with blue/white insert screening capability," Nucleic Acids Research, 18(15):4631 [1990].

Li, J.J., et al., "Reductions" in Modern Organic Synthesis in the Laboratory, Oxford University Press, Inc., p. 81-83 [2007].

Ling, M.M., et al., "Approaches to DNA Mutagenesis: An Overview," Anal. Biochem., 254(2):157-78 [1997].

Link, A.J., et al., "Methods for generating precise deletions and insertions in the genome of wild-type Escherichia coli: application to open reading frame characterization," J. Bact., 179: 6228-6237 [1997].

Metz, J.G., et al., "Purification of a Jojoba Embryo Fatty Acyl-Coenzyme A Reductase and Expression of Its cDNA in High Erucic Acid Rapeseed," Plant Physiol., 122:635-644 [2000].

Minshull, J., et al., "Protein evolution by molecular breeding," Curr. Op. Chem. Biol., 3:284-290 [1999].

Morgan-Kiss, R.M., et al., "The Escherichia coli fadK (ydiD) Gene Encodes an Anerobically Regulated Short Chain Acyl-CoA Synthetase," J. Biol. Chem., 279:37324-37333 [2004].

Needleman, S., et al., "A general method applicable to the search for similarities in the amino acid sequence of two proteins," J. Mol. Biol. 48:443-453 (1970).

Nevoigt, E., et al., "Engineering of Promoter Replacement Cassettes for Fine-Tuning of Gene Expression in Saccharomyces cerevisiae," Appl. Environ. Microbiol., 72:5266-5273 (2006).

Notredame, C., et al., "T-COFFEE: A novel method for multiple sequence alignments," JMB, 302:205-217, [2000].

The UniProt Consortium, "The Universal Protein Resource (UniProt) in 2010," Nucleic Acid Res., 38:D142-D148 [2010].

Orosz, A., et al., "Analysis of the complex transcription termination region of the Escherichia coli rrnB gene," Eur. J. Biochem., 201: 653-659 [1991].

Moto, K., et al., "Pheromone gland-specific fatty-acyl reductase of the silkmoth, Bombyx mori," PNAS, 100(16):9156-9161 [2003].

(56) References Cited

OTHER PUBLICATIONS

Reiser, S., et al., "Isolation of mutants of Acinetobacter calcoaceticus deficient in wax ester synthesis and complementation of one mutation with a gene encoding a fatty acyl coenzyme A reductase," J. Bacteriol., 179:2969-2975 (1997).
Sadler, J.R., et al., "A perfectly symmetric lac operator binds the lac repressor very tightly," PNAS, 80: 6785-6789 [1983].
Smith, M., "In Vitro Mutagenesis," Ann. Rev. Genet., 19:423-462 [1985].
Terpe, K., "Overview of bacterial expression systems for heterologousprotein production: from molecular and biochemicalfundamentals to commercial systems," Appl. Microbiol. Biotechnol., 72:211-222 [2006].
Tsujita, T., et al., "Fatty Acid Alcohol Ester-Synthesizing Activity of Lipoprotein Lipase" J. Biochem. 126:1074-1079 [1999].
Villa-Komaroff, L., et al., "A bacterial clone synthesizing proinsulin," Proc. Natl Acad. Sci. USA, 75:3727-3731 (1978).
Voelker, T.A., et al., "Alteration of the specificity and regulation of fatty acid synthesis of *Escherichia coli* by expression of a plant medium-chain acyl-acyl carrier protein thioesterase," J. Bacteriol., 176:7320-7327[1994].
Warrens, A.N., et al., "Splicing by overlap extension by PCR using asymmetric amplification: an improved technique for the generation of hybrid proteins of immunological interest," Gene, 186(1):29-35 [1997].
Weil, J., et al. "Pretreatment of Yellow Poplar Sawdust by Pressure Cooking in Water," Appl. Biochem. Biotechnol., 68(1-2): 21-40 [1997].

* cited by examiner

SEQ ID NO: 1_ Polynucleotide sequence of a codon optimized FAR from *Marinobacter algicola* DG893.

ATGGCTACTCAACTCAACAACAGAACGAACGGTGCATCTGCATCCGGCGTCTTGGAACAACTTCGTGGAAAGCA
CGTTCTTATCACAGGTACTACCCGGATTTTGGGCAAAGTGGTTCTGGAAAAGTTGATTCGTACTGTTC
CGGATATTGGAGGTATTCATCTGCTGATTCGTCTCCCTCCGTCTTGAACGTTGCGTCACGATGATAAACGTCATCCAGCCGCTCGTGAACGTTTC
CTGAACGAAATTGCGTCCTCCCCGTCTTGAACGTTGCGTCACGATGATAAGACGTCGAGAC
CTTCTTGGAAGAACGTGTTCACTGTATTACCCGGTCAGGTTGACGCTTTATTAAACAGCGCTGCAAGCGTGAACTTTCGT
AACGTTTTCGTGCTTTGGCCGGTCAGGTTGACGCTTTATTAAACAGCGCTGCAAGCGTGAACTTTCGT
GAGGAATTGGATAAAGCCCTGAAAATCAACACCCTGTCTCTTGTACGTTAACGGTAAAAAACTCCGGTCAAATTA
GAACTCCGCTATGGCGGTCATTCAGGTTTCCACTGTTACGTTAACGGTAAAAACTCCGGTCAAATTA
CCGAATCCGTCATTAAACCTGCTGGCCAATCCATTCCCCGTTCCACTGACGGTTACTACGAGATCGAA
GAATTGGTCCATCTGTTGCAAGACAAGATTTCCGATGTTAAAGCTCGTTACTCCGGCAAAGTTCTGGA
GAAAAATTGGTTGATTGGGTATTCGTGAGGCCAATAATTACGGATGGTCCTACACATTCA
CCAAATGGTTGGGTGAACAACTGCTGAAGAAGCCTTGCCCGCTGTGGATCGAAGCCTTGTCTCTTGACTATTGTGCGTCCC
TCTATTATTGAGTCCGCTTTGCCCGTGAAAAAGTTAGCCTGTTCCCTGAAAAAACGTTCCGGCATTATTGATG
CATTATCTTGGCTTATGCCCGTGAAAAAGTTAGCCTGTTCCCTGAAAAAACGTTCCGGCATTATTGATG
TTATTCCTCGTGATTTGGTTGCGAACTCCATCATCTTGTCTCTTGGCTGAGGCGTTGTCTGGTTCTGGT
CAACGTCGTATTTATCAATGTTGCAGCGGTGGTTCTAATCAACTGTGTTTATCGTCGTCCTACTAAAC
TTTGATGGCCGAGGCTAAGACCGTAAATTGTTTGACGTTGTGGTATCGTGTTCCTCTTTCTATT
CTTTCGTCGCCCGTGAACCGTAAATTGTTTGACGTTGTGGTATCGTGTTCCTCTTTCTATT
GCCGGTAAAGCTATGCGTTGCGTGGTCAAAATCGTGAGTGAAAGTGCTTAAGAACCTTGATACGAC
CCGTTCCCTTGCAACCATTTTGGCTTCTATACTGCTCCCGACTATATCTTCCGTAACGATAGCTTGA
TGGCCCTGGCTTCTCGTATGGGTGAATTGGATGGTGTCTTTTCCCAGTTACGCTCGTCAAATTGAT
TGGCAGTTGTACTGTGTAAATTCATTGGGTGGTCTGAACCGTTACGCTTTGAAGGAACGTAAACT
GTATTCTTTGCGTGCTGCTGATACTCGTAAAAAAGCTGCCTAA

FIG. 3

SEQ ID NO: 2_ FAR polypeptide sequence encoded by the polynucleotide sequence of SEQ ID NO: 1.

MATQQQNGASASGVLEQLRGKHVLITGTTGFLGKVVLEKLIRTVPDIGGIHLLIRGNKRHPAARERF
LNEIASSSVFERLRHDDNEAFETFLEERVHCITGEVTESRFGLTPERFRALAGQVDAFINSAASVNFR
EELDKALKINTLCLENVAALAELNSAMAVIQVSTCYVNGKNSGQITESVIKPAGESIPRSTDGYYEIE
ELVHLLQDKISDVKARYSGKVLEKKLVDLGIREANNYGWSDTYTFTKWLGEQLLMKALSGRSLTIVRP
SIIESALEEPSPGWIEGVKVADAIILAYAREKVSLFPGKRSGIIDVIPVDLVANSIILSLAEALSGSG
QRRIYQCCSGGSNPISLGKFIDYLMAEAKTNYAAYDQLFYRRPTKPFVAVNRKLFDVVVGGMRVPLSI
AGKAMRLAGQNRELKVLKNLDTTRSLATIFGFYTAPDYIFRNDSLMALASRMGELDRVLFPVDARQID
WQLYLCKIHLGGLNRYALKERKLYSLRAADTRKKAA

SEQ ID NO: 3_ Polynucleotide Sequence of the NcoI-SalI DNA fragment coding the FAR of SEQ ID NO: 4.

CCATGGCGACTCAACAACAACAGAACGGTGCATCTGCATCCGGCGTCTTGGAACAACTTCGTGGAAAG
CACGTTCTTATCACAGGTACTACCGGATTTTGGGCAAAGTGGTTCTGGAAAAGTTGATTCGTACTGT
TCCGGATATTGGAGGTATTCATCTGCTGATTCGTGGCAATAAACGTCATCCAGCCGCTCGTGAACGTT
TCCTGAACGAAATTGCGTCCTCCTCCGTCTTCGAACGTTTGCGTGAGGTTACTGGATTAACAGCCGT
ACCTTCTTGGAAGAACGTGTTCACTGTTACCGGTGACGCTTTATTAACAGCCGCTGAATCCCGTTTTGGTTTGACACC
TGAACGTTTTCGTGCTTTGGCCGGTCAGGTTGACGCTTTATTAACAGCCGCTGAATCCCGTTTTGGTTTGACACC
GTGAGCAATTGGATAAAGCCCTGAAAATCAACACCTTGTGTCTTGAAAATGTTGCTGCTCTTGCAGAA
TTGAACTCCCGTACCGCTATGCCGGTCATTCAGGTTTCCACTGTTACGTTAACGTTAAAAACTCCGGTCAAAT
TACCGAATCCGTCATTAAATCGGCTGGCAATCGGCGAATCCATTCCCCGTTCCACTGACGTTACTACGAGATCG
AAGAATTGGTCCATCGTGTTGCAAGACAAGATTTCGATGTTAAAGCTCGTTACTCCGGCAAAGTTCTG

GAGAAAAAATTGGTTGATTTGGGTATTCGTGAGGCCAATAATTACGGATGGTCCGACACCTACACATT
CACCAAATGGTTGGGTGAACAACTGCTGATGAAGGCCTTGTCTGGTCGTTCTTTGACTATTGTGCGTC
CCTCTATTATTGAGTCCGCTTTGGAAGAACCTTCCCCTGGTTGGATCGAAGGCGTTAAAGTTGCCGAT
GCCATTATCTTGGCTTATGCCCGTGAAAAAGTTAGCCTGTTCCCTGGAAAACGTTCCGGCATTATTGA
TGTTATTCCTGTCGATTTGGTTGCGAACTCCATCATCTTGTCTCTGGCTGAGGCGTTGTCTGGTTCTG
GTCAACGTCGTATTTATCAATGTTGCAGCGGTGGTTCTAATCCAATCTCCCTGGGTAAGTTCATTGAT
TATTTGATGGCCGAGGCTAAGACCAACTATGCTGCCTACGATCAACTGTTTTATCGTCGTCCTACTAA
ACCTTTCGTCGCCGTGAACCGTAAATTGTTTGACGTTGTTGTTGGTGGTATGCGTGTTGTCCTTTCTA
TTGCCGGTAAAGCTATGCGTTTGGCTGGTGTAAATCGTGAGTTGAAAGTGCTTAAGAACCTTGATACG
ACCCGTTCCCTTGCAACCATTTTTGGCTTCTATACTGCTCCCGACTATATCTTCCGTAACGATAGCTT
GATGGCCCTGGCTTCTCGTATGGGTGAATTGGATCGTGTTCTTTTCCCAGTTGATGCTCGTCAAATTG
ATTGGCAGTTGTACTTGTGTAAAATTCATTTGGGTGGTCTGAACCGTTACGCTTTGAAGGAACGTAAA
CTGTATTCTTTGCGTGCTGCTGATACTCGTAAAAAAACCGCCTAAGTCGAC

SEQ ID NO: 4_ Variant FAR-V1 polypeptide sequence encoded by the polynucleotide sequence of SEQ ID NO: 3.

MATQQQQNGASASGVLEQLRGKHVLITGTTGFLGKVVLEKLIRTVPDIGGIHLLIRGNKRHPAARERF
LNEIASSSVFERLRHDDNEAFETFLEERVHCITGEVTESRFGLTPERFRALAGQVDAFINSAASVSFR
EQLDKALKINTLCLENVAALAELNSAMAVIQVSTCYVNGKNSGQITESVIKSAGESIPRSTDGYYEIE
ELVHLLQDKISDVKARYSGKVLEKKLVDLGIREANNYGWSDTYTFTKWLGEQLLMKALSGRSLTIVRP
SIIESALEEPSPGWIEGVKVADAIILAYAREKVSLFPGKRSGIIDVIPVDLVANSIILSLAEALSGSG
QRRIYQCCSGGSNPISLGKFIDYLMAEAKTNYAAYDQLFYRRPTKPFVAVNRKLFDVVVGGMRVVLSI
AGKAMRLAGVNRELKVLKNLDTTRSLATIFGFYTAPDYIFRNDSLMALASRMGELDRVLFPVDARQID
WQLYLCKIHLGGLNRYALKERKLYSLRAADTRKKTA

FIG. 3 (Cont. 2)

SEQ ID NO: 5_

Polynucleotide Sequence of the NcoI-SalI DNA fragment coding the FAR variant of SEQ ID NO: 6.

```
CCATGGCGACTCAACAACAGCAGAACGGTGCATCTGCATCCGGCGTCTTGAACAACTTCGTGAAAG
CACGTTCTTATCACAGGTACTACCGGATTTTTGGGCAAAGTGGTTCTGGAAAAGTTGATTCGTACTGT
TCCGGATATTGGAGGTATTCATCTGCTGATTCGTGGCAATAAACGTCATCCAGCCGCTCGTGAACGTT
TCCTGAACGAAATTGCGTCCTCCTCCGTCTTCGAACGTTTGCGTCACGATGATAATGAAGCCTTCGAG
ACCTTCTTGGAAGAACGTGTTCACTGTATTACCGGTGAGGTTACTGAATCCCGTTTTGGTTTGACACC
TGAGCGTTTTCGTGCTTTTGGCCGGTTGACGCGCTTTTATTAACAGCGCTGCAAGCGTGAGTTTTC
GTGAGCAATTGGATAAAGCCCTGAAAATCAACACCTTGTCTTGAAAATGTGCTGCTTGCAGAA
TTGAACTCCGCTATGGCGGTCATTCAGGTTTCCACTGTTACGTTAACGGTAAAACTCCGGTCAAAT
TACCGAATCCGTCATTAAATCGGCTGGCGAATCCATTCCCGTTCCCATGTTACTCACGAGATCG
AAGAATTGGTCCATCTGTTGCAAGACAAGATTTCCCATGTTAAAGCTCGTTACTCCGGCAAAGTTCTG
GAGAAAAAATTGGTTGATTGGGTATTCGTGAGGCCAATAATTACGGATGGTCCGACACCTACACATT
CACCAAATGTTGGGTGAACAACTGCTGAAGAAGGCCTTGTCTGGTCGTCTTCTTTGACTATTGTCGTC
CCTCTATTATTGAGTCCGCTTTGCCCGTTGGATCGAAGGCGTTAAAGTTGCCGAT
GCCATTATCTTGGCTTATGCCGATTGGTTGCGAACTCCATCATCTGTCTCTGTTCCCTGAAAACGTTCCGGCATTATTGA
TGTTATTCCTGTCGATTTGGTTGCAACTCCATCATCTGTCTCTGTTCCCTGAAAACGTTCCGGCATTATTGA
GTCAACGTCGTATTTATCAATGTGCAGCGGTGGTTCTAATCAACTCCCTGGGTAAGTTCATTGAT
TATTTGATGGCCGAGGCTAAGACCAACTATGCTGCCTACGATCAACTGTTTTATCGTCGTCCTACTAA
ACCTTTCGTCGCCGTGAACCGTAAATGCCTTTGGCTGGTAAATCGTGAGTTGAAAGTGCTTAAGAACCTTGATACG
TTGCCGGTAAAGCTATGCCTTTGGCTGGTAAATCGTGAGTTGAAAGTGCTTAAGAACCTTGATACG
ACCCGTAAACTTGCAACCATTTTTGGCTTCTATACTGCTCCCGACTATATCTTCCGTAACGATAGCTT
GATGCCCTCGCTCAGCTTGGGTGAATTGGATCGTGTTCTTTTCCCAGTTGATGCTCGTCGTCAAATTG
```

FIG. 3 (Cont. 3)

ATTGGCAGTTGTACTTGTGTAAAATTCATTGGGTGGTCTGAACCGTTACGCTTTGAAGGAACGTAAA
CTGTATTCTTCGCGTGCTGCTGATACTGACGATAAAACCGCCTAAGTCGAC

SEQ ID NO: 6_ Variant FAR-V2 polypeptide sequence encoded by the polynucleotide sequence of SEQ ID NO: 5.

MATQQQNGASASGVLEQLRGKHVLITGTTGFLGKVVLEKLIRTVPDIGGIHLLIRGNKRHPAARERF
LNEIASSSVFERLRHDDNEAFETFLEERVHCITGEVTESRFGLTPERFRALAGQVDAFINSAASVSFR
EQLDKALKINTLCLENVAALAELNSAMAVIQVSTCYVNGKNSGQITESVIKSAGESIPRSTDGYYEIE
ELVHLLQDKISDVKARYSGKVLEKKLVDLGIREANNYGWSDTYTFTKWLGEQLLMKALSGRSLTIVRP
SIIESALEEPSPGWIEGVKVADAILAYAREKVSLFPGKRSGIIDVIPVDLVANSIILSLAEALSGSG
QRRIYQCCSGGSNPISLGKFIDYLMAEAKTNYAAYDQLFYRRPTKPFVAVNRKLFDVVVGGMRVVLSI
AGKAMRLAGVNRELKVLKNLDTTRKLATIFGFYTAPDYIFRNDSLMALAQRMGELDRVLFPVDARQID
WQLYLCKIHLGGLNRYALKERKLYSSRAADTDDKTA

SEQ ID NO: 17_ Polynucleotide sequence of a codon optimized FAR from Marinobacter aquaeolei.

ATGGCTATCCAGCAGGTTCATCACGCCGACACATCCTCCTCTAAAGTCCTGGTCAACTTCGTGTAA
ACGTGTCTTGATTACCGGCACTACTGGATTCTTGGGTAAAGTCGTCTTGGAACGTTTGATTCGTGCCG
TTCCTGACATCGGTGGCTATCTGCTACCTGCTGATTCGTGGCTAAGAAGCGTCACCCGGATGCTCGTCTCGT
TTCTTGGAGGAGATTGCTACCTCCTCGTCTTTGATCGTTGCGTGAAGTTACTGAAGCTGATTCCGAAGGTTCGA
TGCTTTCCTGAAGAACGTATTCACTGTGTTACTGGTGAAGTTACTGAAGCTGGTTTCGTATTGGTC
AAGAGGACTATCGTAAGTTGGCCACCGAGTTGGACGCAGTCATCAATTCTGCTGCCTCCGTCAACTTC
CGTGAGGAGTTGGATAAGGCTCTGGCCATCAACACTCTGTGTTTGCCTAACATCGCTGGTATGGTGGA

FIG. 3 (Cont. 4)

TCTTAACCCTAAGCTGGCCGTTCTCTTCAAGTCTCTAGCTGTTACGTCAAGGTATGAACTCTGGTCAAG
TTACTGAATCCGTCATCAAACCAGCTGGTGAAGCTGTTCCTCGTTCTCCTGATGGATTCTACGAGATC
GAGGAATTGGTTCGTCGTCTGCTGCTGATTGGTTCCTGAAGACGTTACTCTGGTAAGTTCAAGCACGTTCAAGCACGTTACTCTGGTAAGTGTT
GGAGCGTAAGTTGGTTGGGTGAACAACTCTGATTCCTGAGGCTATTCGTTACGGTTGGTCTGATCATACACCT
TCACGAAATGGTGGGTGAACAACTCTTTGGAAGAACCAGCACCTGGTTGCTGATTGAAGGCTGAAAGTTGCAGA
CCTAGCATCATTGAATCTGTTGAAGAACCAGCACCTGGTTGTTCCGGGTAAACGTTCTGTATCATTG
TGCCGATCATCTTGGCTTATGCTCGTGAGAAGGTTACTTTGTTTCCGGGTAAACGTTCTGTATCATTG
ATGTGATTCCTGTTGACTTGGTTGCCAATTCCATCATCTTTGTCTTTGGCTGAGGCTCTGGGCGAACCT
GGTCGTCGTCGTATCTACCAATGTGTTCTGGTGGTAATCCTATCTCCCTGGGCGAGTTCATTGA
TCACCTGATGGCTGAATCCAAAGCCAACGTGCTGCTTGTTGACTTGGTTATCTCTGGTCCGTCTGCCTTTGTCT
AGCCTTTCCTTGCTGTCAACCGTGCTGCTTGTTGACTTGGTTATCTCTGGTCCGTCTGCCTTTGTCT
TTGACCGACCGTGTCTTGAAGCTGCTGCTGGCAACTCCCGTGACCTGAAGATGCTGCTAACCTGGATAC
TACGCAATCCCTGGCTACTATCTTTGGGCTTCTACACAGCCCCGACTACATCTTCCGTAATGACGAGT
TGATGGCCCTGGCTAACCGTATGGGCGAGTTGATAAGGGTTTGTTCCCCGTTGATGCTCGTCTGATT
GATTGGGAATTGTACCTGCGTAAGATTCACCTGGTGTTGAACCGTTACGCCTTGAAGGAGCGTAA
GGTTTACTCTTTGAAGACAGCCCGTCAGCGTAAGAAGGCAGCTTAA

SEQ ID NO: 18_ FAR polypeptide sequence encoded by the polynucleotide sequence of SEQ ID NO: 17.

MAIQQVHHADTSSSKVLGQLRGKRVLITGTTGFLGKVVLERLIRAVPDIGAIYLLIRGNKRHPDARSR
FLEEIATSSVFDRLREADSEGFDAFLEERIHCVTGEVTEACFGIGQEDYRKLATELDAVINSAASVNF
REELDKALAINTLCLRNIAGMVDLNPKLAVLQVSTCYVNGMNSGQVTESVIKPAGEAVPRSPDGFYEI
EELVRLLQDKIEDVQARYSGKVLERKLVDLGIREANRYGWSDTYTFTKWLGEQLLMKALNGRTLTILR
PSIIESALEEPAPGWIEGVKVADAILAYAREKVTLFPGKRSGIIDVIPVDLVANSIILSLAEALGEP

FIG. 3 (Cont. 5)

GRRRIYQCCSGGGNPISLGEFIDHLMAESKANYAAYDHLFYRQPSKPFLAVNRALFDLVISGVRLPLS
LTDRVLKLLGNSRDLKMLRNLDTTQSLATIFGFYTAPDYIFRNDELMALANRMGEVDKGLFPVDARLI
DWELYLRKIHLAGLNRYALKERKVYSLKTARQRKKAA

SEQ ID NO:27 – Variant FAR-V3 polynucleotide

ATGGCGACTCAACAACAGAACAACGGTGCATCTGCATCCGGCGTCTTGGAAATTCTTCGTGGAAAGCA
CGTTCTTATCACAGGTACTACCGGATTTTTGGGCAAAGTGGTTCTGGAAAAAGTTGATTCGTACTGTTC
CGGATATTGGAGTATTCATCGTGCTGATAAACGTCATCCAGCCGCTCGCGAACGTTTC
CTGAACGAAATTGCGTCCTCCCGTCTTGCGTGTATTACCGGTGAGATTACTGAATCCCGTTTGGTTTGACACCTG
CTTCTTGGAAGAACGTGTTCACTGTATTACCGGTGAGATTACTGAATCCCGTTTGGTTTGACACCTG
AGCGTTTCGTGCTTTGCCGGTCAGGTTGACGGTTCAGGTTGACGCTGCAAGCGTGAACTTTCGT
GAGCAATTGGATAAAGCCCTGAAAATCAACACCCTTGTCTGAAAATGTTGCTGCTCTTGCAGAATT
GAACTCCGCTATGGCGGTCATTCAGGTTTCCACTTGTTACGTTAACGGTAAAACCTCCGGTCAAATTA
CCGAATCCGTCATTAAATCGGCTGGCTGGCAAGACAAGATTTCGTGAGGCCAATAATTACGGATGGTCCGACACCTACACATTCA
GAATTGGTCCATCTGTTGCAAGACAAGATTTCGTGAGGCCAATAATTACGGATGGTCCGACACCTACACATTGCGTCCC
CCAAATGGTTGGGTGAACAACTGCTGAAGAACCTTGTCTGGTTGTCTTTGACTATTGTGCCGATGC
TCTATTATTGAGTCCGCTTTGGCCTTATGCCCGTGAAAAAGTTAGCCTGTTCCCTGGAAAACGTTCCGGCATTATTGATG
CATTATCTTGGCCTTATGCCCGTGAAAAAGTTAGCCTGTTCCCTGGAAAACGTTCCGGCATTATTGATG
TTATTCCTGTCGATTTGGTTGCGAACTCCATCATCTTGTCTCTAATCCAATCAACTGTTGTCTCGGT
CAACGTCGTATTTATCAATGTTGCAGCGGTGGTTCTCAATCCCCTGGGTAAGTTCATTGATTA
TTTGAACGCCGAGGCTAAGACCAACTATGCTGCCTACGATCAACTGTTTATCGTCGTCCTACTAAAC
CTTTCGTGCCCGTGAACCGTAAATTGTTTGACGTTGTTGGTGTCATGCGTGTTGTCCTTTCTATT

FIG. 3 (Cont. 6)

GCCCGCAAAGCTATGCGTTTGGCTGGTGTAAATCGTGAGTTGAAAGTGCTTAAGAACCTTGATACGAC
CCGTAAACTTGCAACCATTTTTGGCTTCTATACTGCTCCCGACTATATCTTCCGTAACGATAGCTTGA
TGGCCCTGGCTCAGCGTATGGGTGAATTGGATCGTGTTCTTTTCCCAGTTGATGCTCGTCAAATTGAT
TGGCAGTTGTACTTGTGTAAAATTCATTTGCGTGGTCTGAACCGTTACGCTTTGAAGGAACGTAAACT
GTATTCTTCGCGTGCTGCTGATACTGACGATAAAACCGCCTAA

SEQ ID NO:28 – Variant FAR-V3 polypeptide

MATQQQNNGASASGVLEILRGKHVLITGTTGFLGKVVLEKLIRTVPDIGGIHLLIRGNKRHPAARERF
LNEIASSSVFERLRHDDNEAFETFLEERVHCITGEITESRFGLTPERFRALAGQVDAFIHSAASVNFR
EQLDKALKINTLCLENVAALAELNSAMAVIQVSTCYVNGKTSGQITESVIKSAGESIPRSTDGYYEIE
ELVHLLQDKISDVKARYSGRVMGKKLVDLGIREANNYGWSDTYTFTKWLGEQLLMKALSGRSLTIVRP
SIIESALEEPSPGWIEGVKVADAIILAYAREKVSLFPGKRSGIIDVIPVDLVANSIILSLAEALSGSG
QRRIYQCCSGGSNPISLGKFIDYLNAEAKTNYAAYDQLFYRRPTKPFVAVNRKLFDVVVGVMRVVLSI
ARKAMRLAGVNRELKVLKNLDTTRKLATIFGFYTAPDYIFRNDSLMALAQRMGELDRVLFPVDARQID
WQLYLCKIHLRGLNRYALKERKLYSSRAADTDDKTA

FIG. 3 (Cont. 7)

SEQUENCE LISTING

<160> NUMBER OF SEQ ID NOS: 104

<210> SEQ ID NO 1
<211> LENGTH: 1539
<212> TYPE: DNA
<213> ORGANISM: Artificial Sequence
<220> FEATURE:
<223> OTHER INFORMATION: Synthetic polynucleotide for codon optimized
      FAR from Marinobactera algicola DG893

<400> SEQUENCE: 1

| | | | | | |
|---|---|---|---|---|---|
| atggctactc | aacaacaaca | gaacggtgca | tctgcatccg | gcgtcttgga | acaacttcgt | 60 |
| ggaaagcacg | ttcttatcac | aggtactacc | ggatttttgg | gcaaagtggt | tctggaaaag | 120 |
| ttgattcgta | ctgttccgga | tattggaggt | attcatctgc | tgattcgtgg | caataaacgt | 180 |
| catccagccg | ctcgtgaacg | tttcctgaac | gaaattgcgt | cctcctccgt | cttcgaacgt | 240 |
| ttgcgtcacg | atgataatga | agccttcgag | accttcttgg | aagaacgtgt | tcactgtatt | 300 |
| accggtgagg | ttactgaatc | cgttttggt | ttgacacctg | aacgttttcg | tgctttggcc | 360 |
| ggtcaggttg | acgcttttat | taacagcgct | gcaagcgtga | actttcgtga | ggaattggat | 420 |
| aaagccctga | aaatcaacac | cttgtgtctt | gaaaatgttg | ctgctcttgc | agaattgaac | 480 |
| tccgctatgg | cggtcattca | ggtttccact | tgttacgtta | acggtaaaaa | ctccggtcaa | 540 |
| attaccgaat | ccgtcattaa | acctgctggc | gaatccattc | cccgttccac | tgacggttac | 600 |
| tacgagatcg | aagaattggt | ccatctgttg | caagacaaga | tttccgatgt | taagctcgt | 660 |
| tactccggca | aagttctgga | gaaaaaattg | gttgatttgg | gtattcgtga | ggccaataat | 720 |
| tacggatggt | ccgacaccta | cacattcacc | aaatggttgg | gtgaacaact | gctgatgaag | 780 |
| gccttgtctg | gtcgttcttt | gactattgtg | cgtccctcta | ttattgagtc | cgctttggaa | 840 |
| gaaccttccc | ctggttggat | cgaaggcgtt | aaagttgccg | atgccattat | cttggcttat | 900 |
| gcccgtgaaa | aagttagcct | gttccctgga | aaacgttccg | gcattattga | tgttattcct | 960 |
| gtcgatttgg | ttgcgaactc | catcatcttg | tctctggctg | aggcgttgtc | tggttctggt | 1020 |
| caacgtcgta | tttatcaatg | ttgcagcggt | ggttctaatc | aatctccct | gggtaagttc | 1080 |
| attgattatt | tgatggccga | ggctaagacc | aactatgctg | cctacgatca | actgttttat | 1140 |
| cgtcgtccta | ctaaacccttt | cgtcgccgtg | aaccgtaaat | tgtttgacgt | tgttgttggt | 1200 |
| ggtatgcgtg | ttcctctttc | tattgccggt | aaagctatgc | gtttggctgg | tcaaaatcgt | 1260 |
| gagttgaaag | tgcttaagaa | ccttgatacg | acccgttccc | ttgcaaccat | ttttggcttc | 1320 |
| tatactgctc | ccgactatat | cttccgtaac | gatagcttga | tggccctggc | ttctcgtatg | 1380 |
| ggtgaattgg | atcgtgttct | tttcccagtt | gatgctcgtc | aaattgattg | gcagttgtac | 1440 |
| ttgtgtaaaa | ttcatttggg | tggtctgaac | cgttacgctt | tgaaggaacg | taaactgtat | 1500 |
| tctttgcgtg | ctgctgatac | tcgtaaaaaa | gctgcctaa | | | 1539 |

<210> SEQ ID NO 2
<211> LENGTH: 512
<212> TYPE: PRT
<213> ORGANISM: Artificial Sequence
<220> FEATURE:
<223> OTHER INFORMATION: Synthetic polypeptide encoded by SEQ ID NO:1

<400> SEQUENCE: 2

Met Ala Thr Gln Gln Gln Gln Asn Gly Ala Ser Ala Ser Gly Val Leu
1               5                   10                  15

Glu Gln Leu Arg Gly Lys His Val Leu Ile Thr Gly Thr Thr Gly Phe

```
                 20                  25                  30
Leu Gly Lys Val Val Leu Glu Lys Leu Ile Arg Thr Val Pro Asp Ile
             35                  40                  45
Gly Gly Ile His Leu Leu Ile Arg Gly Asn Lys Arg His Pro Ala Ala
             50                  55                  60
Arg Glu Arg Phe Leu Asn Glu Ile Ala Ser Ser Val Phe Glu Arg
 65                  70                  75                  80
Leu Arg His Asp Asp Asn Glu Ala Phe Glu Thr Phe Leu Glu Arg
                 85                  90                  95
Val His Cys Ile Thr Gly Glu Val Thr Glu Ser Arg Phe Gly Leu Thr
             100                 105                 110
Pro Glu Arg Phe Arg Ala Leu Ala Gly Gln Val Asp Ala Phe Ile Asn
             115                 120                 125
Ser Ala Ala Ser Val Asn Phe Arg Glu Glu Leu Asp Lys Ala Leu Lys
             130                 135                 140
Ile Asn Thr Leu Cys Leu Glu Asn Val Ala Ala Leu Ala Glu Leu Asn
145                 150                 155                 160
Ser Ala Met Ala Val Ile Gln Val Ser Thr Cys Tyr Val Asn Gly Lys
             165                 170                 175
Asn Ser Gly Gln Ile Thr Glu Ser Val Ile Lys Pro Ala Gly Glu Ser
             180                 185                 190
Ile Pro Arg Ser Thr Asp Gly Tyr Tyr Glu Ile Glu Glu Leu Val His
             195                 200                 205
Leu Leu Gln Asp Lys Ile Ser Asp Val Lys Ala Arg Tyr Ser Gly Lys
             210                 215                 220
Val Leu Glu Lys Lys Leu Val Asp Leu Gly Ile Arg Glu Ala Asn Asn
225                 230                 235                 240
Tyr Gly Trp Ser Asp Thr Tyr Thr Phe Thr Lys Trp Leu Gly Glu Gln
             245                 250                 255
Leu Leu Met Lys Ala Leu Ser Gly Arg Ser Leu Thr Ile Val Arg Pro
             260                 265                 270
Ser Ile Ile Glu Ser Ala Leu Glu Glu Pro Ser Pro Gly Trp Ile Glu
             275                 280                 285
Gly Val Lys Val Ala Asp Ala Ile Ile Leu Ala Tyr Ala Arg Glu Lys
             290                 295                 300
Val Ser Leu Phe Pro Gly Lys Arg Ser Gly Ile Ile Asp Val Ile Pro
305                 310                 315                 320
Val Asp Leu Val Ala Asn Ser Ile Ile Leu Ser Leu Ala Glu Ala Leu
             325                 330                 335
Ser Gly Ser Gly Gln Arg Arg Ile Tyr Gln Cys Cys Ser Gly Gly Ser
             340                 345                 350
Asn Pro Ile Ser Leu Gly Lys Phe Ile Asp Tyr Leu Met Ala Glu Ala
             355                 360                 365
Lys Thr Asn Tyr Ala Ala Tyr Asp Gln Leu Phe Tyr Arg Arg Pro Thr
             370                 375                 380
Lys Pro Phe Val Ala Val Asn Arg Lys Leu Phe Asp Val Val Gly
385                 390                 395                 400
Gly Met Arg Val Pro Leu Ser Ile Ala Gly Lys Ala Met Arg Leu Ala
             405                 410                 415
Gly Gln Asn Arg Glu Leu Lys Val Leu Lys Asn Leu Asp Thr Thr Arg
             420                 425                 430
Ser Leu Ala Thr Ile Phe Gly Phe Tyr Thr Ala Pro Asp Tyr Ile Phe
             435                 440                 445
```

Arg Asn Asp Ser Leu Met Ala Leu Ala Ser Arg Met Gly Glu Leu Asp
            450                 455                 460

Arg Val Leu Phe Pro Val Asp Ala Arg Gln Ile Asp Trp Gln Leu Tyr
465                 470                 475                 480

Leu Cys Lys Ile His Leu Gly Gly Leu Asn Arg Tyr Ala Leu Lys Glu
                485                 490                 495

Arg Lys Leu Tyr Ser Leu Arg Ala Ala Asp Thr Arg Lys Lys Ala Ala
            500                 505                 510

<210> SEQ ID NO 3
<211> LENGTH: 1547
<212> TYPE: DNA
<213> ORGANISM: Artificial Sequence
<220> FEATURE:
<223> OTHER INFORMATION: Synthetic polynucleotide encoding FAR variant

<400> SEQUENCE: 3

```
ccatggcgac tcaacaacaa cagaacggtg catctgcatc cggcgtcttg gaacaacttc      60
gtggaaagca cgttcttatc acaggtacta ccggattttt gggcaaagtg gttctggaaa     120
agttgattcg tactgttccg gatattggag gtattcatct gctgattcgt ggcaataaac     180
gtcatccagc cgctcgtgaa cgtttcctga cgaaattgc gtcctcctcc gtcttcgaac      240
gtttgcgtca cgatgataat gaagccttcg agaccttctt ggaagaacgt gttcactgta     300
ttaccggtga ggttactgaa tcccgttttg gtttgacacc tgaacgtttt cgtgctttgg     360
ccggtcaggt tgacgctttt attaacagcg ctgcaagcgt gagttttcgt gagcaattgg     420
ataaagccct gaaaatcaac accttgtgtc ttgaaaatgt tgctgctctt gcagaattga     480
actccgctat ggcggtcatt caggtttcca cttgttacgt taacggtaaa aactccggtc     540
aaattaccga atccgtcatt aaatcggctg gcgaatccat tccccgttcc actgacggtt     600
actacgagat cgaagaattg gtccatctgt tgcaagacaa gatttccgat gttaaagctc     660
gttactccgg caaagttctg gagaaaaaat tggttgattt gggtattcgt gaggccaata     720
attacgatg gtccgacacc tacacattca ccaaatggtt gggtgaacaa ctgctgatga     780
aggccttgtc tggtcgttct ttgactattg tgcgtccctc tattattgag tccgctttgg     840
aagaaccttc ccctggttgg atcgaaggcg ttaaagttgc cgatgccatt atcttggctt     900
atgcccgtga aaagtttagc ctgttccctg gaaaacgttc cggcattatt gatgttattc     960
ctgtcgattt ggttgcgaac tccatcatct gtctctggc tgaggcgttg tctggttctg    1020
gtcaacgtcg tatttatcaa tgttgcagcg gtggttctaa tccaatctcc ctgggtaagt    1080
tcattgatta tttgatggcc gaggctaaga ccaactatgc tgcctacgat caactgttt    1140
atcgtcgtcc tactaaacct ttcgtcgccg tgaaccgtaa attgtttgac gttgttgttg    1200
gtggtatgcg tgttgtcctt tctattgccg gtaaagctat gcgtttggct ggtgtaaatc    1260
gtgagttgaa agtgcttaag aaccttgata cgacccgttc ccttgcaacc attttggct    1320
tctatactgc tcccgactat atcttccgta acgatagctt gatggccctg gcttctcgta    1380
tgggtgaatt ggatcgtgtt cttttcccag ttgatgctcg tcaaattgat tggcagttgt    1440
acttgtgtaa aattcatttg ggtggtctga accgttacgc tttgaaggaa cgtaaactgt    1500
attctttgcg tgctgctgat actcgtaaaa aaccgccta agtcgac                   1547
```

<210> SEQ ID NO 4
<211> LENGTH: 512
<212> TYPE: PRT

<213> ORGANISM: Artificial Sequence
<220> FEATURE:
<223> OTHER INFORMATION: Synthetic polypeptide encoded by SEQ ID NO:3

<400> SEQUENCE: 4

```
Met Ala Thr Gln Gln Gln Asn Gly Ala Ser Ala Ser Gly Val Leu
1               5                   10                  15

Glu Gln Leu Arg Gly Lys His Val Leu Ile Thr Gly Thr Thr Gly Phe
            20                  25                  30

Leu Gly Lys Val Val Leu Glu Lys Leu Ile Arg Thr Val Pro Asp Ile
        35                  40                  45

Gly Gly Ile His Leu Leu Ile Arg Gly Asn Lys Arg His Pro Ala Ala
    50                  55                  60

Arg Glu Arg Phe Leu Asn Glu Ile Ala Ser Ser Val Phe Glu Arg
65                  70                  75                  80

Leu Arg His Asp Asp Asn Glu Ala Phe Glu Thr Phe Leu Glu Glu Arg
                85                  90                  95

Val His Cys Ile Thr Gly Glu Val Thr Glu Ser Arg Phe Gly Leu Thr
            100                 105                 110

Pro Glu Arg Phe Arg Ala Leu Ala Gly Gln Val Asp Ala Phe Ile Asn
        115                 120                 125

Ser Ala Ala Ser Val Ser Phe Arg Glu Gln Leu Asp Lys Ala Leu Lys
    130                 135                 140

Ile Asn Thr Leu Cys Leu Glu Asn Val Ala Ala Leu Ala Glu Leu Asn
145                 150                 155                 160

Ser Ala Met Ala Val Ile Gln Val Ser Thr Cys Tyr Val Asn Gly Lys
                165                 170                 175

Asn Ser Gly Gln Ile Thr Glu Ser Val Ile Lys Ser Ala Gly Glu Ser
            180                 185                 190

Ile Pro Arg Ser Thr Asp Gly Tyr Tyr Glu Ile Glu Glu Leu Val His
        195                 200                 205

Leu Leu Gln Asp Lys Ile Ser Asp Val Lys Ala Arg Tyr Ser Gly Lys
    210                 215                 220

Val Leu Glu Lys Lys Leu Val Asp Leu Gly Ile Arg Glu Ala Asn Asn
225                 230                 235                 240

Tyr Gly Trp Ser Asp Thr Tyr Thr Phe Thr Lys Trp Leu Gly Glu Gln
                245                 250                 255

Leu Leu Met Lys Ala Leu Ser Gly Arg Ser Leu Thr Ile Val Arg Pro
            260                 265                 270

Ser Ile Ile Glu Ser Ala Leu Glu Glu Pro Ser Pro Gly Trp Ile Glu
        275                 280                 285

Gly Val Lys Val Ala Asp Ala Ile Ile Leu Ala Tyr Ala Arg Glu Lys
    290                 295                 300

Val Ser Leu Phe Pro Gly Lys Arg Ser Gly Ile Ile Asp Val Ile Pro
305                 310                 315                 320

Val Asp Leu Val Ala Asn Ser Ile Ile Leu Ser Leu Ala Glu Ala Leu
                325                 330                 335

Ser Gly Ser Gly Gln Arg Arg Ile Tyr Gln Cys Cys Ser Gly Gly Ser
            340                 345                 350

Asn Pro Ile Ser Leu Gly Lys Phe Ile Asp Tyr Leu Met Ala Glu Ala
        355                 360                 365

Lys Thr Asn Tyr Ala Ala Tyr Asp Gln Leu Phe Tyr Arg Arg Pro Thr
    370                 375                 380

Lys Pro Phe Val Ala Val Asn Arg Lys Leu Phe Asp Val Val Val Gly
```

Gly Met Arg Val Val Leu Ser Ile Ala Gly Lys Ala Met Arg Leu Ala
385                 390                 395                 400
                405                 410                 415

Gly Val Asn Arg Glu Leu Lys Val Leu Lys Asn Leu Asp Thr Thr Arg
                420                 425                 430

Ser Leu Ala Thr Ile Phe Gly Phe Tyr Thr Ala Pro Asp Tyr Ile Phe
                435                 440                 445

Arg Asn Asp Ser Leu Met Ala Leu Ala Ser Arg Met Gly Glu Leu Asp
                450                 455                 460

Arg Val Leu Phe Pro Val Asp Ala Arg Gln Ile Asp Trp Gln Leu Tyr
465                 470                 475                 480

Leu Cys Lys Ile His Leu Gly Gly Leu Asn Arg Tyr Ala Leu Lys Glu
                485                 490                 495

Arg Lys Leu Tyr Ser Leu Arg Ala Ala Asp Thr Arg Lys Lys Thr Ala
                500                 505                 510

<210> SEQ ID NO 5
<211> LENGTH: 1547
<212> TYPE: DNA
<213> ORGANISM: Artificial Sequence
<220> FEATURE:
<223> OTHER INFORMATION: Synthetic polynucleotide encoding FAR variant

<400> SEQUENCE: 5

| | | | | | |
|---|---|---|---|---|---|
| ccatggcgac | tcaacaacag | cagaacggtg | catctgcatc | cggcgtcttg | gaacaacttc | 60 |
| gtggaaagca | cgttcttatc | acaggtacta | ccggattttt | gggcaaagtg | gttctggaaa | 120 |
| agttgattcg | tactgttccg | gatattggag | gtattcatct | gctgattcgt | ggcaataaac | 180 |
| gtcatccagc | cgctcgtgaa | cgtttcctga | acgaaattgc | gtcctcctcc | gtcttcgaac | 240 |
| gtttgcgtca | cgatgataat | gaagccttcg | agaccttctt | ggaagaacgt | gttcactgta | 300 |
| ttaccggtga | ggttactgaa | tcccgttttg | gtttgacacc | tgagcgtttt | cgtgctttgg | 360 |
| ccggtcaggt | tgacgctttt | attaacagcg | ctgcaagcgt | gagttttcgt | gagcaattgg | 420 |
| ataaagccct | gaaaatcaac | accttgtgtc | ttgaaaatgt | tgctgctctt | gcagaattga | 480 |
| actccgctat | ggcggtcatt | caggtttcca | cttgttacgt | taacggtaaa | aactccggtc | 540 |
| aaattaccga | atccgtcatt | aaatcggctg | gcgaatccat | tccccgttcc | actgacggtt | 600 |
| actacgagat | cgaagaattg | gtccatctgt | tgcaagacaa | gatttccgat | gttaaagctc | 660 |
| gttactccgg | caaagttctg | gagaaaaaat | tggttgattt | gggtattcgt | gaggccaata | 720 |
| attacggatg | gtccgacacc | tacacattca | ccaaatggtt | gggtgaacaa | ctgctgatga | 780 |
| aggccttgtc | tggtcgttct | ttgactattg | tgcgtccctc | tattattgag | tccgctttgg | 840 |
| aagaaccttc | ccctggttgg | atcgaaggcg | ttaaagttgc | cgatgccatt | atcttggctt | 900 |
| atgcccgtga | aaaagttagc | ctgttccctg | gaaaacgttc | cggcattatt | gatgttattc | 960 |
| ctgtcgattt | ggttgcgaac | tccatcatct | tgtctctggc | tgaggcgttg | tctggttctg | 1020 |
| gtcaacgtcg | tatttatcaa | tgttgcagcg | gtggttctaa | tccaatctcc | ctgggtaagt | 1080 |
| tcattgatta | tttgatggcc | gaggctaaga | ccaactatgc | tgcctacgat | caactgtttt | 1140 |
| atcgtcgtcc | tactaaacct | ttcgtcgccg | tgaaccgtaa | attgtttgac | gttgttgttg | 1200 |
| gtggtatgcg | tgttgtcctt | tctattgccg | gtaaagctat | gcgtttggct | ggtgtaaatc | 1260 |
| gtgagttgaa | agtgcttaag | aaccttgata | cgacccgtaa | acttgcaacc | atttttggct | 1320 |
| tctatactgc | tcccgactat | atcttccgta | acgatagctt | gatggccctg | gctcagcgta | 1380 |

```
tgggtgaatt ggatcgtgtt cttttcccag ttgatgctcg tcaaattgat tggcagttgt   1440
acttgtgtaa aattcatttg ggtggtctga accgttacgc tttgaaggaa cgtaaactgt   1500
attcttcgcg tgctgctgat actgacgata aaaccgccta agtcgac                 1547
```

<210> SEQ ID NO 6
<211> LENGTH: 512
<212> TYPE: PRT
<213> ORGANISM: Artificial Sequence
<220> FEATURE:
<223> OTHER INFORMATION: Synthetic polypeptide encoded by SEQ ID NO:5

<400> SEQUENCE: 6

```
Met Ala Thr Gln Gln Gln Gln Asn Gly Ala Ser Ala Ser Gly Val Leu
1               5                   10                  15

Glu Gln Leu Arg Gly Lys His Val Leu Ile Thr Gly Thr Thr Gly Phe
            20                  25                  30

Leu Gly Lys Val Val Leu Glu Lys Leu Ile Arg Thr Val Pro Asp Ile
        35                  40                  45

Gly Gly Ile His Leu Leu Ile Arg Gly Asn Lys Arg His Pro Ala Ala
    50                  55                  60

Arg Glu Arg Phe Leu Asn Glu Ile Ala Ser Ser Val Phe Glu Arg
65                  70                  75                  80

Leu Arg His Asp Asp Asn Glu Ala Phe Glu Thr Phe Leu Glu Arg
                85                  90                  95

Val His Cys Ile Thr Gly Glu Val Thr Glu Ser Arg Phe Gly Leu Thr
            100                 105                 110

Pro Glu Arg Phe Arg Ala Leu Ala Gly Gln Val Asp Ala Phe Ile Asn
        115                 120                 125

Ser Ala Ala Ser Val Ser Phe Arg Glu Gln Leu Asp Lys Ala Leu Lys
    130                 135                 140

Ile Asn Thr Leu Cys Leu Glu Asn Val Ala Ala Leu Ala Glu Leu Asn
145                 150                 155                 160

Ser Ala Met Ala Val Ile Gln Val Ser Thr Cys Tyr Val Asn Gly Lys
                165                 170                 175

Asn Ser Gly Gln Ile Thr Glu Ser Val Ile Lys Ser Ala Gly Glu Ser
            180                 185                 190

Ile Pro Arg Ser Thr Asp Gly Tyr Tyr Glu Ile Glu Glu Leu Val His
        195                 200                 205

Leu Leu Gln Asp Lys Ile Ser Asp Val Lys Ala Arg Tyr Ser Gly Lys
    210                 215                 220

Val Leu Glu Lys Lys Leu Val Asp Leu Gly Ile Arg Glu Ala Asn Asn
225                 230                 235                 240

Tyr Gly Trp Ser Asp Thr Tyr Thr Phe Thr Lys Trp Leu Gly Glu Gln
                245                 250                 255

Leu Leu Met Lys Ala Leu Ser Gly Arg Ser Leu Thr Ile Val Arg Pro
            260                 265                 270

Ser Ile Ile Glu Ser Ala Leu Glu Glu Pro Ser Pro Gly Trp Ile Glu
        275                 280                 285

Gly Val Lys Val Ala Asp Ala Ile Ile Leu Ala Tyr Ala Arg Glu Lys
    290                 295                 300

Val Ser Leu Phe Pro Gly Lys Arg Ser Gly Ile Ile Asp Val Ile Pro
305                 310                 315                 320

Val Asp Leu Val Ala Asn Ser Ile Ile Leu Ser Leu Ala Glu Ala Leu
                325                 330                 335
```

```
Ser Gly Ser Gly Gln Arg Arg Ile Tyr Gln Cys Cys Ser Gly Gly Ser
            340                 345                 350

Asn Pro Ile Ser Leu Gly Lys Phe Ile Asp Tyr Leu Met Ala Glu Ala
            355                 360                 365

Lys Thr Asn Tyr Ala Ala Tyr Asp Gln Leu Phe Tyr Arg Arg Pro Thr
        370                 375                 380

Lys Pro Phe Val Ala Val Asn Arg Lys Leu Phe Asp Val Val Gly
385                 390                 395                 400

Gly Met Arg Val Val Leu Ser Ile Ala Gly Lys Ala Met Arg Leu Ala
                405                 410                 415

Gly Val Asn Arg Glu Leu Lys Val Leu Lys Asn Leu Asp Thr Thr Arg
            420                 425                 430

Lys Leu Ala Thr Ile Phe Gly Phe Tyr Thr Ala Pro Asp Tyr Ile Phe
        435                 440                 445

Arg Asn Asp Ser Leu Met Ala Leu Ala Gln Arg Met Gly Glu Leu Asp
        450                 455                 460

Arg Val Leu Phe Pro Val Asp Ala Arg Gln Ile Asp Trp Gln Leu Tyr
465                 470                 475                 480

Leu Cys Lys Ile His Leu Gly Gly Leu Asn Arg Tyr Ala Leu Lys Glu
                485                 490                 495

Arg Lys Leu Tyr Ser Ser Arg Ala Ala Asp Thr Asp Lys Thr Ala
            500                 505                 510

<210> SEQ ID NO 7
<211> LENGTH: 456
<212> TYPE: DNA
<213> ORGANISM: Escherichia coli

<400> SEQUENCE: 7
atgactacta acactcatac tctgcagatt gaagagattt tagaacttct gccgcaccgt      60
ttcccgttct tactggtgga tcgcgtgctg gattttgaag aaggtcgttt tctgcgcgca     120
gtaaaaaatg tctctgtcaa tgagccattc ttccagggcc atttccctgg aaaaccgatt     180
ttcccgggtg tgctgattct ggaagcaatg gcacaggcaa caggtattct ggcgtttaaa     240
agcgtaggaa aactggaacc gggtgagctg tactacttcg ctggtattga cgaagcgcgc     300
ttcaagcgcc cggtcgtgcc tggcgatcaa atgatcatgg aagtcacttt cgaaaaaacg     360
cgccgcggcc tgacccgttt taaaggggtt gctctggtcg atggtaaagt agtttgcgaa     420
gcaacgatga tgtgtgctcg tagccgggag gcctaa                              456

<210> SEQ ID NO 8
<211> LENGTH: 151
<212> TYPE: PRT
<213> ORGANISM: Escherichia coli

<400> SEQUENCE: 8

Met Thr Thr Asn Thr His Thr Leu Gln Ile Glu Glu Ile Leu Glu Leu
1               5                   10                  15

Leu Pro His Arg Phe Pro Phe Leu Leu Val Asp Arg Val Leu Asp Phe
            20                  25                  30

Glu Glu Gly Arg Phe Leu Arg Ala Val Lys Asn Val Ser Val Asn Glu
        35                  40                  45

Pro Phe Phe Gln Gly His Phe Pro Gly Lys Pro Ile Phe Pro Gly Val
    50                  55                  60

Leu Ile Leu Glu Ala Met Ala Gln Ala Thr Gly Ile Leu Ala Phe Lys
65                  70                  75                  80
```

Ser Val Gly Lys Leu Glu Pro Gly Glu Leu Tyr Tyr Phe Ala Gly Ile
            85                  90                  95

Asp Glu Ala Arg Phe Lys Arg Pro Val Val Pro Gly Asp Gln Met Ile
            100                 105                 110

Met Glu Val Thr Phe Glu Lys Thr Arg Arg Gly Leu Thr Arg Phe Lys
            115                 120                 125

Gly Val Ala Leu Val Asp Gly Lys Val Val Cys Glu Ala Thr Met Met
            130                 135                 140

Cys Ala Arg Ser Arg Glu Ala
145                 150

<210> SEQ ID NO 9
<211> LENGTH: 519
<212> TYPE: DNA
<213> ORGANISM: Escherichia coli

<400> SEQUENCE: 9
atggtagata aacgcgaatc ctatacaaaa gaagaccttc ttgcctctgg tcgcggtgaa      60
ctgtttggcg ctaaaggccc gcaattgcca gcaccgaaca tgctgatgat ggaccgtgtg     120
gtcaaaatga ccgaaacggg tggtaacttc gacaaaggt atgttgaagc agaactggat     180
atcaatccgg atctgtggtt cttcggatgc cactttattg gcgatccggt tatgccggga     240
tgcctgggcc tggacgcaat gtggcagctg gtagggttct acctcggctg gctgggcggc     300
gaaggtaaag ccgcgcgct gggcgttggc gaagtgaaat tcactggtca ggtactgccg     360
acagcgaaaa aagtgaccta ccgtattcac tttaaacgca ttgttaaccg tcgtctgatt     420
atgggcctgg cggatggcga agtgctggtt gatggtcgtc tgatctatac cgccagcgac     480
ctgaaagtcg gtctgttcca ggatacgtct gccttctaa                           519

<210> SEQ ID NO 10
<211> LENGTH: 172
<212> TYPE: PRT
<213> ORGANISM: Escherichia coli

<400> SEQUENCE: 10

Met Val Asp Lys Arg Glu Ser Tyr Thr Lys Glu Asp Leu Leu Ala Ser
1               5                   10                  15

Gly Arg Gly Glu Leu Phe Gly Ala Lys Gly Pro Gln Leu Pro Ala Pro
            20                  25                  30

Asn Met Leu Met Met Asp Arg Val Val Lys Met Thr Glu Thr Gly Gly
            35                  40                  45

Asn Phe Asp Lys Gly Tyr Val Glu Ala Glu Leu Asp Ile Asn Pro Asp
        50                  55                  60

Leu Trp Phe Phe Gly Cys His Phe Ile Gly Asp Pro Val Met Pro Gly
65                  70                  75                  80

Cys Leu Gly Leu Asp Ala Met Trp Gln Leu Val Gly Phe Tyr Leu Gly
            85                  90                  95

Trp Leu Gly Gly Glu Gly Lys Gly Arg Ala Leu Gly Val Gly Glu Val
            100                 105                 110

Lys Phe Thr Gly Gln Val Leu Pro Thr Ala Lys Lys Val Thr Tyr Arg
            115                 120                 125

Ile His Phe Lys Arg Ile Val Asn Arg Arg Leu Ile Met Gly Leu Ala
            130                 135                 140

Asp Gly Glu Val Leu Val Asp Gly Arg Leu Ile Tyr Thr Ala Ser Asp
145                 150                 155                 160

Leu Lys Val Gly Leu Phe Gln Asp Thr Ser Ala Phe
            165                 170

<210> SEQ ID NO 11
<211> LENGTH: 821
<212> TYPE: DNA
<213> ORGANISM: Artificial Sequence
<220> FEATURE:
<223> OTHER INFORMATION: Synthetic polynucleotide for E. coli codon
      optimized FabI-1 gene from Rhodobacter sphaeroides SB103

<400> SEQUENCE: 11

```
atgaccgcag gactgatggc tggcaaacgt ggactgatta tgggcctggc caatgataaa      60
tcaatcgcgt ggggcattgc taaagcactg gtgatgcag gtgcggaact ggcgttttct     120
taccagggtg aagcactgaa gaagcgtgtt gaaccactgg ctgcaagcct gggcaccccg     180
ctgttattcg aatgtgatgt ggcaaacgaa gactcaatgg acgccctgtt tgcgggactg     240
aaagacgcat ggggcaccct ggattttgtt gtgcatgcaa ttggctttag cgataaaaac     300
gaactgcgcg gtcgttacgt ggatacgagc cgcggtaatt tcacgatgac gatggacatt     360
tcagtgtata gctttactgc tgtttgcgca cgcgctgctg ccatgatgcc gaacggtggt     420
agcctgctga ccctgaccta ctatggagcc gaacaggtaa tgccgcatta taacgttatg     480
ggtgtggcga aagctgcgct tgaagcaagc gtgaaataca tcgcggaaga tctgggcaaa     540
ctgggcattc gttgtaatgc tatctcggct ggcccgatta aaaccctggc tgcaagcggc     600
attggcgact ttcgctatat catgaagtgg aacgagctga acagcccgct gcgccgcaac     660
gttacccagg aagaagttgg caaagccgcg ttatatctgt tgagcgatct gggcagcggc     720
accaccggtg aaaacctgca tgtggatgcc gttaccacgt cgtcggcatg aaagcggttg     780
atgcgccgga tattgacgta gtcacgggtc gtaaagacta a                        821
```

<210> SEQ ID NO 12
<211> LENGTH: 273
<212> TYPE: PRT
<213> ORGANISM: Artificial Sequence
<220> FEATURE:
<223> OTHER INFORMATION: Synthetic polypeptide encoded by SEQ ID NO:11

<400> SEQUENCE: 12

Met Thr Ala Gly Leu Met Ala Gly Lys Arg Gly Leu Ile Met Gly Leu
1               5                   10                  15

Ala Asn Asp Lys Ser Ile Ala Trp Gly Ile Ala Lys Ala Leu Gly Asp
            20                  25                  30

Ala Gly Ala Glu Leu Ala Phe Ser Tyr Gln Gly Glu Ala Leu Lys Lys
        35                  40                  45

Arg Val Glu Pro Leu Ala Ala Ser Leu Gly Thr Pro Leu Leu Phe Glu
    50                  55                  60

Cys Asp Val Ala Asn Glu Asp Ser Met Asp Ala Leu Phe Ala Gly Leu
65                  70                  75                  80

Lys Asp Ala Trp Gly Thr Leu Asp Phe Val Val His Ala Ile Gly Phe
                85                  90                  95

Ser Asp Lys Asn Glu Leu Arg Gly Arg Tyr Val Asp Thr Ser Arg Gly
            100                 105                 110

Asn Phe Thr Met Thr Met Asp Ile Ser Val Tyr Ser Phe Thr Ala Val
        115                 120                 125

Cys Ala Arg Ala Ala Ala Met Met Pro Asn Gly Gly Ser Leu Leu Thr
    130                 135                 140

```
Leu Thr Tyr Tyr Gly Ala Glu Gln Val Met Pro His Tyr Asn Val Met
145                 150                 155                 160

Gly Val Ala Lys Ala Ala Leu Glu Ala Ser Val Lys Tyr Ile Ala Glu
            165                 170                 175

Asp Leu Gly Lys Leu Gly Ile Arg Cys Asn Ala Ile Ser Ala Gly Pro
        180                 185                 190

Ile Lys Thr Leu Ala Ala Ser Gly Ile Gly Asp Phe Arg Tyr Ile Met
    195                 200                 205

Lys Trp Asn Glu Leu Asn Ser Pro Leu Arg Arg Asn Val Thr Gln Glu
210                 215                 220

Glu Val Gly Lys Ala Ala Leu Tyr Leu Leu Ser Asp Leu Gly Ser Gly
225                 230                 235                 240

Thr Thr Gly Glu Asn Leu His Val Asp Ala Gly Tyr His Val Val Gly
            245                 250                 255

Met Lys Ala Val Asp Ala Pro Asp Ile Asp Val Val Thr Gly Arg Lys
            260                 265                 270

Asp

<210> SEQ ID NO 13
<211> LENGTH: 1242
<212> TYPE: DNA
<213> ORGANISM: Escherichia coli

<400> SEQUENCE: 13
gtgtctaagc gtcgtgtagt tgtgaccgga ctgggcatgt tgtctcctgt cggcaatacc     60
gtagagtcta cctggaaagc tctgcttgcc ggtcagagtg catcagcct aatcgaccat    120 ttcgatacta gcgcctatgc aacgaaattt gctggcttag taaaggattt taactgtgag   180
gacattatct cgcgcaaaga acagcgcaag atggatgcct tcattcaata tggaattgtc   240
gctggcgttc aggccatgca ggattctggc cttgaaataa cggaagagaa cgcaaccccgc  300 attggtgccg caattggctc cgggattggc ggcctcggac tgatcgaaga aaaccacaca   360
tctctgatga acgtggtgcc acgtaagatc agcccattct tcgttccgtc aacgattgtg   420
aacatggtgg caggtcatct gactatcatg tatggcctgc gtggcccgag catctctatc   480
gcgactgcct gtacttccgg cgtgcacaac attggccatg ctgcgcgtat tatcgcgtat   540
ggcgatgctg acgtgatggt tgcaggtggc gcagagaaag ccagtacgcc gctgggcgtt   600
ggtggttttg gcgcggcacg tgcattatct acccgcaatg ataacccgca agcggcgagc   660
cgcccgtggg ataaagagcg tgatggtttc gtactgggcg atggtgccgg tatgctggta   720
cttgaagagt acgaacacgc gaaaaaacgc ggtgcgaaaa tttacgctga actcgtcggc   780
tttggtatga gcagcgatgc ttatcatatg acgtcaccgc cagaaaatgg cgcaggcgca   840
gctctggcga tggcaaatgc tctgcgtgat gcaggcattg aagcgagtca gattggctac   900
gttaacgcgc acggtacttc tacgccggct ggcgataaag ctgaagcgca ggcggtgaaa   960
accatcttcg gtgaagctgc aagccgtgtg ttggtaagct ccacgaaatc tatgaccggt  1020
cacctgttag gtgcggcggg tgcagtagaa tctatctact ccatcctggc gctgcgcgat  1080
caggctgttc cgccaaccat caacctggat aacccggatg aaggttgcga tctggatttc  1140
gtaccgcacg aagcgcgtca ggttagcgga atggaataca ctctgtgtaa ctccttcggc  1200
ttcggtggca ctaatggttc tttgatcttt aaaaagatct aa                     1242

<210> SEQ ID NO 14
```

<211> LENGTH: 413
<212> TYPE: PRT
<213> ORGANISM: Escherichia coli

<400> SEQUENCE: 14

```
Met Ser Lys Arg Arg Val Val Thr Gly Leu Gly Met Leu Ser Pro
1               5                   10                  15

Val Gly Asn Thr Val Glu Ser Thr Trp Lys Ala Leu Leu Ala Gly Gln
            20                  25                  30

Ser Gly Ile Ser Leu Ile Asp His Phe Asp Thr Ser Ala Tyr Ala Thr
        35                  40                  45

Lys Phe Ala Gly Leu Val Lys Asp Phe Asn Cys Glu Asp Ile Ile Ser
50                  55                  60

Arg Lys Glu Gln Arg Lys Met Asp Ala Phe Ile Gln Tyr Gly Ile Val
65                  70                  75                  80

Ala Gly Val Gln Ala Met Gln Asp Ser Gly Leu Glu Ile Thr Glu Glu
                85                  90                  95

Asn Ala Thr Arg Ile Gly Ala Ala Ile Gly Ser Gly Ile Gly Gly Leu
            100                 105                 110

Gly Leu Ile Glu Glu Asn His Thr Ser Leu Met Asn Gly Gly Pro Arg
        115                 120                 125

Lys Ile Ser Pro Phe Phe Val Pro Ser Thr Ile Val Asn Met Val Ala
130                 135                 140

Gly His Leu Thr Ile Met Tyr Gly Leu Arg Gly Pro Ser Ile Ser Ile
145                 150                 155                 160

Ala Thr Ala Cys Thr Ser Gly Val His Asn Ile Gly His Ala Ala Arg
                165                 170                 175

Ile Ile Ala Tyr Gly Asp Ala Asp Val Met Val Ala Gly Gly Ala Glu
            180                 185                 190

Lys Ala Ser Thr Pro Leu Gly Val Gly Gly Phe Gly Ala Ala Arg Ala
        195                 200                 205

Leu Ser Thr Arg Asn Asp Asn Pro Gln Ala Ala Ser Arg Pro Trp Asp
210                 215                 220

Lys Glu Arg Asp Gly Phe Val Leu Gly Asp Gly Ala Gly Met Leu Val
225                 230                 235                 240

Leu Glu Glu Tyr Glu His Ala Lys Lys Arg Gly Ala Lys Ile Tyr Ala
                245                 250                 255

Glu Leu Val Gly Phe Gly Met Ser Ser Asp Ala Tyr His Met Thr Ser
            260                 265                 270

Pro Pro Glu Asn Gly Ala Gly Ala Ala Leu Ala Met Ala Asn Ala Leu
        275                 280                 285

Arg Asp Ala Gly Ile Glu Ala Ser Gln Ile Gly Tyr Val Asn Ala His
290                 295                 300

Gly Thr Ser Thr Pro Ala Gly Asp Lys Ala Glu Ala Gln Ala Val Lys
305                 310                 315                 320

Thr Ile Phe Gly Glu Ala Ala Ser Arg Val Leu Val Ser Ser Thr Lys
                325                 330                 335

Ser Met Thr Gly His Leu Leu Gly Ala Ala Gly Ala Val Glu Ser Ile
            340                 345                 350

Tyr Ser Ile Leu Ala Leu Arg Asp Gln Ala Val Pro Pro Thr Ile Asn
        355                 360                 365

Leu Asp Asn Pro Asp Glu Gly Cys Asp Leu Asp Phe Val Pro His Glu
370                 375                 380

Ala Arg Gln Val Ser Gly Met Glu Tyr Thr Leu Cys Asn Ser Phe Gly
```

```
385                 390                 395                 400
Phe Gly Gly Thr Asn Gly Ser Leu Ile Phe Lys Lys Ile
                405                 410
```

<210> SEQ ID NO 15
<211> LENGTH: 720
<212> TYPE: DNA
<213> ORGANISM: Escherichia coli

<400> SEQUENCE: 15

```
atggtcatta aggcgcaaag cccggcgggt tcgcggaag agtacattat tgaaagtatc      60
tggaataacc gcttccctcc cgggactatt tgcccgcag aacgtgaact ttcagaatta    120
attggcgtaa cgcgtactac gttacgtgaa gtgttacagc gtctggcacg agatggctgg   180
ttgaccattc aacatggcaa gccgacgaag gtgaataatt tctgggaaac ttccggttta   240
aatatccttg aaacactggc gcgactggat cacgaaagtg tgccgcagct tattgataat   300
ttgctgtcgg tgcgtaccaa tatttccact attttattc gcaccgcgtt tcgtcagcat   360
cccgataaag cgcaggaagt gctggctacc gctaatgaag tggccgatca cgccgatgcc   420
tttgccgagc tggattacaa catattccgc ggcctggcgt tgcttccgg caacccgatt   480
tacggtctga ttcttaacgg gatgaaaggg ctgtatacgc gtattggtcg tcactatttc   540
gccaatccgg aagcgcgcag tctggcgctg ggcttctacc acaaactgtc ggcgttgtgc   600
agtgaaggcg cgcacgatca ggtgtacgaa acagtgcgtc gctatgggca tgagagtggc   660
gagatttggc accggatgca gaaaaatctg ccgggtgatt tagccattca ggggcgataa   720
```

<210> SEQ ID NO 16
<211> LENGTH: 239
<212> TYPE: PRT
<213> ORGANISM: Escherichia coli

<400> SEQUENCE: 16

```
Met Val Ile Lys Ala Gln Ser Pro Ala Gly Phe Ala Glu Glu Tyr Ile
1               5                   10                  15

Ile Glu Ser Ile Trp Asn Asn Arg Phe Pro Pro Gly Thr Ile Leu Pro
            20                  25                  30

Ala Glu Arg Glu Leu Ser Glu Leu Ile Gly Val Thr Arg Thr Thr Leu
        35                  40                  45

Arg Glu Val Leu Gln Arg Leu Ala Arg Asp Gly Trp Leu Thr Ile Gln
    50                  55                  60

His Gly Lys Pro Thr Lys Val Asn Asn Phe Trp Glu Thr Ser Gly Leu
65                  70                  75                  80

Asn Ile Leu Glu Thr Leu Ala Arg Leu Asp His Glu Ser Val Pro Gln
                85                  90                  95

Leu Ile Asp Asn Leu Leu Ser Val Arg Thr Asn Ile Ser Thr Ile Phe
            100                 105                 110

Ile Arg Thr Ala Phe Arg Gln His Pro Asp Lys Ala Gln Glu Val Leu
        115                 120                 125

Ala Thr Ala Asn Glu Val Ala Asp His Ala Asp Ala Phe Ala Glu Leu
    130                 135                 140

Asp Tyr Asn Ile Phe Arg Gly Leu Ala Phe Ala Ser Gly Asn Pro Ile
145                 150                 155                 160

Tyr Gly Leu Ile Leu Asn Gly Met Lys Gly Leu Tyr Thr Arg Ile Gly
                165                 170                 175

Arg His Tyr Phe Ala Asn Pro Glu Ala Arg Ser Leu Ala Leu Gly Phe
```

```
                    180              185                  190
Tyr His Lys Leu Ser Ala Leu Cys Ser Glu Gly Ala His Asp Gln Val
        195                  200                  205

Tyr Glu Thr Val Arg Arg Tyr Gly His Glu Ser Gly Glu Ile Trp His
        210                  215                  220

Arg Met Gln Lys Asn Leu Pro Gly Asp Leu Ala Ile Gln Gly Arg
225                  230                  235

<210> SEQ ID NO 17
<211> LENGTH: 1542
<212> TYPE: DNA
<213> ORGANISM: Artificial Sequence
<220> FEATURE:
<223> OTHER INFORMATION: Synthetic polynucleotide for codon optimized
      FAR from Marinobacter aquaeolei

<400> SEQUENCE: 17
atggctatcc agcaggttca tcacgccgac acatcctcct ctaaagtcct gggtcaactt     60
cgtggtaaac gtgtcttgat taccggcact actggattct tgggtaaagt cgtcttggaa   120
cgtttgattc gtgccgttcc tgacatcggt gctatctacc tgctgattcg tggtaacaag   180
cgtcacccgg atgctcgttc cgtttcttg gaggagattg ctacctcctc tgtctttgat   240
cgtttgcgtg aagctgattc cgaaggtttc gatgctttcc tggaagaacg tattcactgt   300
gttactggta agttactga agctggtttc ggtattggtc aagaggacta tcgtaagttg   360
gccaccgaat tggacgcagt catcaattct gctgcctccg tcaacttccg tgaggagttg   420
gataaggctc tggccatcaa cactctgtgt ttgcgtaaca tcgctggtat ggtggatctt   480
aaccctaagc tggccgttct tcaagtctct acgtgttacg tcaacggtat gaactctggt   540
caagttactg aatccgtcat caaaccagct ggtgaagctg ttcctcgttc tcctgatgga   600
ttctacgaga tcgaggaatt ggttcgtctg ctgcaagaca agattgaaga cgttcaagca   660
cgttactctg gtaaggtgtt ggagcgtaag ttggttgatt tgggtattcg tgaggctaat   720
cgttacggtt ggtctgatac atacaccttc acgaaatggt tgggtgaaca acttctgatg   780
aaagccttga tggtcgtac cttgactatt ctgcgtccta gcatcattga atctgctttg   840
gaagaaccag cacctggttg gattgaaggc gtgaaagttg cagatgcgat catcttggct   900
tatgctcgtg agaaggttac tttgtttccg ggtaaacgtt ctggtatcat gatgtgatt   960 cctgttgact tggttgccaa ttccatcatc ttgtctttgg ctgaggctct gggcgaacct  1020
ggtcgtcgtc gtatctacca atgttgttct ggtggtggta atcctatctc cctgggcgag  1080
ttcattgatc acctgatggc tgaatccaaa gccaactatg ccgcatacga tcatctgttc  1140
taccgtcaac cctccaagcc tttccttgct gtcaaccgtg ctttgttcga cttggttatc  1200
tctggtgtcc gtctgccttt gtctttgacc gaccgtgtct tgaagctgct gggcaactcc  1260
cgtgacctga gatgctgcg taacctggat actacgcaat ccctggctac tatctttggc  1320
ttctacacag cccccgacta catcttccgt aatgacgagt tgatggccct ggctaaccgt  1380
atgggcgagg ttgataaggg tttgttcccc gttgatgctc gtctgattga ttgggaattg  1440
tacctgcgta agattcacct ggctggtttg aaccgttacg ccttgaagga gcgtaaggtt  1500
tactctttga agacagcccg tcagcgtaag aaggcagctt aa                     1542

<210> SEQ ID NO 18
<211> LENGTH: 513
<212> TYPE: PRT
<213> ORGANISM: Artificial Sequence
```

<220> FEATURE:
<223> OTHER INFORMATION: Synthetic polypeptide encoded by SEQ ID NO:17

<400> SEQUENCE: 18

```
Met Ala Ile Gln Gln Val His His Ala Asp Thr Ser Ser Lys Val
1               5                   10                  15

Leu Gly Gln Leu Arg Gly Lys Arg Val Leu Ile Thr Gly Thr Gly
                20                  25                  30

Phe Leu Gly Lys Val Val Leu Glu Arg Leu Ile Arg Ala Val Pro Asp
            35                  40                  45

Ile Gly Ala Ile Tyr Leu Leu Ile Arg Gly Asn Lys Arg His Pro Asp
        50                  55                  60

Ala Arg Ser Arg Phe Leu Glu Glu Ile Ala Thr Ser Ser Val Phe Asp
65                  70                  75                  80

Arg Leu Arg Glu Ala Asp Ser Glu Gly Phe Asp Ala Phe Leu Glu Glu
                85                  90                  95

Arg Ile His Cys Val Thr Gly Glu Val Thr Glu Ala Gly Phe Gly Ile
                100                 105                 110

Gly Gln Glu Asp Tyr Arg Lys Leu Ala Thr Glu Leu Asp Ala Val Ile
            115                 120                 125

Asn Ser Ala Ala Ser Val Asn Phe Arg Glu Glu Leu Asp Lys Ala Leu
130                 135                 140

Ala Ile Asn Thr Leu Cys Leu Arg Asn Ile Ala Gly Met Val Asp Leu
145                 150                 155                 160

Asn Pro Lys Leu Ala Val Leu Gln Val Ser Thr Cys Tyr Val Asn Gly
                165                 170                 175

Met Asn Ser Gly Gln Val Thr Glu Ser Val Ile Lys Pro Ala Gly Glu
            180                 185                 190

Ala Val Pro Arg Ser Pro Asp Gly Phe Tyr Glu Ile Glu Glu Leu Val
                195                 200                 205

Arg Leu Leu Gln Asp Lys Ile Glu Asp Val Gln Ala Arg Tyr Ser Gly
            210                 215                 220

Lys Val Leu Glu Arg Lys Leu Val Asp Leu Gly Ile Arg Glu Ala Asn
225                 230                 235                 240

Arg Tyr Gly Trp Ser Asp Thr Tyr Thr Phe Thr Lys Trp Leu Gly Glu
                245                 250                 255

Gln Leu Leu Met Lys Ala Leu Asn Gly Arg Thr Leu Thr Ile Leu Arg
            260                 265                 270

Pro Ser Ile Ile Glu Ser Ala Leu Glu Glu Pro Ala Pro Gly Trp Ile
        275                 280                 285

Glu Gly Val Lys Val Ala Asp Ala Ile Ile Leu Ala Tyr Ala Arg Glu
    290                 295                 300

Lys Val Thr Leu Phe Pro Gly Lys Arg Ser Gly Ile Ile Asp Val Ile
305                 310                 315                 320

Pro Val Asp Leu Val Ala Asn Ser Ile Ile Leu Ser Leu Ala Glu Ala
                325                 330                 335

Leu Gly Glu Pro Gly Arg Arg Ile Tyr Gln Cys Cys Ser Gly Gly
            340                 345                 350

Gly Asn Pro Ile Ser Leu Gly Glu Phe Ile Asp His Leu Met Ala Glu
        355                 360                 365

Ser Lys Ala Asn Tyr Ala Ala Tyr Asp His Leu Phe Tyr Arg Gln Pro
    370                 375                 380

Ser Lys Pro Phe Leu Ala Val Asn Arg Ala Leu Phe Asp Leu Val Ile
385                 390                 395                 400
```

```
Ser Gly Val Arg Leu Pro Leu Ser Leu Thr Asp Arg Val Leu Lys Leu
            405                 410                 415

Leu Gly Asn Ser Arg Asp Leu Lys Met Leu Arg Asn Leu Asp Thr Thr
        420                 425                 430

Gln Ser Leu Ala Thr Ile Phe Gly Phe Tyr Thr Ala Pro Asp Tyr Ile
            435                 440                 445

Phe Arg Asn Asp Glu Leu Met Ala Leu Ala Asn Arg Met Gly Glu Val
        450                 455                 460

Asp Lys Gly Leu Phe Pro Val Asp Ala Arg Leu Ile Asp Trp Glu Leu
465                 470                 475                 480

Tyr Leu Arg Lys Ile His Leu Ala Gly Leu Asn Arg Tyr Ala Leu Lys
                485                 490                 495

Glu Arg Lys Val Tyr Ser Leu Lys Thr Ala Arg Gln Arg Lys Lys Ala
            500                 505                 510

Ala

<210> SEQ ID NO 19
<211> LENGTH: 1686
<212> TYPE: DNA
<213> ORGANISM: Escherichia coli

<400> SEQUENCE: 19
atgaagaagg tttggcttaa ccgttatccc gcggacgttc cgacggagat caaccctgac      60
cgttatcaat ctctggtaga tatgtttgag cagtcggtcg cgcgctacgc cgatcaacct     120
gcgtttgtga atatggggga ggtaatgacc ttccgcaagc tggaagaacg cagtcgcgcg     180
tttgccgctt atttgcaaca agggttgggg ctgaagaaag gcgatcgcgt tgcgttgatg     240
atgcctaatt tattgcaata tccggtggcg ctgtttggca ttttgcgtgc cgggatgatc     300
gtcgtaaacg ttaacccgtt gtataccccg cgtgagcttg agcatcagct taacgatagc     360
ggcgcatcgg cgattgttat cgtgtctaac tttgctcaca cactggaaaa agtggttgat     420
aaaaccgccg ttcagcacgt aattctgacc cgtatgggcg atcagctatc tacggcaaaa     480
ggcacggtag tcaatttcgt tgttaaatac atcaagcgtt tggtgccgaa ataccatctg     540
ccagatgcca tttcatttcg tagcgcactg cataacggct accggatgca gtacgtcaaa     600
cccgaactgg tgccggaaga tttagctttt ctgcaataca ccggcggcac cactggtgtg     660
gcgaaaggcg cgatgctgac tcaccgcaat atgctggcga actggaacag gttaacgcg      720 acctatggtc cgctgttgca tccgggcaaa gagctggtgg tgacggcgct gccgctgtat     780 cacattttg ccctgaccat taactgcctg ctgtttatcg aactgggtgg gcagaacctg     840
cttatcacta cccgcgcga tattccaggg ttggtaaaag agttagcgaa atatccgttt     900
accgctatca cgggcgttaa caccttgttc aatgcgttgc tgaacaataa agagttccag     960
cagctggatt ctccagtct gcatctttcc gcaggcggtg ggatgccagt gcagcaagtg    1020
gtggcagagc gttgggtgaa actgaccgga cagtatctgc tggaaggcta tggccttacc    1080
gagtgtgcgc cgctggtcag cgttaaccca tatgatattg attatcatag tggtagcatc    1140
ggtttgccgg tgccgtcgac ggaagccaaa ctggtggatg atgatgataa tgaagtacca    1200
ccaggtcaac cgggtgagct tgtgtcaaa ggaccgcagg tgatgctggg ttactggcag    1260
cgtcccgatg ctaccgatga atcatcaaa aatggctggt tacacaccgg cgacatcgcg    1320
gtaatggatg aagaaggatt cctgcgcatt gtcgatcgta aaaagacat gattctggtt    1380 tccggtttta acgtctatcc caacgagatt gaagatgtcg tcatgcagca tcctggcgta    1440
```

```
caggaagtcg cggctgttgg cgtaccttcc ggctccagtg gtgaagcggt gaaatcttc    1500 gtagtgaaaa aagatccatc gcttaccgaa gagtcactgg tgacttttg ccgccgtcag    1560 ctcacgggat acaaagtacc gaagctggtg gagtttcgtg atgagttacc gaaatctaac   1620
gtcggaaaaa ttttgcgacg agaattacgt gacgaagcgc gcggcaaagt ggacaataaa   1680
gcctaa                                                              1686
```

```
<210> SEQ ID NO 20
<211> LENGTH: 561
<212> TYPE: PRT
<213> ORGANISM: Escherichia coli

<400> SEQUENCE: 20

Met Lys Lys Val Trp Leu Asn Arg Tyr Pro Ala Asp Val Pro Thr Glu
1               5                   10                  15

Ile Asn Pro Asp Arg Tyr Gln Ser Leu Val Asp Met Phe Glu Gln Ser
            20                  25                  30

Val Ala Arg Tyr Ala Asp Gln Pro Ala Phe Val Asn Met Gly Glu Val
        35                  40                  45

Met Thr Phe Arg Lys Leu Glu Glu Arg Ser Arg Ala Phe Ala Ala Tyr
    50                  55                  60

Leu Gln Gln Gly Leu Gly Leu Lys Lys Gly Asp Arg Val Ala Leu Met
65                  70                  75                  80

Met Pro Asn Leu Leu Gln Tyr Pro Val Ala Leu Phe Gly Ile Leu Arg
                85                  90                  95

Ala Gly Met Ile Val Val Asn Val Asn Pro Leu Tyr Thr Pro Arg Glu
            100                 105                 110

Leu Glu His Gln Leu Asn Asp Ser Gly Ala Ser Ala Ile Val Ile Val
        115                 120                 125

Ser Asn Phe Ala His Thr Leu Glu Lys Val Val Asp Lys Thr Ala Val
130                 135                 140

Gln His Val Ile Leu Thr Arg Met Gly Asp Gln Leu Ser Thr Ala Lys
145                 150                 155                 160

Gly Thr Val Val Asn Phe Val Val Lys Tyr Ile Lys Arg Leu Val Pro
                165                 170                 175

Lys Tyr His Leu Pro Asp Ala Ile Ser Phe Arg Ser Ala Leu His Asn
            180                 185                 190

Gly Tyr Arg Met Gln Tyr Val Lys Pro Glu Leu Val Pro Glu Asp Leu
        195                 200                 205

Ala Phe Leu Gln Tyr Thr Gly Gly Thr Thr Gly Val Ala Lys Gly Ala
    210                 215                 220

Met Leu Thr His Arg Asn Met Leu Ala Asn Leu Glu Gln Val Asn Ala
225                 230                 235                 240

Thr Tyr Gly Pro Leu Leu His Pro Gly Lys Glu Leu Val Val Thr Ala
                245                 250                 255

Leu Pro Leu Tyr His Ile Phe Ala Leu Thr Ile Asn Cys Leu Leu Phe
            260                 265                 270

Ile Glu Leu Gly Gly Gln Asn Leu Leu Ile Thr Asn Pro Arg Asp Ile
        275                 280                 285

Pro Gly Leu Val Lys Glu Leu Ala Lys Tyr Pro Phe Thr Ala Ile Thr
    290                 295                 300

Gly Val Asn Thr Leu Phe Asn Ala Leu Leu Asn Asn Lys Glu Phe Gln
305                 310                 315                 320
```

```
Gln Leu Asp Phe Ser Ser Leu His Leu Ser Ala Gly Gly Gly Met Pro
                325                 330                 335
Val Gln Gln Val Val Ala Glu Arg Trp Val Lys Leu Thr Gly Gln Tyr
            340                 345                 350
Leu Leu Glu Gly Tyr Gly Leu Thr Glu Cys Ala Pro Leu Val Ser Val
        355                 360                 365
Asn Pro Tyr Asp Ile Asp Tyr His Ser Gly Ser Ile Gly Leu Pro Val
    370                 375                 380
Pro Ser Thr Glu Ala Lys Leu Val Asp Asp Asp Asn Glu Val Pro
385                 390                 395                 400
Pro Gly Gln Pro Gly Glu Leu Cys Val Lys Gly Pro Gln Val Met Leu
                405                 410                 415
Gly Tyr Trp Gln Arg Pro Asp Ala Thr Asp Glu Ile Ile Lys Asn Gly
            420                 425                 430
Trp Leu His Thr Gly Asp Ile Ala Val Met Asp Glu Glu Gly Phe Leu
        435                 440                 445
Arg Ile Val Asp Arg Lys Lys Asp Met Ile Leu Val Ser Gly Phe Asn
    450                 455                 460
Val Tyr Pro Asn Glu Ile Glu Asp Val Val Met Gln His Pro Gly Val
465                 470                 475                 480
Gln Glu Val Ala Ala Val Gly Val Pro Ser Gly Ser Ser Gly Glu Ala
                485                 490                 495
Val Lys Ile Phe Val Val Lys Lys Asp Pro Ser Leu Thr Glu Glu Ser
            500                 505                 510
Leu Val Thr Phe Cys Arg Arg Gln Leu Thr Gly Tyr Lys Val Pro Lys
        515                 520                 525
Leu Val Glu Phe Arg Asp Glu Leu Pro Lys Ser Asn Val Gly Lys Ile
    530                 535                 540
Leu Arg Arg Glu Leu Arg Asp Glu Ala Arg Gly Lys Val Asp Asn Lys
545                 550                 555                 560
Ala
```

<210> SEQ ID NO 21
<211> LENGTH: 981
<212> TYPE: DNA
<213> ORGANISM: Artificial Sequence
<220> FEATURE:
<223> OTHER INFORMATION: Synthetic polynucleotide encoding BTE
      thioesterase

<400> SEQUENCE: 21

| | | |
|---|---|---|
| atgacaatga ttacgccgag ctctgaactc acccttacga aagggaataa aagctggtca | 60 |
| tcgacagctg tagctgccgc tttagagtgg aaaccaaaac cgaaattacc tcagcttctt | 120 |
| gacgaccact tcggcctgca tggtttagta ttccgcagaa cgtttgccat aagaagctac | 180 |
| gaagtaggac cagatcgttc tacctctata cttgctgtga tgaatcatat gcaggaagcc | 240 |
| acgttaaatc acgcaaagag cgtcgggatc cttggggacg gattcggcac acattggaa | 300 |
| atgagtaagc gggacctgat gtgggttgtt cgtcgtaccc acgtagcggt cgaacggtat | 360 |
| ccaacatggg gcgatactgt tgaagtggag tgctggattg cgcttccgg aaacaacgga | 420 |
| atgcgcagag attttctggt gcgggactgt aaaactgggg aaatcttaac gcgctgtacc | 480 |
| tccctgtccg ttctgatgaa cacgcgtacc cggagattaa gtacgattcc ggacgaagtc | 540 |
| cgtggtgaaa tcggtcccgc ttttattgac aacgtggcgg taaagacga cgagatcaaa | 600 |
| aagttgcaga aattgaacga ttccacagca gattacatac agggcggtct tacgccccgt | 660 |

```
tggaacgact tggatgtgaa tcagcacgta aataaccta aatatgtggc gtgggtgttc      720
gagaccgttc ccgactctat ttttgaaagt caccacattt ccagctttac gctggagtac      780
agacgcgagt gtacgcgcga ttccgtttta cgttccctca ccacggtgtc tggcggatct      840
tccgaagctg ggttagtgtg tgatcacttg ctgcaacttg aaggcggaag tgaagttctt      900
cgggcccgca cggaatggcg tcccaaactg accgattcct tccgcggaat atcagtaatt      960
ccggccgagc cgcgggtata a                                                981

<210> SEQ ID NO 22
<211> LENGTH: 326
<212> TYPE: PRT
<213> ORGANISM: Artificial Sequence
<220> FEATURE:
<223> OTHER INFORMATION: Synthetic polypeptide encoded by SEQ ID NO:21

<400> SEQUENCE: 22
```

Met Thr Met Ile Thr Pro Ser Ser Glu Leu Thr Leu Thr Lys Gly Asn
1               5                   10                  15

Lys Ser Trp Ser Ser Thr Ala Val Ala Ala Leu Glu Trp Lys Pro
            20                  25                  30

Lys Pro Lys Leu Pro Gln Leu Leu Asp Asp His Phe Gly Leu His Gly
        35                  40                  45

Leu Val Phe Arg Arg Thr Phe Ala Ile Arg Ser Tyr Glu Val Gly Pro
    50                  55                  60

Asp Arg Ser Thr Ser Ile Leu Ala Val Met Asn His Met Gln Glu Ala
65                  70                  75                  80

Thr Leu Asn His Ala Lys Ser Val Gly Ile Leu Gly Asp Gly Phe Gly
                85                  90                  95

Thr Thr Leu Glu Met Ser Lys Arg Asp Leu Met Trp Val Val Arg Arg
            100                 105                 110

Thr His Val Ala Val Glu Arg Tyr Pro Thr Trp Gly Asp Thr Val Glu
        115                 120                 125

Val Glu Cys Trp Ile Gly Ala Ser Gly Asn Asn Gly Met Arg Arg Asp
    130                 135                 140

Phe Leu Val Arg Asp Cys Lys Thr Gly Glu Ile Leu Thr Arg Cys Thr
145                 150                 155                 160

Ser Leu Ser Val Leu Met Asn Thr Arg Thr Arg Arg Leu Ser Thr Ile
                165                 170                 175

Pro Asp Glu Val Arg Gly Glu Ile Gly Pro Ala Phe Ile Asp Asn Val
            180                 185                 190

Ala Val Lys Asp Asp Glu Ile Lys Lys Leu Gln Lys Leu Asn Asp Ser
        195                 200                 205

Thr Ala Asp Tyr Ile Gln Gly Gly Leu Thr Pro Arg Trp Asn Asp Leu
    210                 215                 220

Asp Val Asn Gln His Val Asn Asn Leu Lys Tyr Val Ala Trp Val Phe
225                 230                 235                 240

Glu Thr Val Pro Asp Ser Ile Phe Glu Ser His His Ile Ser Ser Phe
                245                 250                 255

Thr Leu Glu Tyr Arg Arg Glu Cys Thr Arg Asp Ser Val Leu Arg Ser
            260                 265                 270

Leu Thr Thr Val Ser Gly Gly Ser Ser Glu Ala Gly Leu Val Cys Asp
        275                 280                 285

His Leu Leu Gln Leu Glu Gly Gly Ser Glu Val Leu Arg Ala Arg Thr
    290                 295                 300

```
Glu Trp Arg Pro Lys Leu Thr Asp Ser Phe Arg Gly Ile Ser Val Ile
305                 310                 315                 320

Pro Ala Glu Pro Arg Val
                325

<210> SEQ ID NO 23
<211> LENGTH: 2445
<212> TYPE: DNA
<213> ORGANISM: Escherichia coli

<400> SEQUENCE: 23
atgatgattt tgagtattct cgctacggtt gtcctgctcg gcgcgttgtt ctatcaccgc      60
gtgagcttat ttatcagcag tctgattttg ctcgcctgga cagccgccct cggcgttgct     120
ggtctgtgtt cggcgtgggt actggtgcct ctggccatta tcctcgtgcc atttaacttt     180
gcgcctatgc gtaagtcgat gatttccgcg ccggtatttc gcggtttccg taaggtgatg     240
ccgccgatgt cgcgcactga gaaagaagcg attgatgcgg caccacctg tgggagggc      300 gacttgttcc agggcaagcc ggactggaaa aagctgcata actatccgca gccgcgcctg     360
accgccgaag agcaagcgtt tctcgacggc ccggtagaag aagcctgccg gatggcgaat     420
gatttccaga tcacccatga gctggcggat ctgccgccgg agttgtgggc gtaccttaaa     480
gagcatcgtt tcttcgcgat gatcatcaaa aaagagtacg gcgggctgga gttctcgggct    540 tatgcccagt ctcgcgtgct gcaaaaactc tccggcgtga gcgggatcct ggcgattacc     600
gtcggcgtgc caaactcatt aggcccgggc gaactgttgc aacattacgg cactgacgag     660
cagaaagatc actatctgcc gcgtctggcg cgtggtcagg agatcccctg ctttgcactg     720
accagcccgg aagcgggttc cgatgcgggc gcgattccgg acaccgggat tgtctgcatg     780
ggcgaatggc agggccagca ggtgctgggg atgcgtctga cctggaacaa acgctacatt     840
acgctggcac cgattgcgac cgtgcttggg ctggcgttta aactctccga cccggaaaaa     900
ttactcggcg gtgcagaaga tttaggcatt acctgtgcgc tgatcccaac caccacgccg     960
ggcgtggaaa ttggtcgtcg ccacttcccg ctgaacgtac cgttccagaa cggaccgacg    1020
cgcggtaaag atgtcttcgt gccgatcgat tacatcatcg gcgggccgaa aatggccggg    1080
caaggctggc ggatgctggt ggagtgcctc tcggtaggcc gcggcatcac cctgccttcc    1140
aactcaaccg gcgcgtgaa atcggtagcg ctggcaaccg gcgcgtatgc tcacattcgc    1200
cgtcagttca aaatctctat tggtaagatg gaagggattg aagagccgct ggcgcgtatt     1260
gccggtaatg cctacgtgat ggatgctgcg gcatcgctga ttacctacgg cattatgctc     1320
ggcgaaaaac ctgccgtgct gtcggctatc gttaagtatc actgtaccca cgcgggcag     1380 cagtcgatta tgatgcgat ggatattacc ggcggtaaag gcattatgct cgggcaaagc     1440
aacttcctgg cgcgtgctta ccagggcgca ccgattgcca tcaccgttga agggctaac     1500 attctgaccc gcagcatgat gatcttcgga caaggagcg ttcgttgcca tccgtacgtg     1560
ctggaagaga tggaagcggc gaagaacaat gacgtcaacg cgttcgataa actgttgttc     1620
aaacatatcg gtcacgtcgg tagcaacaaa gttcgcagct tctggctggg cctgacgcgc     1680
ggtttaacca gcagcacgcc aaccggcgat gccactaaac gctactatca gcacctgaac     1740
cgcctgagcg ccaacctcgc cctgctttct gatgtctcga tggcagtgct gggcggcagc     1800
ctgaaacgtc gcgagcgcat ctcggcccgt ctggggata ttttaagcca gctctacctc     1860
gcctctgccg tgctgaagcg ttatgacgac gaaggccgta atgaagccga cctgccgctg     1920
```

-continued

```
gtgcactggg gcgtacaaga tgcgctgtat caggctgaac aggcgatgga tgatttactg    1980
caaaacttcc cgaaccgcgt ggttgccggg ctgctgaatg tggtgatctt cccgaccgga    2040
cgtcattatc tggcaccttc tgacaagctg gatcataaag tggcgaagat tttacaagtg    2100
ccgaacgcca cccgttcccg cattggtcgc ggtcagtacc tgacgccgag cgagcataat    2160
ccggttggct tgctggaaga ggcgctggtg gatgtgattg ccgccgaccc aattcatcag    2220
cggatctgta aagagctggg taaaaacctg ccgtttaccc gtctggatga actggcgcac    2280
aacgcgctgg tgaaggggct gattgataaa gatgaagccg ctattctggt gaaagctgaa    2340
gaaagccgtc tgcgcagtat taacgttgat gactttgatc cggaagagct ggcgacgaag    2400
ccggtaaagt tgccggagaa agtgcggaaa gttgaagccg cgtaa                    2445
```

<210> SEQ ID NO 24
<211> LENGTH: 814
<212> TYPE: PRT
<213> ORGANISM: Escherichia coli

<400> SEQUENCE: 24

```
Met Met Ile Leu Ser Ile Leu Ala Thr Val Val Leu Gly Ala Leu
1               5                   10                  15

Phe Tyr His Arg Val Ser Leu Phe Ile Ser Ser Leu Ile Leu Leu Ala
                20                  25                  30

Trp Thr Ala Ala Leu Gly Val Ala Gly Leu Trp Ser Ala Trp Val Leu
            35                  40                  45

Val Pro Leu Ala Ile Ile Leu Val Pro Phe Asn Phe Ala Pro Met Arg
        50                  55                  60

Lys Ser Met Ile Ser Ala Pro Val Phe Arg Gly Phe Arg Lys Val Met
65                  70                  75                  80

Pro Pro Met Ser Arg Thr Glu Lys Glu Ala Ile Asp Ala Gly Thr Thr
                85                  90                  95

Trp Trp Glu Gly Asp Leu Phe Gln Gly Lys Pro Asp Trp Lys Lys Leu
            100                 105                 110

His Asn Tyr Pro Gln Pro Arg Leu Thr Ala Glu Glu Gln Ala Phe Leu
        115                 120                 125

Asp Gly Pro Val Glu Glu Ala Cys Arg Met Ala Asn Asp Phe Gln Ile
    130                 135                 140

Thr His Glu Leu Ala Asp Leu Pro Pro Glu Leu Trp Ala Tyr Leu Lys
145                 150                 155                 160

Glu His Arg Phe Phe Ala Met Ile Ile Lys Lys Glu Tyr Gly Gly Leu
                165                 170                 175

Glu Phe Ser Ala Tyr Ala Gln Ser Arg Val Leu Gln Lys Leu Ser Gly
            180                 185                 190

Val Ser Gly Ile Leu Ala Ile Thr Val Gly Val Pro Asn Ser Leu Gly
        195                 200                 205

Pro Gly Glu Leu Leu Gln His Tyr Gly Thr Asp Glu Gln Lys Asp His
    210                 215                 220

Tyr Leu Pro Arg Leu Ala Arg Gly Gln Glu Ile Pro Cys Phe Ala Leu
225                 230                 235                 240

Thr Ser Pro Glu Ala Gly Ser Asp Ala Gly Ala Ile Pro Asp Thr Gly
                245                 250                 255

Ile Val Cys Met Gly Glu Trp Gln Gly Gln Gln Val Leu Gly Met Arg
            260                 265                 270

Leu Thr Trp Asn Lys Arg Tyr Ile Thr Leu Ala Pro Ile Ala Thr Val
        275                 280                 285
```

```
Leu Gly Leu Ala Phe Lys Leu Ser Asp Pro Glu Lys Leu Gly Gly
    290                 295                 300

Ala Glu Asp Leu Gly Ile Thr Cys Ala Leu Ile Pro Thr Thr Thr Pro
305                 310                 315                 320

Gly Val Glu Ile Gly Arg Arg His Phe Pro Leu Asn Val Pro Phe Gln
                325                 330                 335

Asn Gly Pro Thr Arg Gly Lys Asp Val Phe Val Pro Ile Asp Tyr Ile
            340                 345                 350

Ile Gly Gly Pro Lys Met Ala Gly Gln Gly Trp Arg Met Leu Val Glu
        355                 360                 365

Cys Leu Ser Val Gly Arg Gly Ile Thr Leu Pro Ser Asn Ser Thr Gly
    370                 375                 380

Gly Val Lys Ser Val Ala Leu Ala Thr Gly Ala Tyr Ala His Ile Arg
385                 390                 395                 400

Arg Gln Phe Lys Ile Ser Ile Gly Lys Met Glu Gly Ile Glu Glu Pro
                405                 410                 415

Leu Ala Arg Ile Ala Gly Asn Ala Tyr Val Met Asp Ala Ala Ala Ser
            420                 425                 430

Leu Ile Thr Tyr Gly Ile Met Leu Gly Glu Lys Pro Ala Val Leu Ser
        435                 440                 445

Ala Ile Val Lys Tyr His Cys Thr His Arg Gly Gln Gln Ser Ile Ile
450                 455                 460

Asp Ala Met Asp Ile Thr Gly Gly Lys Gly Ile Met Leu Gly Gln Ser
465                 470                 475                 480

Asn Phe Leu Ala Arg Ala Tyr Gln Gly Ala Pro Ile Ala Ile Thr Val
                485                 490                 495

Glu Gly Ala Asn Ile Leu Thr Arg Ser Met Met Ile Phe Gly Gln Gly
            500                 505                 510

Ala Ile Arg Cys His Pro Tyr Val Leu Glu Glu Met Glu Ala Ala Lys
        515                 520                 525

Asn Asn Asp Val Asn Ala Phe Asp Lys Leu Leu Phe Lys His Ile Gly
    530                 535                 540

His Val Gly Ser Asn Lys Val Arg Ser Phe Trp Leu Gly Leu Thr Arg
545                 550                 555                 560

Gly Leu Thr Ser Ser Thr Pro Thr Gly Asp Ala Thr Lys Arg Tyr Tyr
                565                 570                 575

Gln His Leu Asn Arg Leu Ser Ala Asn Leu Ala Leu Leu Ser Asp Val
            580                 585                 590

Ser Met Ala Val Leu Gly Gly Ser Leu Lys Arg Arg Glu Arg Ile Ser
        595                 600                 605

Ala Arg Leu Gly Asp Ile Leu Ser Gln Leu Tyr Leu Ala Ser Ala Val
    610                 615                 620

Leu Lys Arg Tyr Asp Asp Glu Gly Arg Asn Glu Ala Asp Leu Pro Leu
625                 630                 635                 640

Val His Trp Gly Val Gln Asp Ala Leu Tyr Gln Ala Glu Gln Ala Met
                645                 650                 655

Asp Asp Leu Leu Gln Asn Phe Pro Asn Arg Val Val Ala Gly Leu Leu
            660                 665                 670

Asn Val Val Ile Phe Pro Thr Gly Arg His Tyr Leu Ala Pro Ser Asp
        675                 680                 685

Lys Leu Asp His Lys Val Ala Lys Ile Leu Gln Val Pro Asn Ala Thr
    690                 695                 700
```

```
Arg Ser Arg Ile Gly Arg Gly Gln Tyr Leu Thr Pro Ser Glu His Asn
705                 710                 715                 720

Pro Val Gly Leu Leu Glu Glu Ala Leu Asp Val Ile Ala Ala Asp
                725                 730                 735

Pro Ile His Gln Arg Ile Cys Lys Glu Leu Gly Lys Asn Leu Pro Phe
            740                 745                 750

Thr Arg Leu Asp Glu Leu Ala His Asn Ala Leu Val Lys Gly Leu Ile
        755                 760                 765

Asp Lys Asp Glu Ala Ala Ile Leu Val Lys Ala Glu Glu Ser Arg Leu
    770                 775                 780

Arg Ser Ile Asn Val Asp Asp Phe Asp Pro Glu Glu Leu Ala Thr Lys
785                 790                 795                 800

Pro Val Lys Leu Pro Glu Lys Val Arg Lys Val Glu Ala Ala
                805                 810
```

<210> SEQ ID NO 25
<211> LENGTH: 739
<212> TYPE: DNA
<213> ORGANISM: Rhodobacter capsulatus

<400> SEQUENCE: 25

```
tcggcatgaa agcggttgat gcgccggata ttgacgtagt cacgggtcgt aaagactaat    60
aagcttgagt ttaggaagag tatcatgtct gaaccggctc cgtacacctc ggctgatctg   120
tccctgatta aacgcattat ccgcaccgc tacccgtttc tgatggtcga taaagtgcgt    180
gatattgttc cgtttgaaag cgcggtcggt atcaaatgcg tgaccaacaa tgaaccgcag   240
tttacgggtc atttcccgga agaaccggtt atgccgggcg ttatgattgt cgaagcaatg   300
gctcaaaccg cggccgtggt tgtcggcatt tctatgaacg tgatcgataa accgctgggt   360
acctatttta tggcaatcga cggctgtaaa ttccgtcgca agtggttcc gggtgacgtt    420
ctggaaatgc acgtcaccgt gaaacgcggc ggtggcaaag tctggaaatt cctgggcgaa   480
agttttgtgg aaggtcaact ggctgctacg gctgaattta cggcaatgat ggatctgaaa   540
ggttaattgt ggaaggtcaa ctggctgcta cggctgaatt tacggcaatg atggatctga   600
aaggttaaga cgtctatgaa ttcgtttaaa cgccaggcat caaataaaac gaaaggctca   660
gtcgaaagac tgggcctttc gttttatctg ttgtttgtcg gtgaacgctc tcctgaggcg   720
cctgatgcgg tattttctc                                                739
```

<210> SEQ ID NO 26
<211> LENGTH: 153
<212> TYPE: PRT
<213> ORGANISM: Rhodobacter capsulatus

<400> SEQUENCE: 26

```
Met Ser Glu Pro Ala Pro Tyr Thr Ser Ala Asp Leu Ser Leu Ile Lys
1               5                   10                  15

Arg Ile Ile Pro His Arg Tyr Pro Phe Leu Met Val Asp Lys Val Arg
            20                  25                  30

Asp Ile Val Pro Phe Glu Ser Ala Val Gly Ile Lys Cys Val Thr Asn
        35                  40                  45

Asn Glu Pro Gln Phe Thr Gly His Phe Pro Glu Glu Pro Val Met Pro
    50                  55                  60

Gly Val Met Ile Val Glu Ala Met Ala Gln Thr Ala Ala Val Val Val
65                  70                  75                  80

Gly Ile Ser Met Asn Val Ile Asp Lys Pro Leu Gly Thr Tyr Phe Met
```

|  |  | 85 |  |  |  | 90 |  |  |  | 95 |  |
| --- | --- | --- | --- | --- | --- | --- | --- | --- | --- | --- | --- |
| Ala | Ile | Asp | Gly | Cys | Lys | Phe | Arg | Arg | Lys | Val | Val | Pro | Gly | Asp | Val |
|  |  |  | 100 |  |  |  |  | 105 |  |  |  |  | 110 |  |  |

| Leu | Glu | Met | His | Val | Thr | Val | Lys | Arg | Gly | Gly | Gly | Lys | Val | Trp | Lys |
| --- | --- | --- | --- | --- | --- | --- | --- | --- | --- | --- | --- | --- | --- | --- | --- |
|  |  |  | 115 |  |  |  |  | 120 |  |  |  |  | 125 |  |  |

| Phe | Leu | Gly | Glu | Ser | Phe | Val | Glu | Gly | Gln | Leu | Ala | Ala | Thr | Ala | Glu |
| --- | --- | --- | --- | --- | --- | --- | --- | --- | --- | --- | --- | --- | --- | --- | --- |
|  | 130 |  |  |  |  | 135 |  |  |  |  | 140 |  |  |  |  |

| Phe | Thr | Ala | Met | Met | Asp | Leu | Lys | Gly |
| --- | --- | --- | --- | --- | --- | --- | --- | --- |
| 145 |  |  |  | 150 |  |  |  |  |

<210> SEQ ID NO 27
<211> LENGTH: 1539
<212> TYPE: DNA
<213> ORGANISM: Artificial Sequence
<220> FEATURE:
<223> OTHER INFORMATION: Synthetic polynucleotide for variant FAR

<400> SEQUENCE: 27

| atggcgactc aacaacagaa caacggtgca tctgcatccg gcgtcttgga aattcttcgt | 60 |
| --- | --- |
| ggaaagcacg ttcttatcac aggtactacc ggattttttgg gcaaagtggt tctggaaaag | 120 |
| ttgattcgta ctgttccgga tattggaggt attcatctgc tgattcgtgg caataaacgt | 180 |
| catccagccg ctcgcgaacg tttcctgaac gaaattgcgt cctcctccgt cttcgaacgt | 240 |
| ttgcgtcacg atgataatga agccttcgag accttcttgg aagaacgtgt tcactgtatt | 300 |
| accggtgaga ttactgaatc ccgttttggt ttgacacctg agcgttttcg tgctttggcc | 360 |
| ggtcaggttg acgcttttat tcatagcgct gcaagcgtga actttcgtga gcaattggat | 420 |
| aaagccctga aaatcaacac cttgtgtctt gaaaatgttg ctgctcttgc agaattgaac | 480 |
| tccgctatgg cggtcattca ggtttccact tgttacgtta acggtaaaac ctccggtcaa | 540 |
| attaccgaat ccgtcattaa atcggctggc gaatccattc ccgttccac tgacggttac | 600 |
| tacgagatcg aagaattggt ccatctgttg caagacaaga tttccgatgt aaagctcgt | 660 |
| tactccggcc gtgttatggg gaaaaaattg gttgatttgg gtattcgtga ggccaataat | 720 |
| tacggatggt ccgacaccta cacattcacc aaatggttgg gtgaacaact gctgatgaag | 780 |
| gccttgtctg gtcgttcttt gactattgtg cgtccctcta ttattgagtc cgcttttgga | 840 |
| gaaccttccc ctggttggat cgaaggcgtt aaagttgccg atgccattat cttggcttat | 900 |
| gcccgtgaaa agttagccct gttccctgga aaacgttccg gcattattga tgttattcct | 960 |
| gtcgatttgg ttgcgaactc catcatcttg tctctggctg aggcgttgtc tggttctggt | 1020 |
| caacgtcgta tttatcaatg ttgcagcggt ggttctaatc aatctccct gggtaagttc | 1080 |
| attgattatt tgaacgccga ggctaagacc aactatgctg cctacgatca actgttttat | 1140 |
| cgtcgtccta ctaaaccttt cgtcgccgtg aaccgtaaat tgtttgacgt tgttgttggt | 1200 |
| gtcatgcgtg ttgtcctttc tattgcccgc aaagctatgc gtttggctgg tgtaaatcgt | 1260 |
| gagttgaaag tgcttaagaa ccttgatacg acccgtaaac ttgcaaccat ttttggcttc | 1320 |
| tatactgctc ccgactatat cttccgtaac gatagcttga tggccctggc tcagcgtatg | 1380 |
| ggtgaattgg atcgtgttct tttcccagtt gatgctcgtc aaattgattg gcagttgtac | 1440 |
| ttgtgtaaaa ttcatttgcg tggtctgaac cgttacgctt tgaaggaacg taaactgtat | 1500 |
| tcttcgcgtg ctgctgatac tgacgataaa accgcctaa | 1539 |

<210> SEQ ID NO 28
<211> LENGTH: 512

```
<212> TYPE: PRT
<213> ORGANISM: Artificial Sequence
<220> FEATURE:
<223> OTHER INFORMATION: Synthetic polypeptide for Variant FAR

<400> SEQUENCE: 28
```

| | | | | | | | | | | | | | | |
|---|---|---|---|---|---|---|---|---|---|---|---|---|---|---|
| Met | Ala | Thr | Gln | Gln | Gln | Asn | Asn | Gly | Ala | Ser | Ala | Ser | Gly | Val | Leu |
| 1 | | | | 5 | | | | | 10 | | | | | 15 | |
| Glu | Ile | Leu | Arg | Gly | Lys | His | Val | Leu | Ile | Thr | Gly | Thr | Thr | Gly | Phe |
| | | | 20 | | | | | 25 | | | | | 30 | | |
| Leu | Gly | Lys | Val | Val | Leu | Glu | Lys | Leu | Ile | Arg | Thr | Val | Pro | Asp | Ile |
| | | 35 | | | | | 40 | | | | | 45 | | | |
| Gly | Gly | Ile | His | Leu | Leu | Ile | Arg | Gly | Asn | Lys | Arg | His | Pro | Ala | Ala |
| | 50 | | | | | 55 | | | | | 60 | | | | |
| Arg | Glu | Arg | Phe | Leu | Asn | Glu | Ile | Ala | Ser | Ser | Val | Phe | Glu | Arg |
| 65 | | | | | 70 | | | | | 75 | | | | | 80 |
| Leu | Arg | His | Asp | Asp | Asn | Glu | Ala | Phe | Glu | Thr | Phe | Leu | Glu | Glu | Arg |
| | | | | 85 | | | | | 90 | | | | | 95 | |
| Val | His | Cys | Ile | Thr | Gly | Glu | Ile | Thr | Glu | Ser | Arg | Phe | Gly | Leu | Thr |
| | | | 100 | | | | | 105 | | | | | 110 | | |
| Pro | Glu | Arg | Phe | Arg | Ala | Leu | Ala | Gly | Gln | Val | Asp | Ala | Phe | Ile | His |
| | | | 115 | | | | | 120 | | | | | 125 | | |
| Ser | Ala | Ala | Ser | Val | Asn | Phe | Arg | Glu | Gln | Leu | Asp | Lys | Ala | Leu | Lys |
| | 130 | | | | | 135 | | | | | 140 | | | | |
| Ile | Asn | Thr | Leu | Cys | Leu | Glu | Asn | Val | Ala | Ala | Leu | Ala | Glu | Leu | Asn |
| 145 | | | | | 150 | | | | | 155 | | | | | 160 |
| Ser | Ala | Met | Ala | Val | Ile | Gln | Val | Ser | Thr | Cys | Tyr | Val | Asn | Gly | Lys |
| | | | | 165 | | | | | 170 | | | | | 175 | |
| Thr | Ser | Gly | Gln | Ile | Thr | Glu | Ser | Val | Ile | Lys | Ser | Ala | Gly | Glu | Ser |
| | | | 180 | | | | | 185 | | | | | 190 | | |
| Ile | Pro | Arg | Ser | Thr | Asp | Gly | Tyr | Tyr | Glu | Ile | Glu | Glu | Leu | Val | His |
| | | | 195 | | | | | 200 | | | | | 205 | | |
| Leu | Leu | Gln | Asp | Lys | Ile | Ser | Asp | Val | Lys | Ala | Arg | Tyr | Ser | Gly | Arg |
| | 210 | | | | | 215 | | | | | 220 | | | | |
| Val | Met | Gly | Lys | Lys | Leu | Val | Asp | Leu | Gly | Ile | Arg | Glu | Ala | Asn | Asn |
| 225 | | | | | 230 | | | | | 235 | | | | | 240 |
| Tyr | Gly | Trp | Ser | Asp | Thr | Tyr | Thr | Phe | Thr | Lys | Trp | Leu | Gly | Glu | Gln |
| | | | | 245 | | | | | 250 | | | | | 255 | |
| Leu | Leu | Met | Lys | Ala | Leu | Ser | Gly | Arg | Ser | Leu | Thr | Ile | Val | Arg | Pro |
| | | | 260 | | | | | 265 | | | | | 270 | | |
| Ser | Ile | Ile | Glu | Ser | Ala | Leu | Glu | Glu | Pro | Ser | Pro | Gly | Trp | Ile | Glu |
| | | | 275 | | | | | 280 | | | | | 285 | | |
| Gly | Val | Lys | Val | Ala | Asp | Ala | Ile | Ile | Leu | Ala | Tyr | Ala | Arg | Glu | Lys |
| | 290 | | | | | 295 | | | | | 300 | | | | |
| Val | Ser | Leu | Phe | Pro | Gly | Lys | Arg | Ser | Gly | Ile | Ile | Asp | Val | Ile | Pro |
| 305 | | | | | 310 | | | | | 315 | | | | | 320 |
| Val | Asp | Leu | Val | Ala | Asn | Ser | Ile | Ile | Leu | Ser | Leu | Ala | Glu | Ala | Leu |
| | | | | 325 | | | | | 330 | | | | | 335 | |
| Ser | Gly | Ser | Gly | Gln | Arg | Arg | Ile | Tyr | Gln | Cys | Cys | Ser | Gly | Gly | Ser |
| | | | 340 | | | | | 345 | | | | | 350 | | |
| Asn | Pro | Ile | Ser | Leu | Gly | Lys | Phe | Ile | Asp | Tyr | Leu | Asn | Ala | Glu | Ala |
| | | | 355 | | | | | 360 | | | | | 365 | | |
| Lys | Thr | Asn | Tyr | Ala | Ala | Tyr | Asp | Gln | Leu | Phe | Tyr | Arg | Arg | Pro | Thr |
| | 370 | | | | | 375 | | | | | 380 | | | | |

```
Lys Pro Phe Val Ala Val Asn Arg Lys Leu Phe Asp Val Val Gly
385                 390                 395                 400

Val Met Arg Val Val Leu Ser Ile Ala Arg Lys Ala Met Arg Leu Ala
                405                 410                 415

Gly Val Asn Arg Glu Leu Lys Val Leu Lys Asn Leu Asp Thr Thr Arg
                420                 425                 430

Lys Leu Ala Thr Ile Phe Gly Phe Tyr Thr Ala Pro Asp Tyr Ile Phe
                435                 440                 445

Arg Asn Asp Ser Leu Met Ala Leu Ala Gln Arg Met Gly Glu Leu Asp
        450                 455                 460

Arg Val Leu Phe Pro Val Asp Ala Arg Gln Ile Asp Trp Gln Leu Tyr
465                 470                 475                 480

Leu Cys Lys Ile His Leu Arg Gly Leu Asn Arg Tyr Ala Leu Lys Glu
                485                 490                 495

Arg Lys Leu Tyr Ser Ser Arg Ala Ala Asp Thr Asp Lys Thr Ala
                500                 505                 510

<210> SEQ ID NO 29
<211> LENGTH: 5905
<212> TYPE: DNA
<213> ORGANISM: Artificial Sequence
<220> FEATURE:
<223> OTHER INFORMATION: Synthetic polynucleotide for pLS8379

<400> SEQUENCE: 29
ggcatccgct tacagacaag ctgtgaccgt ctccgggagc tgcatgtgtc agaggttttc     60
accgtcatca ccgaaacgcg cgaggcagca gatcaattcg cgcgcgaagg cgaagcggca    120
tgcatttacg ttgacaccat cgaatggtgc aaaacctttc gcggtatggc atgatagcgc    180
ccggaagaga gtcaattcag ggtggtgaat gtgaaaccag taacgttata cgatgtcgca    240
gagtatgccg gtgtctctta tcagaccgtt tcccgcgtgg tgaaccaggc cagccacgtt    300
tctgcgaaaa cgcgggaaaa agtggaagcg gcgatggcgg agctgaatta cattcccaac    360
cgcgtggcac aacaactggc gggcaaacag tcgttgctga ttggcgttgc cacctccagt    420
ctggccctgc acgcgccgtc gcaaattgtc gcggcgatta atctcgcgcg atcaactg     480 ggtgccagcg tggtggtgtc gatggtagaa cgaagcggcg tcgaagcctg taaagcggcg    540
gtgcacaatc ttctcgcgca acgcgtcagt gggctgatca ttaactatcc gctggatgac    600
caggatgcca ttgctgtgga agctgcctgc actaatgttc cggcgttatt tcttgatgtc    660
tctgaccaga cacccatcaa cagtattatt ttctcccatg aagacggtac gcgactgggc    720
gtggagcatc tggtcgcatt gggtcaccag caaatcgcgc tgttagcggg cccattaagt    780
tctgtctcgg cgcgtctgcg tctggctggc tggcataaat atctcactcg caatcaaatt    840
cagccgatag cggaacggga aggcgactgg agtgccatgt ccggttttca acaaaccatg    900
caaatgctga atgagggcat cgttcccact gcgatgctgg ttgccaacga tcagatggcg    960
ctgggcgcaa tgcgcgccat taccgagtcc gggctgcgcg ttggtgcgga tatctcggta   1020
gtgggatacg acgataccga agacagctca tgttatatcc gccgttaac caccatcaaa   1080 caggattttc gcctgctggg gcaaaccagc gtggaccgct tgctgcaact ctctcagggc   1140
caggcggtga agggcaatca gctgttgccc gtctcactgg tgaaaagaaa aaccaccctg   1200
gcgcccaata cgcaaaccgc ctctccccgc gcgttggccg attcattaat gcagctggca   1260
cgacaggttt cccgactgga aagcgggcag tgagcgcaac gcaattaatg taagttagcg   1320
cgaattgatc tggtttgaca gcttatcatc gactgcacgg tgcaccaatg cttctggcgt   1380
```

```
caggcagcca tcggaagctg tggtatggct gtgcaggtcg taaatcactg cataattcgt   1440
gtcgctcaag gcgcactccc gttctggata atgtttttg cgccgacatc ataacggttc    1500
tggcaaatat tctgaaatga gctgttgaca attaatcatc cggctcgtat aatgtgtgga   1560
attgtgagcg gataacaatt tcacacagga acagcgccg ctgagaaaaa gcgaagcggc    1620
actgctcttt aacaatttat cagacaatct gtgtgggcac tcgaccggaa ttatcgatta   1680
actttattat taaaaattaa agaggtatat attaatgtat cgattaaata aggaggaata   1740
aaccatggat ccgagctcga gatctgcagc tggtaccata tgggaattcg aagctttcta   1800
gaacaaaaac tcatctcaga agaggatctg aatagcgccg tcgaccatca tcatcatcat   1860
cattgagttt aaacggtctc cagcttggct gttttggcgg atgagagaag attttcagcc   1920
tgatacagat taaatcagaa cgcagaagcg gtctgataaa acagaatttg cctggcggca   1980
gtagcgcggt ggtcccacct gaccccatgc cgaactcaga agtgaaacgc cgtagcgccg   2040
atggtagtgt ggggtctccc catgcgagag tagggaactg ccaggcatca ataaaaacga   2100
aaggctcagt cgaaagactg ggcctttcgt tttatctgtt gtttgtcggt gaacgctctc   2160
ctgaggcgcc tgatgcggta ttttctcctt acgcatctgt gcggtatttc acaccgcata   2220
tggtgcactc tcagtacaat ctgctctgat gccgcatagt taagccagcc ccgacacccg   2280
ccaacacccg ctgacgagct tagtaaagcc ctcgctagat tttaatgcgg atgttgcgat   2340
tacttcgcca actattgcga taacaagaaa aagccagcct ttcatgatat atctcccaat   2400
ttgtgtaggg cttattatgc acgcttaaaa ataataaaag cagacttgac ctgatagttt   2460
ggctgtgagc aattatgtgc ttagtgcatc taacgcttga gttaagccgc gccgcgaagc   2520
ggcgtcggct tgaacgaatt gttagacatt atttgccgac taccttggtg atctcgcctt   2580
tcacgtagtg gacaaattct tccaactgat ctgcgcgcga ggccaagcga tcttcttctt   2640
gtccaagata agcctgtcta gcttcaagta tgacgggctg atactgggcc ggcaggcgct   2700
ccattgccca gtcggcagcg acatccttcg gcgcgatttt gccggttact gcgctgtacc   2760
aaatgcggga caacgtaagc actacatttc gctcatcgcc agcccagtcg gcggcgagt    2820
tccatagcgt taaggtttca tttagcgcct caaatagatc ctgttcagga accggatcaa   2880
agagttcctc cgccgctgga cctaccaagg caacgctatg ttctcttgct tttgtcagca   2940
agatagccag atcaatgtcg atcgtggctg gctcgaagat acctgcaaga atgtcattgc   3000
gctgccattc tccaaattgc agttcgcgct tagctggata acgccacgga atgatgtcgt   3060
cgtgcacaac aatggtgact tctacagcgc ggagaatctc gctctctcca ggggaagccg   3120
aagtttccaa aaggtcgttg atcaaagctc gccgcgttgt ttcatcaagc cttacggtca   3180
ccgtaaccag caaatcaata tcactgtgtg gcttcaggcc gccatccact gcggagccgt   3240
acaaatgtac ggccagcaac gtcggttcga gatggcgctc gatgacgcca actacctctg   3300
atagttgagt cgatacttcg gcgatcaccg cttccctcat gatgtttaac tttgttttag   3360
ggcgactgcc ctgctgcgta acatcgttgc tgctccataa catcaaacat cgacccacgg   3420
cgtaacgcgc ttgctgcttg gatgcccgag gcatagactg tacccaaaaa aacagtcat   3480
aacaagccat gaaaaccgcc actgcgccgt taccaccgct gcgttcggtc aaggttctgg   3540
accagttgcg tgagcgcata cgctacttgc attacagctt acgaaccgaa caggcttatg   3600
tccactgggt tcgtgccttc atccgtttcc acggtgtgcg tcaccggca accttgggca    3660
gcagcgaagt cgaggcattt ctgtcctggc tggcgaacga gcgcaaggtt tcggtctcca   3720
```

```
cgcatcgtca ggcattggcg gccttgctgt tcttctacgg caaggtgctg tgcacggatc    3780
tgccctggct tcaggagatc ggaagacctc ggccgtcgcg gcgcttgccg gtggtgctga    3840
ccccggatga agtggttcgc atcctcggtt ttctggaagg cgagcatcgt tgttcgccc     3900
agcttctgta tggaacgggc atgcggatca gtgagggttt gcaactgcgg gtcaaggatc    3960
tggatttcga tcacggcacg atcatcgtgc gggagggcaa gggctccaag gatcgggcct    4020
tgatgttacc cgagagcttg gcacccagcc tgcgcgagca ggggaattaa ttcccacggg    4080
ttttgctgcc cgcaaacggg ctgttctggt gttgctagtt tgttatcaga atcgcagatc    4140
cggcttcagc cggtttgccg gctgaaagcg ctatttcttc cagaattgcc atgattttt     4200
ccccacggga ggcgtcactg gctcccgtgt tgtcggcagc tttgattcga taagcagcat    4260
cgcctgtttc aggctgtcta tgtgtgactg ttgagctgta acaagttgtc tcaggtgttc    4320
aatttcatgt tctagttgct ttgttttact ggtttcacct gttctattag gtgttacatg    4380
ctgttcatct gttacattgt cgatctgttc atggtgaaca gctttgaatg caccaaaaac    4440
tcgtaaaagc tctgatgtat ctatctttt tacaccgttt tcatctgtgc atatggacag    4500
ttttcccttt gatatgtaac ggtgaacagt tgttctactt tgtttgtta gtcttgatgc    4560
ttcactgata gatacaagag ccataagaac ctcagatcct tccgtattta gccagtatgt    4620
tctctagtgt ggttcgttgt ttttgcgtga gccatgagaa cgaaccattg agatcatact    4680
tactttgcat gtcactcaaa aatttgcct caaaactggt gagctgaatt tttgcagtta    4740
aagcatcgtg tagtgttttt cttagtccgt tatgtaggta ggaatctgat gtaatggttg    4800
ttggtattt gtcaccattc attttatct ggttgttctc aagttcggtt acagagatcca    4860
tttgtctatc tagttcaact tggaaaatca acgtatcagt cgggcggcct cgcttatcaa    4920
ccaccaattt catattgctg taagtgttta aatcttact tattggtttc aaaacccatt    4980
ggttaagcct tttaaactca tggtagttat tttcaagcat taacatgaac ttaaattcat    5040
caaggctaat ctctatattt gccttgtgag ttttctttg tgttagttct tttaataacc    5100
actcataaat cctcatagag tatttgtttt caaaagactt aacatgttcc agattatatt    5160
ttatgaattt ttttaactgg aaaagataag gcaatatctc ttcactaaaa actaattcta    5220
atttttcgct tgagaacttg gcatagtttg tccactggaa aatctcaaag cctttaacca    5280
aaggattcct gatttccaca gttctcgtca tcagctctct ggttgcttta gctaatacac    5340
cataagcatt ttccctactg atgttcatca tctgagcgta ttggttataa gtgaacgata    5400
ccgtccgttc tttccttgta gggttttcaa tcgtggggtt gagtagtgcc acacagcata    5460
aaattagctt ggtttcatgc tccgttaagt catagcgact aatcgctagt tcatttgctt    5520
tgaaaacaac taattcagac atacatctca attggtctag gtgattttaa tcactatacc    5580
aattgagatg ggctagtcaa tgataattac tagtccttt cctttgagtt gtgggtatct    5640
gtaaattctg ctagaccttt gctggaaaac ttgtaaattc tgctagaccc tctgtaaatt    5700
ccgctagacc tttgtgtgtt ttttttgttt atattcaagt ggttataatt tatagaataa    5760
agaaagaata aaaaaagata aaaagaatag atcccagccc tgtgtataac tcactacttt    5820
agtcagttcc gcagtattac aaaaggatgt cgcaaacgct gtttgctcct ctacaaaaca    5880
gaccttaaaa ccctaaaggc ttaag                                          5905
```

<210> SEQ ID NO 30
<211> LENGTH: 43
<212> TYPE: DNA
<213> ORGANISM: Artificial Sequence

```
<220> FEATURE:
<223> OTHER INFORMATION: Synthetic polynucleotide forward primer

<400> SEQUENCE: 30
gaccttaaaa ccctaaaggc ttaagggcat ccgcttacag aca        43

<210> SEQ ID NO 31
<211> LENGTH: 44
<212> TYPE: DNA
<213> ORGANISM: Artificial Sequence
<220> FEATURE:
<223> OTHER INFORMATION: Synthetic polynucleotide reverse primer

<400> SEQUENCE: 31
ggagaaaata ccgcatcagg cgcctcagga gagcgttcac cgac        44

<210> SEQ ID NO 32
<211> LENGTH: 23
<212> TYPE: DNA
<213> ORGANISM: Artificial Sequence
<220> FEATURE:
<223> OTHER INFORMATION: Synthetic polynucleotide forward primer

<400> SEQUENCE: 32
tacagagaac atggtagata aac        23

<210> SEQ ID NO 33
<211> LENGTH: 20
<212> TYPE: DNA
<213> ORGANISM: Artificial Sequence
<220> FEATURE:
<223> OTHER INFORMATION: Synthetic polynucleotide reverse primer

<400> SEQUENCE: 33
tagaaggcag acgtatcctg        20

<210> SEQ ID NO 34
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 34
aggaaacagc tatg        14

<210> SEQ ID NO 35
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 35
aggaaacagc tatggtagat aaacgcgaat c        31

<210> SEQ ID NO 36
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 36
tcatcatcat cattgagttt aggaaacagc tatggtagat aaac        44
```

<210> SEQ ID NO 37
<211> LENGTH: 43
<212> TYPE: DNA
<213> ORGANISM: Artificial Sequence
<220> FEATURE:
<223> OTHER INFORMATION: Synthetic polynucleotide forward primer

<400> SEQUENCE: 37
tcatcatcat cattgagttt tacagagaac atggtagata aac        43

<210> SEQ ID NO 38
<211> LENGTH: 41
<212> TYPE: DNA
<213> ORGANISM: Artificial Sequence
<220> FEATURE:
<223> OTHER INFORMATION: Synthetic polynucleotide reverse primer

<400> SEQUENCE: 38
agccaagctg gagaccgttt ttagaaggca gacgtatcct g        41

<210> SEQ ID NO 39
<211> LENGTH: 26
<212> TYPE: DNA
<213> ORGANISM: Artificial Sequence
<220> FEATURE:
<223> OTHER INFORMATION: Synthetic polynucleotide forward primer

<400> SEQUENCE: 39
acaggaagag tatcatgact actaac        26

<210> SEQ ID NO 40
<211> LENGTH: 23
<212> TYPE: DNA
<213> ORGANISM: Artificial Sequence
<220> FEATURE:
<223> OTHER INFORMATION: Synthetic polynucleotide reverse primer

<400> SEQUENCE: 40
ttaggcctcc cggctacgag cac        23

<210> SEQ ID NO 41
<211> LENGTH: 41
<212> TYPE: DNA
<213> ORGANISM: Artificial Sequence
<220> FEATURE:
<223> OTHER INFORMATION: Synthetic polynucleotide forward primer

<400> SEQUENCE: 41
atcatcatca tcattgagtt taggaagagt atcatgacta c        41

<210> SEQ ID NO 42
<211> LENGTH: 41
<212> TYPE: DNA
<213> ORGANISM: Artificial Sequence
<220> FEATURE:
<223> OTHER INFORMATION: Synthetic polynucleotide reverse primer

<400> SEQUENCE: 42
cagccaagct ggagaccgtt tttaggcctc ccggctacga g        41

<210> SEQ ID NO 43
<211> LENGTH: 71
<212> TYPE: DNA
<213> ORGANISM: Artificial Sequence
<220> FEATURE:
<223> OTHER INFORMATION: Synthetic polynucleotide forward primer

<400> SEQUENCE: 43
tcgacataga tctagaactt actcggaagc ttcttaatta agaggatcca ttgacgtcta    60
tgaattcgtt t                                                        71

<210> SEQ ID NO 44
<211> LENGTH: 67
<212> TYPE: DNA
<213> ORGANISM: Artificial Sequence
<220> FEATURE:
<223> OTHER INFORMATION: Synthetic polynucleotide reverse primer

<400> SEQUENCE: 44
aaacgaattc atagacgtca atggatcctc ttaattaaga agcttccgag taagttctag    60
atctatg                                                             67

<210> SEQ ID NO 45
<211> LENGTH: 33
<212> TYPE: DNA
<213> ORGANISM: Artificial Sequence
<220> FEATURE:
<223> OTHER INFORMATION: Synthetic polynucleotide forward primer

<400> SEQUENCE: 45
actaagtcga cataaggaga tatacatatg acc                                33

<210> SEQ ID NO 46
<211> LENGTH: 24
<212> TYPE: DNA
<213> ORGANISM: Artificial Sequence
<220> FEATURE:
<223> OTHER INFORMATION: Synthetic polynucleotide reverse primer

<400> SEQUENCE: 46
aggtcaagct tattagtctt tacg                                          24

<210> SEQ ID NO 47
<211> LENGTH: 30
<212> TYPE: DNA
<213> ORGANISM: Artificial Sequence
<220> FEATURE:
<223> OTHER INFORMATION: Synthetic polynucleotide forward primer

<400> SEQUENCE: 47
agtaagcttg agtttaggaa gagtatcatg                                    30

<210> SEQ ID NO 48
<211> LENGTH: 29
<212> TYPE: DNA
<213> ORGANISM: Artificial Sequence
<220> FEATURE:
<223> OTHER INFORMATION: Synthetic polynucleotide reverse primer

<400> SEQUENCE: 48
aagctgacgt cttaggcctc ccggctacg                                     29

<210> SEQ ID NO 49
<211> LENGTH: 29
<212> TYPE: DNA
<213> ORGANISM: Artificial Sequence
<220> FEATURE:
<223> OTHER INFORMATION: Synthetic polynucleotide forward primer

<400> SEQUENCE: 49
agtaagcttg agttttacag agaacatgg                                29

<210> SEQ ID NO 50
<211> LENGTH: 30
<212> TYPE: DNA
<213> ORGANISM: Artificial Sequence
<220> FEATURE:
<223> OTHER INFORMATION: Synthetic polynucleotide reverse primer

<400> SEQUENCE: 50
aagctgacgt cttagaaggc agacgtatcc                               30

<210> SEQ ID NO 51
<211> LENGTH: 29
<212> TYPE: DNA
<213> ORGANISM: Artificial Sequence
<220> FEATURE:
<223> OTHER INFORMATION: Synthetic polynucleotide forward primer

<400> SEQUENCE: 51
agtaagcttg agtttaggaa acagctatg                                29

<210> SEQ ID NO 52
<211> LENGTH: 30
<212> TYPE: DNA
<213> ORGANISM: Artificial Sequence
<220> FEATURE:
<223> OTHER INFORMATION: Synthetic polynucleotide reverse primer

<400> SEQUENCE: 52
aagctgacgt cttagaaggc agacgtatcc                               30

<210> SEQ ID NO 53
<211> LENGTH: 28
<212> TYPE: DNA
<213> ORGANISM: Artificial Sequence
<220> FEATURE:
<223> OTHER INFORMATION: Synthetic polynucleotide forward primer

<400> SEQUENCE: 53
gccatcgcca gagtgaaaat aaattccg                                 28

<210> SEQ ID NO 54
<211> LENGTH: 35
<212> TYPE: DNA
<213> ORGANISM: Artificial Sequence
<220> FEATURE:
<223> OTHER INFORMATION: Synthetic polynucleotide reverse primer

<400> SEQUENCE: 54
gatttcaaag atgagagttt tatcagccag ttcct                         35

<210> SEQ ID NO 55
<211> LENGTH: 28
<212> TYPE: DNA
<213> ORGANISM: Artificial Sequence
<220> FEATURE:
<223> OTHER INFORMATION: Synthetic polynucleotide forward primer

<400> SEQUENCE: 55
ttggagcgaa tgcttaacag caaacggg                                 28

<210> SEQ ID NO 56
<211> LENGTH: 28
<212> TYPE: DNA
<213> ORGANISM: Artificial Sequence

```
<220> FEATURE:
<223> OTHER INFORMATION: Synthetic polynucleotide reverse primer

<400> SEQUENCE: 56
tgcgccactg ctggaatcat ggcagcgt                                      28

<210> SEQ ID NO 57
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 57
gaaaattatc ggcgaacagc                                               20

<210> SEQ ID NO 58
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 58
gttaattaag aacataccgg ctccttat                                      28

<210> SEQ ID NO 59
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 59
cttacatcac gggtgaaact                                               20

<210> SEQ ID NO 60
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 60
atctgcctgc aacgactctt                                               20

<210> SEQ ID NO 61
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 61
gatacgaccc gtaaacttgc aaccattttt ggc                                33

<210> SEQ ID NO 62
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 62
cgcttctgcg ttctgattt                                                19
```

-continued

<210> SEQ ID NO 63
<211> LENGTH: 682
<212> TYPE: DNA
<213> ORGANISM: Artificial Sequence
<220> FEATURE:
<223> OTHER INFORMATION: Synthetic polynucleotide

<400> SEQUENCE: 63

```
gatatctcgg tagtgggata cgacgatacc gaagacagct catgttatat cccgccgtta      60
accaccatca aacaggattt tcgcctgctg gggcaaacca gcgtggaccg cttgctgcaa     120
ctctctcagg gccaggcggt gaagggcaat cagctgttgc ccgtctcact ggtgaaaaga     180
aaaaccaccc tggcgcccaa tacgcaaacc gcctctcccc gcgcgttggc cgattcatta     240
atgcagctgg cacgcacagt tcccgactg gaaagcgggc agtaataatt taaattggtt     300
tgacagctta tcatcgactg cacggtgcac caatgcttct ggcgtcaggc agccatcgga     360
agctgtggta tggctgtgca ggtcgtaaat cactgcataa ttcgtgtcgc tcaaggcgca     420
ctcccgttct ggataatgtt ttttgcgccg acataattgt gagcgctcac aatttctgaa     480
atgagctgtt gacaattaat catccggctc gtataatgtg tggaattgtg agcggataac     540
aatttcacac aggaaacagc gccgctgaga aaaagcgaag cggcactgct ctttaacaat     600
ttatcagaca atctgtgtgg gcactcgacc ggaattatcg attaacttta ttattaaaaa     660
ttaaaggagg aataaaccat gg                                              682
```

<210> SEQ ID NO 64
<211> LENGTH: 44
<212> TYPE: DNA
<213> ORGANISM: Artificial Sequence
<220> FEATURE:
<223> OTHER INFORMATION: Synthetic polynucleotide forward primer

<400> SEQUENCE: 64

```
cgcaggctat tctggtggcc ggaaggcgaa gcggcatgca ttta                       44
```

<210> SEQ ID NO 65
<211> LENGTH: 60
<212> TYPE: DNA
<213> ORGANISM: Artificial Sequence
<220> FEATURE:
<223> OTHER INFORMATION: Synthetic polynucleotide reverse primer

<400> SEQUENCE: 65

```
aacgacggcc agtgaatccg taatcatggt catggtttat tcctcctttaa attttaata     60
```

<210> SEQ ID NO 66
<211> LENGTH: 44
<212> TYPE: DNA
<213> ORGANISM: Artificial Sequence
<220> FEATURE:
<223> OTHER INFORMATION: Synthetic polynucleotide forward primer

<400> SEQUENCE: 66

```
cgcaggctat tctggtggcc ggaaggcgaa gcggcatgca ttta                       44
```

<210> SEQ ID NO 67
<211> LENGTH: 60
<212> TYPE: DNA
<213> ORGANISM: Artificial Sequence
<220> FEATURE:
<223> OTHER INFORMATION: Synthetic polynucleotide reverse primer

<400> SEQUENCE: 67
agttgggtaa cgccagggtt ttcccagtca cgacgttgta aaacgacggc cagtgaatcc    60

<210> SEQ ID NO 68
<211> LENGTH: 80
<212> TYPE: DNA
<213> ORGANISM: Artificial Sequence
<220> FEATURE:
<223> OTHER INFORMATION: Synthetic polynucleotide forward primer

<400> SEQUENCE: 68
gggcactcga ccggaattat cgattaactt tattattaaa aattaaagga ggaataaacc    60
atgaccgcag gactgatggc                                              80

<210> SEQ ID NO 69
<211> LENGTH: 75
<212> TYPE: DNA
<213> ORGANISM: Artificial Sequence
<220> FEATURE:
<223> OTHER INFORMATION: Synthetic polynucleotide reverse primer

<400> SEQUENCE: 69
caaactgatt attgatggtg aacatgatgc cgacaatcga ggcacacagc gcccagaaag    60
gacaagtttt ggtga                                                   75

<210> SEQ ID NO 70
<211> LENGTH: 21
<212> TYPE: DNA
<213> ORGANISM: Artificial Sequence
<220> FEATURE:
<223> OTHER INFORMATION: Synthetic polynucleotide forward primer

<400> SEQUENCE: 70
ggctgggatc aggaggagaa g                                            21

<210> SEQ ID NO 71
<211> LENGTH: 25
<212> TYPE: DNA
<213> ORGANISM: Artificial Sequence
<220> FEATURE:
<223> OTHER INFORMATION: Synthetic polynucleotide reverse primer

<400> SEQUENCE: 71
aatgatcagt ggcgcaaaga acata                                        25

<210> SEQ ID NO 72
<211> LENGTH: 24
<212> TYPE: DNA
<213> ORGANISM: Artificial Sequence
<220> FEATURE:
<223> OTHER INFORMATION: Synthetic polynucleotide forward primer

<400> SEQUENCE: 72
ccagcgtgga ccgcttgctg caac                                         24

<210> SEQ ID NO 73
<211> LENGTH: 19
<212> TYPE: DNA
<213> ORGANISM: Artificial Sequence
<220> FEATURE:
<223> OTHER INFORMATION: Synthetic polynucleotide reverse primer

<400> SEQUENCE: 73
cccggagtga tcttatttc                                               19

<210> SEQ ID NO 74
<211> LENGTH: 21
<212> TYPE: DNA
<213> ORGANISM: Artificial Sequence
<220> FEATURE:
<223> OTHER INFORMATION: Synthetic polynucleotide forward primer

<400> SEQUENCE: 74
ggctgggatc aggaggagaa g                                           21

<210> SEQ ID NO 75
<211> LENGTH: 21
<212> TYPE: DNA
<213> ORGANISM: Artificial Sequence
<220> FEATURE:
<223> OTHER INFORMATION: Synthetic polynucleotide reverse primer

<400> SEQUENCE: 75
tcagcaggct accaccgttc g                                           21

<210> SEQ ID NO 76
<211> LENGTH: 23
<212> TYPE: DNA
<213> ORGANISM: Artificial Sequence
<220> FEATURE:
<223> OTHER INFORMATION: Synthetic polynucleotide forward primer

<400> SEQUENCE: 76
tgcggaactg gcgttttctt acc                                         23

<210> SEQ ID NO 77
<211> LENGTH: 20
<212> TYPE: DNA
<213> ORGANISM: Artificial Sequence
<220> FEATURE:
<223> OTHER INFORMATION: Synthetic polynucleotide reverse primer

<400> SEQUENCE: 77
gtagaaactg ccggaaatcg                                             20

<210> SEQ ID NO 78
<211> LENGTH: 132
<212> TYPE: DNA
<213> ORGANISM: Artificial Sequence
<220> FEATURE:
<223> OTHER INFORMATION: Synthetic polynucleotide forward primer

<400> SEQUENCE: 78
tctttcatac aatgacatat taaaatatca gcaagaattc caaagggttt ttttaggcct    60
ttgacagcta gctcagtcct aggtatactg ctagcatact agaggccagc ctggccataa   120
ggagatatac at                                                      132

<210> SEQ ID NO 79
<211> LENGTH: 70
<212> TYPE: DNA
<213> ORGANISM: Artificial Sequence
<220> FEATURE:
<223> OTHER INFORMATION: Synthetic polynucleotide reverse primer

<400> SEQUENCE: 79
ttgaaatact tcgaattgat attcagacat ttctgcccat gtttgctgaa aggacaagtt    60
ttggtgactg                                                          70

```
<210> SEQ ID NO 80
<211> LENGTH: 20
<212> TYPE: DNA
<213> ORGANISM: Artificial Sequence
<220> FEATURE:
<223> OTHER INFORMATION: Synthetic polynucleotide forward primer

<400> SEQUENCE: 80
accagccttg gggtaaaacg                                                20

<210> SEQ ID NO 81
<211> LENGTH: 20
<212> TYPE: DNA
<213> ORGANISM: Artificial Sequence
<220> FEATURE:
<223> OTHER INFORMATION: Synthetic polynucleotide reverse primer

<400> SEQUENCE: 81
ttttgggtta agcgtctcgt                                                20

<210> SEQ ID NO 82
<211> LENGTH: 42
<212> TYPE: DNA
<213> ORGANISM: Artificial Sequence
<220> FEATURE:
<223> OTHER INFORMATION: Synthetic polynucleotide forward primer

<400> SEQUENCE: 82
ctgacgataa aaccgcctaa gtcgacataa ggagatatac at                       42

<210> SEQ ID NO 83
<211> LENGTH: 34
<212> TYPE: DNA
<213> ORGANISM: Artificial Sequence
<220> FEATURE:
<223> OTHER INFORMATION: Synthetic polynucleotide reverse primer

<400> SEQUENCE: 83
catgatactc ttcctaaact caagcttatt agtc                                34

<210> SEQ ID NO 84
<211> LENGTH: 21
<212> TYPE: DNA
<213> ORGANISM: Artificial Sequence
<220> FEATURE:
<223> OTHER INFORMATION: Synthetic polynucleotide forward primer

<400> SEQUENCE: 84
tcggcatgaa agcggttgat g                                              21

<210> SEQ ID NO 85
<211> LENGTH: 21
<212> TYPE: DNA
<213> ORGANISM: Artificial Sequence
<220> FEATURE:
<223> OTHER INFORMATION: Synthetic polynucleotide reverse primer

<400> SEQUENCE: 85
gagaaaatac cgcatcaggc g                                              21

<210> SEQ ID NO 86
<211> LENGTH: 33
<212> TYPE: DNA
<213> ORGANISM: Artificial Sequence
<220> FEATURE:
<223> OTHER INFORMATION: Synthetic polynucleotide forward primer
```

<400> SEQUENCE: 86
gatacgaccc gtaaacttgc aaccattttt ggc    33

<210> SEQ ID NO 87
<211> LENGTH: 19
<212> TYPE: DNA
<213> ORGANISM: Artificial Sequence
<220> FEATURE:
<223> OTHER INFORMATION: Synthetic polynucleotide reverse primer

<400> SEQUENCE: 87
cgcttctgcg ttctgattt    19

<210> SEQ ID NO 88
<211> LENGTH: 49
<212> TYPE: DNA
<213> ORGANISM: Artificial Sequence
<220> FEATURE:
<223> OTHER INFORMATION: Synthetic polynucleotide forward primer

<400> SEQUENCE: 88
ctgacgataa aaccgcctaa gtcgacataa ggagatatac atatgaccg    49

<210> SEQ ID NO 89
<211> LENGTH: 47
<212> TYPE: DNA
<213> ORGANISM: Artificial Sequence
<220> FEATURE:
<223> OTHER INFORMATION: Synthetic polynucleotide reverse primer

<400> SEQUENCE: 89
aaacgaattc atagacgtca agcttattag tctttacgac ccgtgac    47

<210> SEQ ID NO 90
<211> LENGTH: 56
<212> TYPE: DNA
<213> ORGANISM: Artificial Sequence
<220> FEATURE:
<223> OTHER INFORMATION: Synthetic polynucleotide forward primer

<400> SEQUENCE: 90
cacgggtcgt aaagactaat aagcttgacg tctatgaatt cgtttaaacg ccaggc    56

<210> SEQ ID NO 91
<211> LENGTH: 21
<212> TYPE: DNA
<213> ORGANISM: Artificial Sequence
<220> FEATURE:
<223> OTHER INFORMATION: Synthetic polynucleotide reverse primer

<400> SEQUENCE: 91
gagaaaatac cgcatcaggc g    21

<210> SEQ ID NO 92
<211> LENGTH: 50
<212> TYPE: DNA
<213> ORGANISM: Artificial Sequence
<220> FEATURE:
<223> OTHER INFORMATION: Synthetic polynucleotide forward primer

<400> SEQUENCE: 92
gacgataaaa ccgcctaata agcttgagtt taggaagagt atcatgtctg    50

<210> SEQ ID NO 93
<211> LENGTH: 21

```
<212> TYPE: DNA
<213> ORGANISM: Artificial Sequence
<220> FEATURE:
<223> OTHER INFORMATION: Synthetic polynucleotide reverse primer

<400> SEQUENCE: 93
gagaaaatac cgcatcaggc g                                                 21

<210> SEQ ID NO 94
<211> LENGTH: 28
<212> TYPE: DNA
<213> ORGANISM: Artificial Sequence
<220> FEATURE:
<223> OTHER INFORMATION: Synthetic polynucleotide forward primer

<400> SEQUENCE: 94
taaaccatgg cgactcaaca acagaaca                                          28

<210> SEQ ID NO 95
<211> LENGTH: 35
<212> TYPE: DNA
<213> ORGANISM: Artificial Sequence
<220> FEATURE:
<223> OTHER INFORMATION: Synthetic polynucleotide reverse primer

<400> SEQUENCE: 95
ctatgtcgac ttaggcggtt ttatcgtcag tatca                                  35

<210> SEQ ID NO 96
<211> LENGTH: 71
<212> TYPE: DNA
<213> ORGANISM: Artificial Sequence
<220> FEATURE:
<223> OTHER INFORMATION: Synthetic polynucleotide

<400> SEQUENCE: 96
ccggaattat cgattaactt tattattaaa aattaaagga ggaataaacc atggcgactc        60
aacaacagaa c                                                            71

<210> SEQ ID NO 97
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 97
taaggtcatg gtttattcct ccttgtcgac ttaggcggtt ttatcgtcag tatc             54

<210> SEQ ID NO 98
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 98
accgcctaag tcgacaagga ggaataaacc atgaccttag agtggaaacc aaaa             54

<210> SEQ ID NO 99
<211> LENGTH: 47
<212> TYPE: DNA
<213> ORGANISM: Artificial Sequence
<220> FEATURE:
<223> OTHER INFORMATION: Synthetic polynucleotide
```

<400> SEQUENCE: 99
gccaaacctt cttcatatgt atatctcctt ttatacccgc ggctcgg        47

<210> SEQ ID NO 100
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 100
cgagccgcgg gtataaaagg agatatacat atgaagaagg tttggcttaa ccg        53

<210> SEQ ID NO 101
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 101
ttaagaagct tccgagtaag ttctagatct tcattaggct ttattgtcca ctttg        55

<210> SEQ ID NO 102
<211> LENGTH: 76
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(1)
<223> OTHER INFORMATION: Residue 1 modified at 5' by phosphorothioate
      bond to A, in turn modified by phosphorothioate bond to A, in turn
      modified by phosphorothioate bond to G, in turn modified by
      phosphorothioate bond to G

<400> SEQUENCE: 102
ggcgaagcgg catgcattta cgttgacacc atcgaattca ctggccgtcg ttttacaacg        60
tcgtgactgg gaaaac        76

<210> SEQ ID NO 103
<211> LENGTH: 39
<212> TYPE: DNA
<213> ORGANISM: Artificial Sequence
<220> FEATURE:
<223> OTHER INFORMATION: Synthetic polynucleotide forward primer

<400> SEQUENCE: 103
gaaataagat cactccggga ttccggggat ccgtcgacc        39

<210> SEQ ID NO 104
<211> LENGTH: 75
<212> TYPE: DNA
<213> ORGANISM: Artificial Sequence
<220> FEATURE:
<223> OTHER INFORMATION: Synthetic polynucleotide reverse primer

<400> SEQUENCE: 104
caaactgatt attgatggtg aacatgatgc cgacaatcga ggcacacagc gcccagtgta        60
ggctggagct gcttc        75

PRODUCTION OF SATURATED FATTY ALCOHOLS FROM ENGINEERED MICROORGANISMS

CROSS REFERENCE TO RELATED APPLICATIONS

The present application is a national stage application filed under 35 USC §371 and claims priority to PCT International Application No. PCT/US2012/069553, filed Dec. 13, 2012, U.S. Provisional Patent Application Ser. No. 61/577,756, filed Dec. 20, 2011, U.S. Provisional Patent Application Ser. No. 61/578,673, filed Dec. 21, 2011, U.S. Provisional Patent Application Ser. No. 61/636,044, filed Apr. 20, 2012, U.S. Provisional Patent Application Ser. No. 61/674,053, filed Jul. 20, 2012, and PCT International Application No. PCT/US2012/069444, filed Dec. 13, 2012. The present application hereby incorporates both of these priority applications by reference, in their entireties and for all purposes.

FIELD OF THE INVENTION

This invention relates to recombinant bacterial microorganisms exhibiting improved properties, especially improved production of saturated fatty alcohols, wherein the fatty alcohol composition comprises fatty alcohols having carbon chain lengths of one or more of C12, C14 and C16.

REFERENCE TO A "SEQUENCE LISTING," LISTING APPENDIX SUBMITTED AS AN ASCII TEXT FILE

The Sequence Listing written in file CX5-106WO2_ST25.TXT, created on Dec. 13, 2012, 100,377 bytes, machine format IBM-PC, MS-Windows operating system, is hereby incorporated by reference.

BACKGROUND OF THE INVENTION

Crude petroleum has traditionally been used as a primary source for raw materials for producing numerous specialty chemicals. Particular specialty chemicals that can be produced from the petrochemical raw materials include fatty alcohols. Fatty alcohols have many industrial and commercial uses. For example, fatty alcohols act as surfactants which are useful in personal care and household products, such as detergents. Fatty alcohols are also used in waxes, lubricating oils, cosmetics and solvents. The longer chain fatty alcohols may be used for transportation fuels such as diesel and jet fuels. However, obtaining fatty alcohols from crude petroleum requires a significant amount of energy and involves the use of a non-renewable energy source.

Further, even those fatty alcohols that are obtained from renewable sources such as from plant or animal derived fatty acids generally are prepared using a hydrogenation step. Hydrogenation is a costly process step but is utilized to eliminate the double bonds of unsaturated fatty acids. A number of prior art references disclose genetically engineered microorganisms that produce products including fatty acid derivatives such as fatty acid esters and fatty alcohols. For example reference is made to international application publications WO2007/136762; WO2008/119082; WO2010/075483; WO2011/008535 and WO2011/019858; U.S. Pat. No. 6,143,538 and U.S. Pat. No. 8,110,670; and U.S. Patent Pub. Nos. US2012/0115195 and US2012/0142979.

However, a need still exists in the field for improved fatty alcohol production from bioengineered microorganisms that is efficient, cost effective and further tailored for use in particular industrial applications. In addition, for certain industrial applications, it is desirable to have a high degree of saturation because the presence of one or more double bonds in a fatty alcohol may lower the melting point, reduce the shelf-life and/or reduce the heat stability of the compound. Therefore, compositions and methods that provide products having increased saturation levels in fatty alcohols and/or fatty alcohol derivatives are commercially beneficial.

BRIEF SUMMARY OF THE INVENTION

This invention provides improved methods of producing fatty alcohols and fatty alcohol derivative compounds in an engineered host cell. More specifically, the invention provides engineered microorganisms (e.g., bacteria) exhibiting improved properties including the production of fatty alcohols and specifically including the production of saturated fatty alcohols and compositions comprising at least one saturated fatty alcohol (e.g., a composition comprising at least C12, C14, C16 and/or C18 saturated fatty alcohols). In some aspects, the engineered microorganisms include at least one heterologous gene encoding a fatty acyl-ACP reductase enzyme (FAR) and an over-expressed endogenous fatty acid biosynthetic (fab) gene. In some aspects, the engineered microorganisms include at least one heterologous gene encoding a fatty acyl-ACP reductase enzyme (FAR) and an inactivated (e.g. disrupted) gene that confers improved production of saturated fatty alcohols compared to a corresponding microbial organism of the same type in which the gene is not inactivated. In some embodiments, the engineered microorganism is *E. coli*.

In one aspect, the invention relates to an engineered bacterial microorganism comprising a polynucleotide encoding a heterologous fatty acyl-ACP reductase enzyme (FAR) and a first recombinant polynucleotide encoding a FabZ enzyme, wherein the engineered bacterial microorganism produces a fatty alcohol composition comprising a plurality of C10 to C18. In some embodiments, the present invention provides compositions comprising a plurality of fatty alcohols selected from C10 to C18 (e.g., C10 to C18; C10 to C16; C12 to C16, or C12 to C14) fatty alcohols. In one embodiment of this aspect, the invention further relates to the engineered bacterial microorganism comprising a second recombinant polynucleotide encoding a FabI enzyme. In another embodiment, the invention further relates to a fatty alcohol composition produced by the engineered microorganisms.

In another aspect the invention relates to an engineered bacterial microorganism comprising a polynucleotide encoding a heterologous fatty acyl-ACP reductase enzyme (FAR) and a first recombinant polynucleotide encoding a FabA enzyme wherein the engineered bacterial microorganism produces a fatty alcohol composition comprising at least one C10 to C18 fatty alcohol. In some embodiments, the present invention provides compositions comprising a plurality of fatty alcohols selected from C10 to C18 (e.g., C10 to C18; C10 to C16; C12 to C16, or C12 to C14) fatty alcohols. In some embodiments of this aspect, the invention further relates to the engineered bacterial microorganism comprising a second recombinant polynucleotide encoding a FabI enzyme. In another embodiment of this aspect, the invention further relates to a fatty alcohol composition produced by the engineered microorganisms.

In yet another aspect, the invention relates to an engineered bacterial microorganism comprising a polynucleotide encoding a heterologous fatty acyl-ACP reductase enzyme (FAR) and a first recombinant polynucleotide encoding a FabI enzyme, wherein the engineered bacterial microorganism produces a fatty alcohol composition comprising a plurality of C10 to C18 (e.g., C10 to C18; C10 to C16; C12 to C16, or C12 to C14) fatty alcohols. In some embodiments, the present invention provides compositions comprising a plurality of fatty alcohols selected from C10 to C18 fatty alcohols. In another embodiment, the invention further relates to a fatty alcohol composition produced by the engineered microorganisms.

In additional embodiments, the engineered bacterial microorganisms as described above further comprise a heterologous polynucleotide encoding a thioesterase polypeptide and optionally a polynucleotide encoding a FadD enzyme, wherein the engineered microorganism produces a fatty alcohol composition comprising a plurality of C10 to C18 (e.g., C10 to C18; C10 to C16; C12 to C16, or C12 to C14).

In addition, the invention relates to an engineered bacterial microorganism comprising a polynucleotide encoding a heterologous fatty acyl-ACP reductase enzyme (FAR) and an inactivated endogenous fabF gene encoding a FabF enzyme, wherein the engineered bacterial microorganism produces a fatty alcohol composition comprising at least one C10 to C18 fatty alcohol. In some embodiments, the present invention provides compositions comprising a plurality of fatty alcohols selected from C10 to C18 fatty alcohols. In a one embodiment of this aspect the invention further relates to a fatty alcohol composition produced by the engineered microorganisms.

Furthermore, the invention relates to an engineered bacterial microorganism comprising a polynucleotide encoding a heterologous fatty acyl-ACP reductase enzyme (FAR) and an inactivated endogenous fadR gene encoding a FadR enzyme, wherein the engineered bacterial microorganism produces a fatty alcohol composition comprising at least one C10 to C18 fatty alcohol. In some embodiments, the present invention provides compositions comprising a plurality of fatty alcohols selected from C10 to C18 fatty alcohols. In one embodiment of this aspect the invention further relates to a fatty alcohol composition produced by the engineered microorganisms.

In an additional aspect, the invention relates to a method of producing a fatty alcohol composition comprising culturing the engineered microorganisms as described herein under suitable culture conditions in which at least one fatty alcohol is produced. In some embodiments a plurality of fatty alcohols are produced (e.g., C10 to C18; C10 to C16; C12 to C16, or C12 to C14). In some embodiments, the methods further comprise recovering the fatty alcohol(s) from the culture medium and/or cells. In some additional embodiments, the recovered fatty alcohol(s) are provided in a composition. In some embodiments, the composition finds use in any suitable product or method.

In yet an additional aspect, the invention relates to a method for increasing the production of saturated fatty alcohols by engineered microorganisms to provide fatty alcohol compositions comprising the desired levels of saturated fatty alcohols. In some embodiments, the methods involve culturing the engineered microorganisms as described herein under suitable culture conditions to produce a fatty alcohol composition, wherein the fatty alcohol composition comprises at least 60% of saturated C12, C14, C16 and/or C18 fatty alcohols as compared to a fatty alcohol composition comprising C12, C14, C16 and/or C18 fatty alcohols produced by a corresponding bacterial microorganism. In some embodiments, the corresponding bacterial microorganism will be an engineered bacterial microorganism, such as a microorganism that comprises the same heterologous FAR but that does not comprise a heterologous fab gene as encompassed by the invention. In some embodiments, the methods further comprise recovering the fatty alcohol(s) from the culture medium and/or cells. In some additional embodiments, the recovered fatty alcohol(s) are provided in a composition. In some embodiments, the composition finds use in any suitable product or method. In a further aspect, the invention relates to methods of producing fatty alcohol compositions comprising contacting an engineered bacterial microorganism as described herein with at least one fermentable sugar, wherein the fermentable sugar(s) are obtained from or included in a feedstock comprising at least one cellulosic substrate.

BRIEF DESCRIPTION OF THE DRAWINGS

FIG. 3 describes some polynucleotide and amino acid FAR sequences encompassed by the invention: SEQ ID NO:1 illustrates a codon optimized FAR polynucleotide sequence encoding the wild-type FAR amino acid sequence as set forth in SEQ ID NO:2; SEQ ID NO:3 illustrates a FAR polynucleotide sequence encoding a variant FAR amino acid sequence as set forth in SEQ ID NO:4 (V1); SEQ ID NO:5 illustrates a FAR polynucleotide sequence encoding a variant FAR amino acid sequence as set forth in SEQ ID NO:6 (V2); SEQ ID NO:17 illustrates a FAR polynucleotide sequence encoding the wild-type FAR amino acid sequence as set forth in SEQ ID NO:18; and SEQ ID NO: 27 illustrates a polynucleotide sequence encoding a FAR polynucleotide encoding a variant FAR amino acid sequence as set forth in SEQ ID NO: 28 (V3).

DETAILED DESCRIPTION OF THE INVENTION

Figure 1:
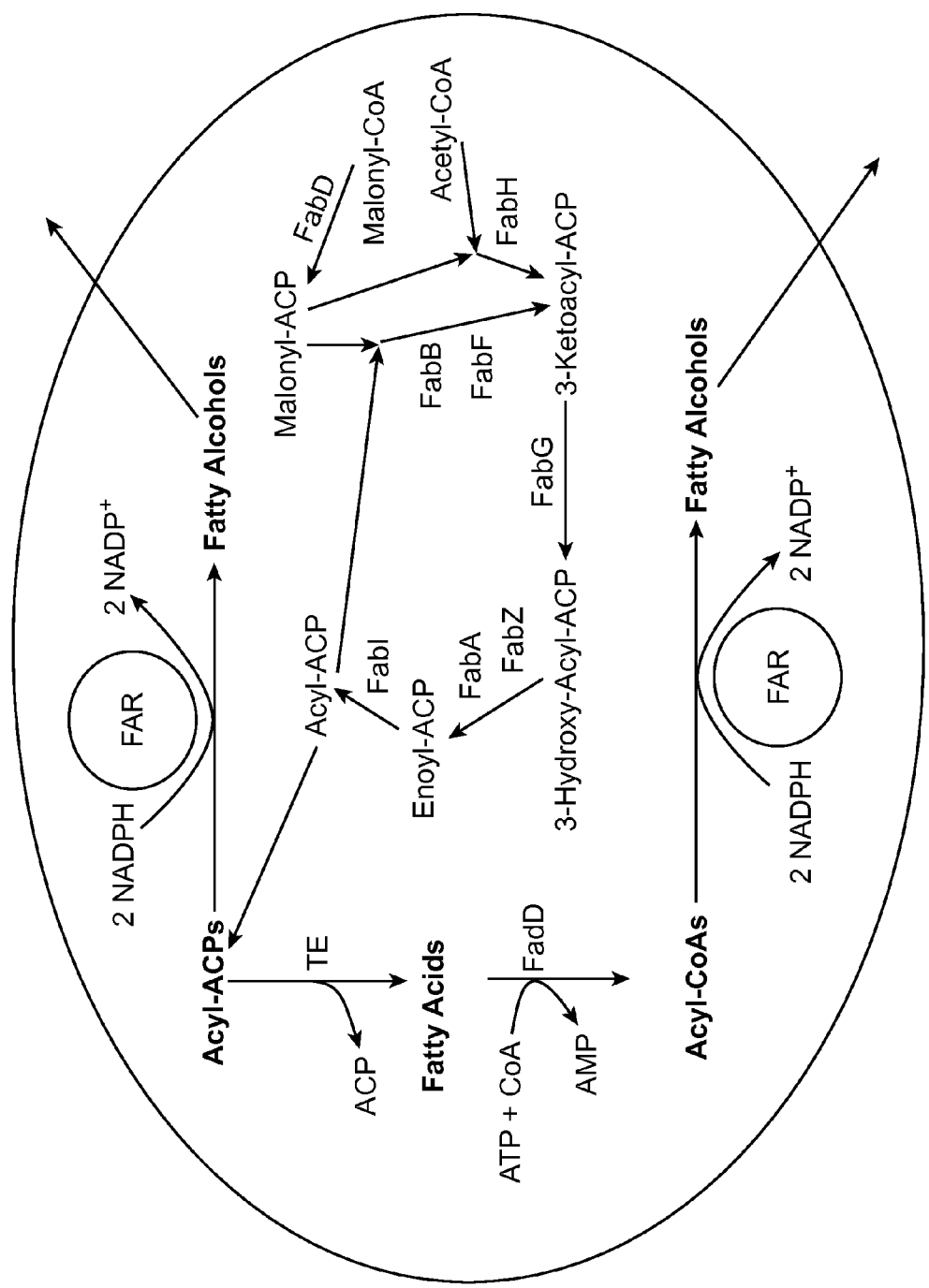
FIG. 1 illustrates the catalytic cycle in *E. coli* of fatty acid biosynthesis and products derived therefrom. Fatty acid biosynthesis is catalyzed by an enzyme system, which converts malonyl-CoA and acyl-ACP into acyl-ACP species. These enzymes are denoted as FabD; FabH; FabB; FabF; FabG; FabA; FabZ; FabI and ACP and are more fully described below. The enzymes FabB; FabF; FabG; FabA; FabZ; FabI and further ACP are involved in key steps for the elongation of acyl-ACPs in *E. coli* and for the synthesis of saturated and unsaturated fatty alcohols and fatty acids. Acyl-ACPs can be substrates of thioesterases to produce free fatty acids, which in turn can be converted to acyl-CoA derivatives by acyl-CoA synthetase enzymes (e.g., FadD). The acyl-ACP and acyl-CoA substrates are then enzymatically converted to fatty alcohols by a fatty acyl reductase (FAR) enzyme.

This invention provides recombinant bacterial microorganisms, such as *E. coli*, which have been genetically engineered to express various heterologous fatty acid biosynthetic genes such as fabZ, fabI and/or fabA and preferably express a polynucleotide encoding a heterologous FAR. In some additional embodiments, the present invention provides recombinant bacterial microorganisms that comprise the deletion of one or more endogenous genes to create a desired phenotype. These modified bacterial microorganisms find use in commercial production of fatty alcohols having desired chain length distributions and/or desired saturation levels. Indeed, it is intended that the present invention will find us in the production of fatty alcohols suitable for numerous uses in which certain chain lengths and/or saturation levels are desired.

1. DEFINITIONS

Unless otherwise indicated, the practice of the present invention involves conventional techniques commonly used in organic chemistry, molecular biology, protein engineering, microbiology, and fermentation science, which are within the skill of the art. Such techniques are well-known and described in numerous texts and reference works well known to those of skill in the art.

Unless defined otherwise herein, all technical and scientific terms used herein have the same meaning as commonly understood by one of ordinary skill in the art to which this invention pertains. Many technical dictionaries are known to those of skill in the art. Although any suitable methods and materials similar or equivalent to those described herein find use in the practice of the present invention, some methods and materials are described herein. It is to be understood that this invention is not limited to the particular methodology, protocols, and reagents described, as these may vary, depending upon the context they are used by those of skill in the art.

Also, as used herein, the singular "a", "an," and "the" include the plural references, unless the context clearly indicates otherwise. Further, the term "or" is used in the present application to mean the disjunctive "or" and the conjunctive "and".

Amino acids are designated using the three-letter symbols or one-letter symbols recommended by the IUPAC-IUB Biochemical Nomenclature Commission. Unless otherwise indicated, nucleic acids are written left to right in 5' to 3' orientation; amino acid sequences are written left to right in amino to carboxy orientation, respectively. "EC" number refers to the Enzyme Nomenclature of the Nomenclature Committee of the International Union of Biochemistry and Molecular Biology (NC-IUBMB). The IUBMB biochemical classification is a numerical classification system for enzymes based on the chemical reactions they catalyze.

Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

Furthermore, the headings provided herein are not limitations of the various aspects or embodiments of the invention which can be had by reference to the application as a whole. Accordingly, the terms defined immediately below are more fully defined by reference to the application as a whole. Nonetheless, in order to facilitate understanding of the invention, a number of terms are defined below.

As used herein, the term "comprising" and its cognates are used in their inclusive sense (i.e., equivalent to the term "including" and its corresponding cognates).

The term "fatty alcohol" as used herein refers to an aliphatic alcohol of the formula R—OH, where the R group is at least 4, 6, 7, 8, 9, 10, 11, 12, 13, 14, 15, 16, 17, 18, 19, 20 and more carbons in length. R can be saturated or unsaturated. Further saturated or unsaturated fatty alcohols can be described as "Ca:b-OH", wherein "a" is an integer that represents the total number of carbon atoms in the fatty alcohol and "b" is an integer that refers to the number of double bonds in the carbon chain. In some embodiments, a fatty alcohol produced according to the methods disclosed herein is a C8-C24 saturated or unsaturated fatty alcohol (i.e., a C8, C9, C10, C11, C12, C13, C14, C15, C16, C17, C18, C19, C20, C21, C22, or C24 fatty alcohol). In some embodiments, multiple fatty alcohols are produced with varying saturation levels. For example, in some embodiments, C10, C12, C14, C16 and/or C18 fatty alcohols are produced. However, it is not intended that the present invention be limited to any particular fatty alcohol nor fatty alcohol saturation level. In some embodiments, one or more of the following fatty alcohols is produced: 1-decanol (C10:0), 1-dodecanol (C12:0), 1-tetradecanol (C14:0), 1-hexadecanol (C16:0), 1-octadecanol (C18:0).

The abbreviation "ACP" refers to an acyl carrier protein.

The term "fatty acid" as used herein means a compound having the formula $RCO_2H$, wherein R is at least two carbons in length and general R is between 4 and 22 carbons in length. Fatty acids may be saturated or unsaturated and further R can be linear or branched.

The term "fatty acyl-ACP as used herein means a compound of the formula below wherein R is at least three carbons in length and may be a saturated or unsaturated straight or branched chain.

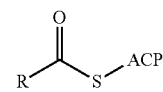

The terms "fatty acyl-CoA reductase", "fatty acyl reductase", and "fatty acyl acyl-ACP reductase" (E.C.1.1.1.*) are used interchangeably herein to refer to an enzyme that catalyzes the reduction of a fatty acyl-CoA, a fatty acyl-ACP, or other fatty acyl thioester complex to a fatty alcohol, in a reaction linked to the oxidation of NAD(P)H to NAD(P)$^+$. The abbreviation "FAR" is used herein to refer to these fatty alcohol forming enzymes. In some embodiments, a FAR enzyme includes functional fragments. In some embodiments, the FAR enzyme is a modified or variant FAR, wherein a wild-type FAR has been genetically modified to include at least 1 (at least 2, 3, 4, 5, 6, 7, 8, 9, 10, 12, 15, 20, 25, 30 or more) amino acid alterations (e.g., substitutions, deletions and/or insertions) as compared to a reference FAR.

The term "acyl-CoA" refers to an acyl thioester formed between the carbonyl carbon of an alkyl chain and the sulfydryl group of the 4'-phosphopantetthionyl moiety of co-enzyme A (CoA) which has the formula R—C(O)—S—CoA, wherein R is an alkyl group having at least 4 carbon atoms and preferably between 10 and 14 carbon atoms. R may be straight or branched and saturated or unsaturated.

Figure 2:
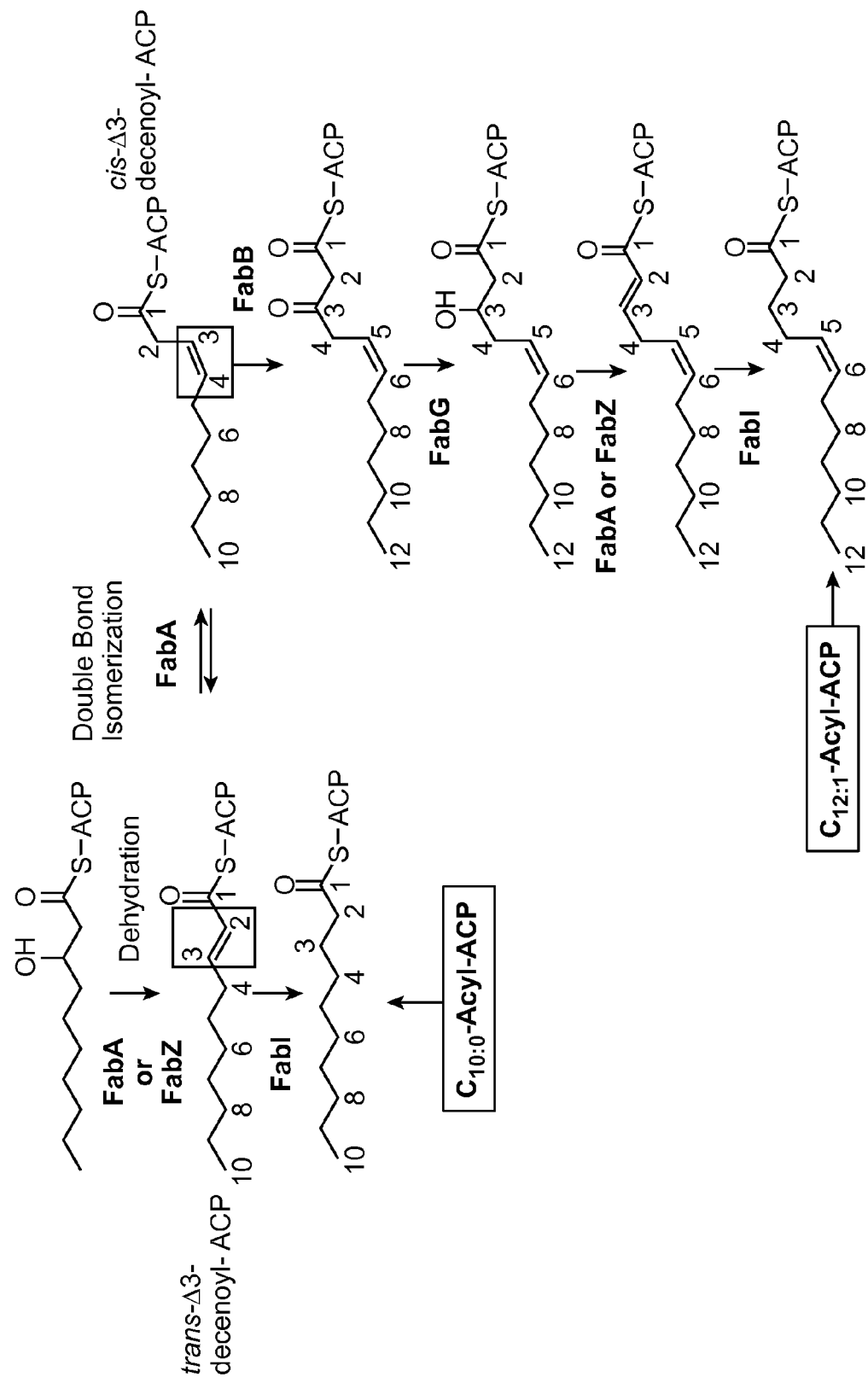
FIG. 2 illustrates key steps for saturated and unsaturated fatty acid biosynthesis in *E. coli*. Fatty acids are synthesized by the sequential addition of the 2-carbon molecular malonyl-ACP. Fully saturated fatty acids are produced up to a chain length of 8 carbons (C8:0-ACP). In the next elongation step, the isomerase activity of FabA catalyzes the production of cis-$\Delta^3$-decenoyl-ACP. This intermediate is extended to C12:1-ACP. The introduced double bond is retained in subsequent elongation steps up to C18:1-ACP. In the parallel saturated pathway trans-$\Delta^3$-decenoyl-ACP is reduced by FabI to produce C10:0-acyl-ACP, which can further be elongated to produce predominantly up to C16:0-ACP. The pathways for further elongation steps to, for example, C16:0-acyl-ACP or C18:1-acyl-ACP are not shown.

"Fatty acid biosynthetic enzymes" comprise a complex of enzymes involved in a number of reactions to produce saturated and unsaturated fatty acids (See, FIGS. 1 and 2). The process is primed by the enzymatic conversion of malonyl-CoA into malonyl-ACP and continues by successive addition of 2 carbons derived from malonyl-ACP residues, providing ACP intermediates (i.e., acyl-ACPs). There are at least 8 enzymes involved fatty acid biosynthesis including FabA, FabB, FabD, FabF, FabG, FabH, FabI, and FabZ, collectively and individually referred to herein as "fatty acid biosynthetic (Fab)" enzymes. Furthermore, the ACP protein plays a key role in fatty acid biosynthesis by anchoring the nascent acyl chain and making the acyl chain accessible to other enzymes.

A "FabZ" enzyme as used herein, refers to a "β-hydroxyacyl-ACP dehydratase" (EC 4.2.1.59 to 4.2.61) that catalyzes the reaction of a (3R)-3-hydroxyacyl-ACP to a trans$\Delta^2$-enoyl-acylACP+$H_2O$. FabZ is encoded by a fabZ gene.

A "FabA" enzyme as used herein, refers to a "β-hydroxyacyl-ACP dehydratase" (EC 4.2.1.59 to 4.2.61) that catalyzes the reaction of a (3R)-3-hydroxyacyl-ACP to a trans$\Delta^2$-enoyl-acyl ACP+$H_2O$. In addition, the FabA enzyme as used herein has an isomerase activity which catalyzes the reversible isomerization of a trans$\Delta^2$-decenoyl-ACP to cis$\Delta^3$-decenoyl-ACP. FabA is encoded by a fabA gene.

A "FabI" enzyme as used herein, refers to an enoyl-[ACP] reductase (EC 1.3.1.9 and 1.3.1.10) that catalyzes the reaction of a trans-2,3-dehydroacyl-[ACP]+NAD(P)H+$H^+$ to an acylACP+NAD(P)$^+$. FabI is encoded by a fabI gene.

A "FabF" enzyme as used herein, refers to an 3-oxoacyl-ACP synthase (EC 23.1.170) that catalyzes the reaction of malonly-ACP+a 2,3,4-saturated acyl-ACP to a holo-ACP+a β-ketoacyl-ACP+$CO_2$. A FabF enzyme is encoded by a fabF gene.

A "FadR" protein as used herein, refers to a multifunctional dual regulator that exerts negative control over the fatty acid degradative regulon and activates expression of fabA and fabB. The FadR regulator is encoded by a fadR gene. A "regulon" comprises a set of genes under control of a single regulatory protein. Reference is made to Cronan et al., 1998 Mol. Microbiol. 29:937-943

The term "FadD" enzyme as used herein, refers to an "acyl-CoA synthetase ("ACS")" (EC 6.2.1 (acid-thiol ligases)). In some embodiments, the ACS is classified as EC 6.2.1.3. These ACSs are also known as long chain fatty acid-CoA ligases. An ACS catalyzes the reaction of free fatty acids (both saturated and unsaturated fatty acids) into metabolically active CoA esters (e.g., acyl-CoA) during fatty acid degradation. FadD is encoded by a fadD gene. In some embodiments the FadD may be classified as EC 2.3.1.86 (fatty acyl CoA synthase).

The term "FadK" enzyme as used herein is an acyl-CoA synthetase (ACS) (EC 6.2.1) that catalyzes the reaction of free fatty acids having preferentially C10 or less carbon chain lengths. In some cases the gene (fadK) encoding FadK has also been known as ydiD. Reference is made to Morgan-Kiss R M et al., 2004 J. Biol. Chem., 279:37324-37333.

In some bacterial organisms, (e.g. E. coli) fadD and fadK genes both occur and encode enzymes having ACS activity. In some bacterial organisms there may be more than two genes which encode enzymes having ACS activity.

The term "FadE" enzyme as used herein means an acyl-CoA dehydrogenase enzyme (EC 1.3.99.-). A FadE gene is also known as yafH.

Throughout the specification a reference may be made using an abbreviated gene name or an enzyme name. For example "fadD" refers to a gene encoding an acyl-CoA synthetase enzyme (ACS) or as sometimes referred to herein a FadD enzyme.

The phrase a "fatty alcohol composition" as used herein, means a composition which encompasses at least one fatty alcohol and which is produced from an engineered bacterial microorganisms according to the methods of the invention. The fatty alcohol compositions of the invention may include one or more fatty alcohols. For example a fatty alcohol composition may include only C12 fatty alcohols or a fatty alcohol composition may include for example a combination of C12, C14 and C16 fatty alcohols and these fatty alcohols may be saturated or unsaturated fatty alcohols and they may be linear or branched.

The term "carbon chain length" as used herein means the number of carbon atoms in a carbon chain of a fatty alcohol, fatty alcohol substrate (e.g., fatty acid) or a fatty alcohol derivative. For example the term "C12 fatty alcohol" refers to a fatty alcohol molecule having 12 carbons.

The terms "wild-type" or "native" used in reference to a polypeptide or protein means a polypeptide or protein expressed by a naturally occurring microorganism found in nature. When used in reference to a microorganism, the term means a naturally occurring (not genetically modified or engineered) microorganism.

As used herein, "substrate" refers to a substance or compound that is converted or suitable for conversion into another compound (e.g., a product) by the action of at least one enzyme. The term includes not only a single compound but also combinations comprising more than one compound.

As used herein, "conversion" refers to the enzymatic transformation of a substrate to at least one corresponding product. "Percent conversion" refers to the percent of the substrate that is converted to the product(s) within a specified period of time and under specified conditions.

The term "thioesterase or thioester hydrolase (TE)" enzyme used herein means an enzyme having thioesterase activity. TEs are identified as members of EC 3.1.2.1 to EC 3.1.2.27 and also EC3.1.1.5 and EC 3.1.2.-) and these enzyme which hydrolyze the thioester bond between a carbonyl group and a sulfur atom are classified based on enzyme function and substrate identity. In addition, TEs are classified based on the ThYme database (Thioester-active enzyme). In this classification system, TEs have been classified based on amino acid sequence similarity. Under the ThYme system, TEs are further divided into 24 different families (TE1-TE24). Reference is made to D. C. Cantu et al., (2010) Protein Science, 19:1281-1295 and D. C. Cantu et al., (2011) Nucleic Acid Research 39:doi10:1093/nar/gkq1072. TEs according to the invention will have the ability to catalyze a thioester cleavage reaction hydrolyzing a thioester into an acid and a thiol. TEs useful in the invention may be obtained from a number of sources including plant, bacterial, algal, and fungal sources.

The phrase "preference for cleaving a substrate having a certain carbon chain length" or "predominantly cleaving a substrate having a certain carbon chain length" means that an enzyme cleaves or hydrolyzes mainly substrates having a defined number of carbon atoms. The preference is not necessarily exclusive. For example, an enzyme may have a preference for cleaving substrates with chain lengths of 12 carbons, may still cleave substrates having chain length of 10 or 14 carbon atoms. A more specific non-limiting example includes but is not limited to a TE that predominantly hydrolyzes C12 acyl ACP. The enzyme may still cleave a C10 or C14 ACP substrate.

Nucleic acid sequences may be "introduced" into a cell by protoplast fusion, transfection, transduction, transformation, electroporation or any other suitable method known in the art. A nucleic acid sequence introduced into a eukaryotic or prokaryotic cell may be integrated into a chromosome or may be maintained as an episome.

As used herein, the terms "transformed" and "stably transformed" refer to a cell that has a non-native (i.e., heterologous) polynucleotide sequence integrated into its genome or as an episomal plasmid that is maintained for at least two generations.

As used herein the term "gene" refers to a polynucleotide (e.g., a DNA segment), that encodes a polypeptide and includes regions preceding and following the coding regions as well as intervening sequences (introns) between individual coding segments (exons).

As used herein, an "endogenous" or "homologous" gene refers to a gene that is found in a parental strain of a cell (e.g., a fungal or bacterial cell). As used herein in making comparisons between nucleic acid sequences, "homologous genes" (or "homologue" genes) refers to genes from different, but usually related species, which correspond to each other and are identical or very similar to each other. The term encompasses genes that are separated by speciation (i.e., the development of new species) (e.g., orthologous genes), as well as genes that have been separated by genetic duplication (e.g., paralogous genes).

As used herein, "heterologous" polynucleotides are any polynucleotides that are introduced into a host cell by laboratory techniques, and includes polynucleotides that are removed from a host cell, subjected to laboratory manipulation, and then reintroduced into a host cell.

In some embodiments, when "heterologous" is used with reference to a nucleic acid or polypeptide, the term refers to a sequence that is not normally expressed and secreted by an organism (e.g., a "wild-type" organism). In some embodiments, the term encompasses a sequence that comprises two or more subsequences which are not found in the same relationship to each other as normally found in nature, or is recombinantly engineered so that its level of expression, or physical relationship to other nucleic acids or other molecules in a cell, or structure, is not normally found in nature. For instance, a heterologous nucleic acid is typically recombinantly produced, having two or more sequences from unrelated genes arranged in a manner not found in nature (e.g., a nucleic acid open reading frame (ORF) of the invention operatively linked to a promoter sequence inserted into an expression cassette, such as a vector).

As used herein, a "heterologous enzyme" is used in reference to an enzyme that is encoded by a heterologous gene. However, it is also contemplated herein that a heterologous gene can encode an endogenous or homologous enzyme. As used herein, the term "heterologous gene" refers to a gene that occurs in a form not found in a parental strain of the host cell. Thus, in some embodiments, a heterologous gene is a gene that is derived from a species that is different from the species of the host cell expressing the gene. In some embodiments, a heterologous gene is a modified version of a gene that is endogenous to the host cell (e.g., an endogenous gene subjected to manipulation and then introduced or transformed into the host cell). For example, in some embodiments, a heterologous gene has an endogenous coding sequence, but has modifications in the promoter sequence. Similarly, in other embodiments, a heterologous gene encodes the same amino acid sequence as an endogenous gene, but has modifications in codon usage and/or to noncoding regions (e.g., introns), and/or combinations thereof. In some embodiments, the heterologous gene is a gene that has been modified to overexpress a gene product of interest.

As used herein the term "expression" includes any step involved in the production of a polypeptide including, but not limited to, transcription, post-transcriptional modification, translation, post-translational modification, and secretion.

As used herein, the term "overexpression" refers to any state in which a gene is caused to be expressed at an elevated rate or level as compared to the endogenous expression rate or level for that gene. In some embodiments, "overexpression" includes an elevated translation rate or level of the gene compared to the endogenous translation rate or level for that gene. In some embodiments, overexpression includes an elevated transcription rate or level of the gene compared to the endogenous transcription rate or level for that gene. It is intended that the term encompass overexpression of endogenous, as well as heterologous proteins.

The phrase "altered level of expression" means a polynucleotide or polypeptide in a recombinant microorganism encompassed by the invention is present in an amount or concentration that is different (e.g. greater or less) than the amount or concentration when compared to a corresponding reference microorganism.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (i.e., non-recombinant) form of the cell or express native genes that are otherwise abnormally expressed, under-expressed or not expressed at all as a result of deliberate human intervention. "Recombinant," "engineered," and "non-naturally occurring," when used with reference to a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (i.e., non-recombinant) form of the cell or express native genes that are otherwise expressed at a different level.

As used herein, the term "plasmid" refers to a circular double-stranded (ds) DNA construct used as a cloning vector, and which forms an extrachromosomal self-replicating genetic element in some eukaryotes or prokaryotes, or integrates into the host chromosome.

As used herein, "operably linked" refers to a configuration in which a control sequence is appropriately placed (i.e., in a functional relationship) at a position relative to a polynucleotide of interest such that the control sequence directs or regulates the expression of the polynucleotide and/or polypeptide of interest. Thus, a nucleic acid is "operably linked" to another nucleic acid sequence when it is placed into a functional relationship with another nucleic acid sequence.

As used herein, a "control sequence" includes all components, which are necessary and/or advantageous for the expression of a polynucleotide of the present disclosure. Each control sequence may be native or foreign to the polynucleotide of interest. Such control sequences include, but are not limited to, leaders, polyadenylation sequences, propeptide sequences, promoters, signal peptide sequences, and transcription terminators.

As used herein, a "modified host cell", "engineered host cell" or "recombinant host cell" is a cell whose genetic material has been altered using genetic engineering techniques. A genetically modified cell also refers to a derivative of or the progeny of a cell whose genetic material has been altered using genetic engineering techniques. An example of a genetic modification as a result of genetic engineering techniques includes a modification to the genomic DNA. Another example of a genetic modification as a result of genetic engineering techniques includes introduction of a stable heterologous nucleic acid into the cell.

The phrase "a corresponding engineered cell (or microorganism) grown under essentially the same culture conditions" as used herein means a reference host cell (either engineered or native) which is grown under essentially the same culture conditions, including but not limited to pH, temperature, time, and culture media as compared to an engineered cell encompassed by the invention and to which the reference cell is being compared to. In some specific nonlimiting examples the engineered cell encompassed by the invention which comprises heterologous polynucleotides encoding a TE, FAR and FadD will be compared to the "corresponding engineered cell".

The term "carbon source" as used herein refers to a substrate that is suitable for use as a source of carbon for cell growth.

Nucleic acids "hybridize" when they associate, typically in solution. There are numerous texts and other reference materials that provide details regarding hybridization methods for nucleic acids (See e.g., Tijssen, *Laboratory Techniques in Biochemistry and Molecular Biology-Hybridization with Nucleic Acid Probes*," Part 1, Chapter 2, Elsevier, New York, [1993], incorporated herein by reference). For polynucleotides of at least 100 nucleotides in length, low to very high stringency conditions are defined as follows: prehybridization and hybridization at 42° C. in 5×SSPE, 0.3% SDS, 200 µg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 200 nucleotides in length, the carrier material is finally washed three times each for 15 minutes using 2×SSC, 0.2% SDS at least at 50° C. ("low" stringency), at least at 55° C. ("medium" or "moderate" stringency), at least at 60° C. ("medium-high" stringency), at least at 65° C. ("high" stringency), and at least at 70° C. ("very high" stringency). In some embodiments, the stringency conditions include those that: (1) employ low ionic strength and high temperature for washing, for example 0.015 M sodium chloride/0.0015 M sodium citrate/0.1% sodium dodecyl sulfate at 50° C.; (2) employ a denaturing agent during hybridization, such as formamide, for example, 50% (v/v) formamide with 0.1% bovine serum albumin/ 0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/mL), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. In other embodiments, the stringency conditions include overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors to accomplish the desired stringency.

As used herein, "naturally-occurring enzyme" refers to an enzyme having the unmodified amino acid sequence identical to that found in nature (i.e., "wild-type"). Naturally occurring enzymes include native enzymes (i.e., those enzymes naturally expressed or found in the particular microorganism).

The term "variant" or "mutant" as used interchangeably herein refer to a polypeptide sequence or polynucleotide sequence encoding a polypeptide, said sequence comprising one or more modifications relative to a corresponding wild-type enzyme (or other specified reference sequence) or the wild-type polynucleotide (or other specified reference sequence) such as substitutions, insertions, deletions, and/or truncations of one or more specific amino acid residues or of one or more specific nucleotides or codons in the polypeptide or polynucleotide. In some embodiments, reference to a variant at an amino acid residue refers to a substitution of the amino acid residue for another amino acid residue. Mutagenesis and directed evolution methods are well known in the art for creating variants. See, e.g., U.S. Pat. No. 7,783, 428; U.S. Pat. No. 6,586,182; U.S. Pat. No. 6,117,679; and Ling, et al., 1999, "Approaches to DNA mutagenesis: an overview," *Anal. Biochem.*, 254(2):157-78; Smith, 1985, "In vitro mutagenesis," *Ann. Rev. Genet.*, 19:423-462; Carter, 1986, "Site-directed mutagenesis," *Biochem.* 237:1-7; Minshull, et al., 1999, "Protein evolution by molecular breeding," *Current Opinion in Chemical Biology*, 3:284-290.

As used herein, the term "isolated" or "recovered" refers to a material that is removed from its original environment (e.g., the natural environment, if it is naturally occurring). For example, the material is said to be "isolated" when it is present in a particular composition in a higher or lower concentration than exists in a naturally-occurring or wild-type organism or in combination with components not normally present upon expression from a naturally-occurring or wild-type organism. For example, a naturally-occurring polynucleotide or polypeptide present in a living animal is not isolated, but the same polynucleotide or polypeptide, separated from some or all of the coexisting materials in the natural system, is isolated. In some embodiments, such polynucleotides are part of a vector, and/or such polynucleotides or polypeptides are part of a composition, and still considered to be isolated, in that such vector or composition is not part of its natural environment. In some embodiments, the term isolated refers to fatty alcohol compounds of varying chain lengths which are isolated or recovered from an engineered cell according to the invention.

As used herein, the terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

As used herein, the term "biologically active fragment," or "functional fragment" refers to a polypeptide that has an amino-terminal and/or carboxy-terminal deletion(s) and/or internal deletion(s), but where the remaining amino acid sequence is identical to the corresponding positions in the sequence to which it is being compared (e.g., a full-length FAR of the present invention) and that retains substantially all of the activity of the full-length polypeptide. A biologically active fragment can comprise about 60%, about 65%, about 70%, about 75%, about 80%, about 85%, at about 90%, about 91%, about 92%, about 93%, about 94%, about 95%, about 96%, about 97%, about 98%, or about 99% of a full-length polypeptide to which the functional fragment is being compared (e.g. a functional fragment of a FAR polypeptide may comprise at least 80%, at least 85%, at least 90%, at least 93%, at least 95%, at least 96%, at least 97%, at least 98% and even at least 99% of the polypeptide of SEQ ID NOs: 2, 4, 6, or 28).

The term "inactivated" as applied to a gene refers to any genetic modification that decreases or eliminates the expression of the gene and/or the functional activity of the corresponding gene product (mRNA and/or protein). Genetic modifications may include but are not limited to complete or partial inactivation, suppression, deletion, interruption, blockage, promoter alterations, antisense RNA or down-regulation of a gene. This can be accomplished, for example, by gene "knockout," inactivation, mutation (e.g., insertion, deletion, point, or frameshift mutations that disrupt the expression or activity of the gene product), promoter alteration, or by use of inhibitory RNAs (e.g., sense, antisense, or RNAi technology). A deletion may encompass all or part of a gene's coding sequence. The term "knockout" refers to the deletion of most (at least about 95%, at least about 96%, at least about 97%, at least about 98%, or at least about 99%) or all (100%) of the coding sequence of a gene.

As used herein, a "gene deletion" or "deletion mutation" is a mutation in which at least part of a sequence of the DNA making up the gene is missing. Thus, a "deletion" in reference to nucleic acids is a loss or replacement of genetic material resulting in a complete or partial disruption of the sequence of the DNA making up the gene. Any number of nucleotides can be deleted, from a single base to an entire piece of a chromosome. Thus, in some embodiments, the term "deletion" refers to the removal of a gene necessary for encoding a specific protein (e.g., a protease). In this case, the strain having this deletion can be referred to as a "deletion strain."

With respect to "homologs," reference to particular gene names is for illustration and not limitation. It is understood that gene names vary from organism to organism and reference to a gene name is not intended to be limiting, but is intended to encompass homologs (or analogous sequences) and polymorphic variants with similar function. In certain embodiments, the analogous or homologous sequence will have at least about 50%, at least about 60%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identity with the named gene or gene product.

"Identity" or "percent identity" in the context of two or more polypeptide sequences refers to two or more sequences or sub-sequences that are the same or have a specified percentage of amino acid residues that are the same. For example, the sequence can have a percent identity of at least about 50%, about 60%, about 70%, about 75%, about 80%, about 85%, about 90%, about 91%, about 92%, about 93%, about 94%, about 95%, about 96%, about 97%, about 98%, or about 99% over a specified region to a reference sequence when compared and aligned for maximum correspondence over a comparison window, or designated region as measured using a sequence comparison algorithms or by manual alignment and visual inspection.

Optimal alignment of sequences for comparison and determination of sequence identity can be determined by a sequence comparison algorithm or by visual inspection (see, generally, Ausubel et al., infra). When optimally aligning sequences and determining sequence identity by visual inspection, percent sequence identity is calculated as the number of residues of the test sequence that are identical to the reference sequence divided by the number of non-gap positions and multiplied by 100. When using a sequence comparison algorithm, test and reference sequences are entered into a computer, subsequence coordinates and sequence algorithm program parameters are designated. The sequence comparison algorithm then calculates the percent sequence identities for the test sequences relative to the reference sequence, based on the program parameters.

An algorithm that may be used to determine whether a polypeptide (such as a FAR or Fab enzyme) has sequence identity to a reference sequence is the BLAST algorithm, which is described in Altschul et al., 1990, *J. Mol. Biol.* 215:403-410, which is incorporated herein by reference. Software for performing BLAST analyses is publicly available through the National Center for Biotechnology Information (on the worldwide web at ncbi.nlm.nih.gov/). The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. For amino acid sequences, the BLASTP program uses as defaults a word size (W) of 3, an expectation (E) of 10, and the BLOSUM62 scoring matrix (see Henikoff & Henikoff, 1989, *Proc. Natl. Acad. Sci. USA* 89:10915). Other programs that may be used include the Needleman-Wunsch procedure, J. Mol. Biol. 48: 443-453 (1970), using blosum62, a Gap start penalty of 7 and gap extend penalty of 1; and gapped BLAST 2.0 (see Altschul, et al. 1997, Nucleic Acids Res., 25:3389-3402) both available to the public at the National Center for Biotechnology Information Website.

Multiple sequences can be aligned with each other by visual inspection or using a sequence comparison algorithm, such as PSI-BLAST (Altschul, et al., 1997, supra) or "T-Coffee" (Notredame et al., 2000, J. Mol. Bio. 302:205-17). T-Coffee alignments may be carried out using default parameters (T-Coffee Technical Documentation, Version 8.01, July 2009, WorldWideWeb.tcoffee.org), or Protein Align. In Protein Align, alignments are computed by optimizing a function based on residue similarity scores (obtained from applying an amino acid substitution matrix to pairs of aligned residues) and gap penalties. Penalties are imposed for introducing an extending gaps in one sequence with respect to another. The final optimized function value is referred to as the alignment score. When aligning multiple sequences, Protein Align optimizes the "sum of pairs" score, i.e., the sum of all the separate pairwise alignment scores.

As used herein, the term "culturing" refers to growing a population of microbial cells under suitable conditions using any suitable medium (e.g., liquid, solid, or semi-solid media).

The term "extracellular environment" means the aqueous solution surrounding a cell membrane, excluding the intracellular space. For example, a secreted enzyme or a compound is found in the extracellular environment. In some embodiments, the extracellular environment comprises the culture medium used to grow the cell.

The term "contacting" refers to combining an enzyme and a substrate under conditions in which the enzyme can act on the substrate. Those skilled in the art will recognize that mixing a solution containing an enzyme with a substrate will effect "contacting." Similarly, in the context of culturing microorganisms, culturing microorganisms in a media containing a substrate (e.g., a fermentable sugar) will effect "contacting" the microorganism with the substrate.

The term "fermentable sugars" refers to simple sugars (monosaccharides, disaccharides and short oligosaccharides) such as but not limited to glucose, xylose, galactose, arabinose, mannose and sucrose. Fermentable sugar is any sugar that a microorganism can utilize or ferment.

The terms "cleaning compositions" and "cleaning formulations" refer to compositions that find use in the removal of undesired compounds from items to be cleaning, such as fabric, dishes, contact lenses, other solid substrates, hair (shampoos), skin (soaps and creams), teeth (mouthwashes, toothpastes, etc.), etc. The terms further refer to any composition that is suited for cleaning, bleaching, disinfecting and/or sterilizing any object and/or surface. It is intended that the terms include, but are not limited to detergent compositions (e.g., laundry and fine fabric detergents), hard surface cleaning formulations (e.g., for glass, wood, ceramics and metal countertops, windows, etc.), oven cleaners, carpet cleaners, fabric fresheners, fabric softeners, hand and machine dish detergents, dish rinse aids, and textile and laundry pre-spotters. In addition, the terms encompass cleaning compositions for use in household and institutional use, including but not limited to liquid cleaning and disinfecting agents, such as anti-bacterial hand soaps and wipes, cleaning bars, mouthwashes, denture cleaners, car shampoos, bathroom cleaners, hair shampoos and conditioners/rinses for humans and other animals, shower gels, foam baths, etc. Indeed, it is not intended that the term be limited to any particular cleaning composition. The terms encompass any materials/compounds selected for the particular type of cleaning compositions desired and the form of the product (e.g., liquid, gel, granule, or spray), as long as the composition is compatible with the fatty alcohol(s) of the present invention. The specific selection of cleaning composition materials are readily made by considering the surface, item or fabric to be cleaned, and the desired form of the composition for the cleaning conditions during use.

2. FATTY ALCOHOL BIOSYNTHETIC GENES, POLYPEPTIDES AND VARIANTS

FabZ Polypeptides and fabZ Polynucleotides:

In certain embodiments, a polynucleotide sequence encoding a FabZ enzyme has been introduced into an engineered cell (e.g., a bacterial cell). For example, in one embodiment, the polynucleotide sequence encoding a FabZ enzyme is set forth herein as SEQ ID NO:7 and the encoded amino acid sequence is set forth as SEQ ID NO:8. In another embodiment, the polynucleotide sequence encoding a FabZ enzyme is set forth herein as SEQ ID NO:25 and the encoded amino acid sequence is set forth as SEQ ID NO:26. In some embodiments, the FabZ is encoded by a nucleic acid sequence that is at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to SEQ ID NO:7 or SEQ ID NO: 25. In some embodiments, the FabZ is encoded by a nucleic acid sequence that can selectively hybridize to SEQ ID NO:7 or SEQ ID NO: 25 under moderately stringent, stringent or highly stringent conditions, as described hereinabove. FabZ sequences can be identified by any of a variety of methods known in the art. For example, a sequence alignment can be conducted against a database, for example against the NCBI database, and sequences with the lowest HMM E-value can be selected. While both FabA and FabZ enzymes are 3-hydroxyacyl-ACP-dehydrases, the FabZ enzymes lack isomerase activity.

In some embodiments, the FabZ comprises an amino acid sequence that is a least about 80%, about 85%, about 86%, about 87%, about 88%, about 89%, about 90%, about 91%, about 92%, about 93%, about 94%, about 95%, about 96%, about 97%, about 98%, about 99%, or even about 100% identical to the amino acid sequence set forth in SEQ ID NO:8. In other embodiments, the FabZ comprises an amino acid sequence that is a least about 80%, about 85%, about 86%, about 87%, about 88%, about 89%, about 90%, about 91%, about 92%, about 93%, about 94%, about 95%, about 96%, about 97%, about 98%, about 99%, or even about 100% identical to the amino acid sequence set forth in SEQ ID NO:26. In some embodiments, the FabZ is a functional fragment of a sequence having at least about 90%, about 91%, about 92%, about 93%, about 94%, about 95%, about 96%, about 97%, about 98%, or about 99% the length of the sequence of SEQ ID NO:8 or SEQ ID NO: 26. In some embodiments, the FabZ is derived from a bacterial species such as *E. coli* or *Bacillus*. In other embodiments the FabZ is derived from photosynthetic bacterial such as *Rhodobacter* (for example, *R. capsulatus* or *R. sphaeroides*). In some embodiments, the FabZ is encoded by a *Rhodobacter capsulatus* fabZ.

Methods to measure the dehydratase activity of FabZ are known to those in the art (See e.g., Heath & Rock, 1996. J. Biol. Chem. 271: 27795-27801).

FabA Polypeptides and fabA Polynucleotides:

In certain embodiments a polynucleotide sequence encoding a FabA enzyme has been introduced into an engineered cell (e.g., a bacterial cell). For example, in one embodiment, the polynucleotide sequence encoding a FabA enzyme is set forth herein as SEQ ID NO:9, and the encoded amino acid sequence is set forth as SEQ ID NO:10. In some embodiments, the FabA is encoded by a nucleic acid sequence that is at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to SEQ ID NO:9. In some embodiments, the FabA is encoded by a nucleic acid sequence that can selectively hybridize to SEQ ID NO:9 under moderately stringent, stringent or highly stringent conditions, as described hereinabove. FabA sequences can be identified by any of a variety of methods known in the art. For example, a sequence alignment can be conducted against a database, for example against the NCBI database, and sequences with the lowest HMM E-value can be selected.

In some embodiments, the FabA comprises an amino acid sequence that is a least about 80%, about 85%, about 86%, about 87%, about 88%, about 89%, about 90%, about 91%, about 92%, about 93%, about 94%, about 95%, about 96%, about 97%, about 98%, about 99%, or even about 100% identical to the amino acid sequence set forth in SEQ ID NO:10. In some embodiments, the FabA is a functional fragment of a sequence having at least about 95% sequence identity to SEQ ID NO:10. In some embodiments, the functional fragment is about 90%, about 91%, about 92%, about 93%, about 94%, about 95%, about 96%, about 97%, about 98%, or about 99% the length of the sequence of SEQ ID NO:10. Methods to measure the dehydratase and isomerase activities of FabA are known (See e.g., Heath & Rock, supra).

FabI Polypeptides and fabI Polynucleotides:

In certain embodiments a polynucleotide sequence encoding a FabI enzyme has been introduced into an engineered cell (e.g., a bacterial cell). For example, in one embodiment, the polynucleotide sequence encoding a FabI enzyme is set forth herein as SEQ ID NO:11, and the encoded amino acid sequence is set forth as SEQ ID NO:12. The FabI (SEQ ID NO:11) and FabI (SEQ ID NO:12) are also referred to herein as "fabI1" and "FabI1."

In some embodiments, the FabI is encoded by a nucleic acid sequence that is at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to SEQ ID NO:11. In some embodiments, the FabI is encoded by a nucleic acid sequence that can selectively hybridize to SEQ ID NO:11 under moderately stringent, stringent or highly stringent conditions, as described hereinabove. FabI sequences can be identified by any of a variety of methods known in the art. For example, a sequence alignment can be conducted against a database, for example against the NCBI database, and sequences with the lowest HMM.

In some embodiments, the FabI comprises an amino acid sequence that is a least about 80%, about 85%, about 88%, about 90%, about 91%, about 92%, about 93%, about 94%, about 95%, about 96%, about 97%, about 98%, about 99%, even about 100% identical to the amino acid sequence set forth in SEQ ID NO:12. In some embodiments, the FabI is a functional fragment of a sequence having at least about 95% sequence identity to SEQ ID NO:12. In some embodiments, the functional fragment is about 90%, about 91%, about 92%, about 93%, about 94%, about 95%, about 96%, about 97%, about 98%, and about 99% the length of the sequence of SEQ ID NO:12. In certain embodiments, the FabI is encoded by a fabI gene found in *E. coli*, such as GenBank: AAC74370. In some embodiments, the FabI is encoded by a fabI gene found in *Rhodobacter capsulatus* SB1003 such as GenBank: AD86080 (fabI-1) and in other embodiments such as GenBank: ADE86397 (fabI-2). The percentage of amino acid identity between the *E. coli* FabI and the *R. capsulatus* FabI-1 is 49%, and the percent of amino acid identity between *E. coli* FabI and *R. capsulatus* FabI-2 is 45.6%. The percent amino acid sequence identity between *R. capsulatus* FabI-1 and *R. capsulatus* FabI-2 is 59.2%. Methods for measurement of enoyl-ACP reductase activity are known in the art (See e.g., Heath & Rock, 1995. J. Biol. Chem. 270: 26538-26542).

In certain embodiments, the engineered bacterial cell comprises a) a polynucleotide sequence encoding a FabZ enzyme as described hereinabove, and b) a polynucleotide sequence encoding a FabI enzyme as described herein above. In certain embodiments the FabZ enzyme comprises a polypeptide sequence having at least about 95%, about 96%, about 97%, about 98%, about 99%, or even about 100% sequence identity to SEQ ID NO:8 and the FabI enzyme comprises a polypeptide sequence having at least about 95%, about 96%, about 97%, about 98%, about 99%, or even about 100% sequence identity to SEQ ID NO:12.

In certain embodiments, the engineered bacterial cell comprises a) a polynucleotide sequence encoding a FabZ enzyme as described hereinabove, and b) a polynucleotide sequence encoding a FabI enzyme as described herein above. In certain embodiments the FabZ enzyme comprises a polypeptide sequence having at least about 95%, about 96%, about 97%, about 98%, about 99%, or even about 100% sequence identity to SEQ ID NO:26 and the FabI enzyme comprises a polypeptide sequence having at least about 95%, about 96%, about 97%, about 98%, about 99%, or even about 100% sequence identity to SEQ ID NO:12.

In certain embodiments, the engineered bacterial cell comprises a) a polynucleotide sequence encoding a FabA enzyme as described hereinabove and b) a polynucleotide sequence encoding a FabI enzyme as described herein above. In certain embodiments, the FabA enzyme comprises a polypeptide sequence having at least about 95%, about 96%, about 97%, about 98%, about 99%, and even about 100% sequence identity to SEQ ID NO:10 and the FabI enzyme comprises a polypeptide sequence having at least about 95%, about 96%, about 97%, about 98%, about 99%, or even about 100% sequence identity to SEQ ID NO:12.

In certain embodiments, the engineered bacterial cell comprises a) a heterologous polynucleotide encoding a FabZ enzyme comprising a polypeptide sequence having at least about 90%, (about 91%, about 92%, about 93%, about 94%, about 95%, about 96%, about 97%, about 98%, about 99% and even 100%) sequence identity to SEQ ID NO: 8 or SEQ ID NO: 26; b) a heterologous polynucleotide sequence encoding a FabA enzyme comprising a polypeptide sequence having at least about 95%, about 96%, about 97%, about 98%, about 99%, and even about 100% sequence identity to SEQ ID NO:10 and c) a heterologous polynucleotide encoding a FabI enzyme comprising a polypeptide sequence having at least about 95%, about 96%, about 97%, about 98%, about 99%, or even about 100% sequence identity to SEQ ID NO:12.

3. FATTY ALCOHOL REDUCTASE ENZYMES, POLYNUCLEOTIDES AND VARIANTS

The engineered host cells (e.g., an E. coli strain) encompassed by the invention are modified to express a polynucleotide encoding a heterologous FAR. Polynucleotides encoding FAR enzymes are known in the art (See e.g., WO2011/008535; WO2011/019858; U.S. Ser. No. 13/171,138, US2010/02036; U.S. Pat. No. 7,332,311; U.S. Pat. No. 6,143,538 and Metz et al., 2000, Plant Physiol. 122:635-644).

In some embodiments the acyl-CoA is reduced to a fatty alcohol in a two-step process. An NAD(P)H dependent acyl-CoA reductase converts an acyl-CoA to a fatty aldehyde and then the fatty aldehyde is reduced to a fatty alcohol by a NAD(P)H dependent alcohol dehydrogenase. Enzymes involved in this two-step conversion include the enzymes Acr1 and YqhD. (See, Reiser and Somerville, J. Bacteriol. (1997) 179:2969; Ishige et al., Appl. Environ. Microbiol. (2000) 66:3481; Hofrander et al. (2011) FEBS Letters 585:3538-3543 and Kalscheuer et al., 2006, Appl. Environ. Microbiol. 72:1373).

Preferred fatty alcohol forming acyl-CoA reductases (FARs) useful in the present invention catalyze the direct reduction of acyl-CoA and/or acyl-ACP substrates to fatty alcohols wherein free fatty aldehydes are essentially not released as an intermediate. In effect, these FARs reduce acyl chains to fatty alcohols by one enzymatic step. Depending on the substrate chain length, it is possible to have trace amounts of aldehydes produced and released. In the direct reduction process, FAR converts at least acyl-ACP substrates to a fatty alcohol end-product without the subsequent action of an alcohol dehydrogenase.

While not meant to limit the invention, in some embodiments the FAR is a prokaryotic enzyme. In some embodiments, the FAR is derived from a species of Marinobacter including but not limited to M. algicola, M. alkaliphilus, M. aquaeolei, M. arcticus, M. bryozoorum, M. daepoensis, M. excellens, M. flavimaris, M. guadonensis, M. hydrocarbonoclasticus, M. koreenis, M. lipolyticus, M. litoralis, M. lutaoensis, M. maritimus, M. sediminum, M. squalenivirans, and M. vinifirmus, and equivalent and synonymous species thereof.

In certain embodiments, the FAR is derived from M. algicola strain DG893 and has an amino acid sequence that is at least about 30% identical, at least about 40% identical, at least about 50% identical, at least about 60% identical, at least about 70% identical, at least about 75% identical, at least about 80% identical, at least about 85% identical, at least about 90% identical, at least about 93% identical, at least about 95% identical, at least about 97% identical, at least about 98% identical and/or at least about 99% identical to SEQ ID NO:2 and/or a functional fragment thereof. In another embodiment, the FAR enzyme has an amino acid sequence that is identical to SEQ ID NO:2. In certain embodiments, the FAR is a variant of the wild-type FAR of SEQ ID NO:2 which has at least 1, at least 2, at least 3, at least 4, at least 5, at least 6, at least 7, at least 8, at least 9, at least 10, at least 12, at least 14, at least 16, at least 18, at least 20, at least 25, at least 30 or more amino acid alterations (e.g., substitutions, deletions and/or insertions) relative to SEQ ID NO:2. In certain embodiments, the FAR has an amino acid sequence of at least about 90% (such as at least 93%, at least 95%, at least about 96%, at least about 97%, at least about 98%, or at least about 99% sequence identity to SEQ ID NO:4, SEQ ID NO:6 or SEQ ID NO: 28. In some embodiments, the variant FAR is FAR-V1 comprising an amino acid sequence of SEQ ID NO: 4 and in other embodiments the variant FAR is FAR-V2 comprising the amino acids sequence of SEQ ID NO: 6 and in further embodiments the variant FAR is FAR-V3 comprising SEQ ID NO: 28. In some embodiments, the variant FAR comprises at least 95% sequence identity to SEQ ID NO: 4, SEQ ID NO: 6 or SEQ ID NO: 28 and further comprises at least 1, at least 2, at least 3, at least 4, at least 5, at least 6, at least 7, at least 8, at least 9, at least 10 or more amino acid alterations. Indeed the current invention is not limited to the specifically exemplified FAR variants defined herein above and in the Examples, but include for example the FAR variants described in WO2012/006114, US provisional applications 61/578,673; 61/636,044 and 61/674,053 and PCT International Application No. PCT/US2012/069444. The disclosures of which are hereby specifically incorporated by reference.

In certain embodiments, the FAR is derived from Marinobacter aquaeolei and has an amino acid sequence that is at least about 30% identical, at least about 40%, at least about 50% identical, at least about 60% identical, at least about 70% identical, at least about 75%, at least about 80% identical, at least about 85% identical, at least about 90% identical, at least about 93% identical, at least about 95% identical, at least about 97% identical, at least about 98% identical and/or at least about 99% identical to SEQ ED NO:18 and/or a functional fragment thereof. In another specific embodiment, the isolated FAR enzyme has an amino acid sequence that is identical to SEQ ID NO:18. In certain embodiments, the FAR is a variant of the wild-type FAR of SEQ ID NO:18 that has at least 1, at least 2, at least 3, at least 4, at least 5, at least 6, at least 7, at least 8, at least 9, at least 10, at least 12, at least 14, at least 16, at least 18, at least 20, at least 25, at least 30 or more amino acid alterations (e.g., substitutions, deletions and/or insertions) relative to SEQ ID NO:18.

In other embodiments, the FAR is derived from Marinobacter aquaeolei and has an amino acid sequence that is at least about 70% identical, at least about 75%, at least about 80% identical, at least about 85% identical, at least about 90% identical, at least about 93% identical, at least about 95% identical, at least about 97% identical, at least about 98% identical and/or at least about 99% identical to SEQ ID NO: 5 as disclosed in WO 2012/006114 and/or a functional fragment thereof. In another specific embodiment, the FAR enzyme has an amino acid sequence that is identical to SEQ ID NO: 5. In certain embodiments, the FAR is a variant of the wild-type FAR of SEQ ID NO:5 that has at least 1, at least 2, at least 3, at least 4, at least 5, at least 6, at least 7, at least 8, at least 9, at least 10, at least 12, at least 14, at least 16, at least 18, at least 20, at least 25, at least 30 or more amino acid alterations (e.g., substitutions, deletions and/or insertions) relative to SEQ ID NO:5. In certain embodiments, the FAR is encoded by a polynucleotide sequence having at least 85% (at least 90%, 91%, 92%, 93%, 94%, 95%, 96%, 97%, 98%, 99% sequence identity to SEQ ID NO:4 as disclosed in WO 2012/006114.

In other embodiments, the FAR is derived from Marinobacter aquaeolei and has an amino acid sequence that is at least about 70% identical, at least about 75%, at least about 80% identical, at least about 85% identical, at least about 90% identical, at least about 93% identical, at least about 95% identical, at least about 97% identical, at least about 98% identical and/or at least about 99% identical to SEQ ID NO: 1 as disclosed in US 2012/0184006 and/or a functional fragment thereof (such as amino acid residue positions 1 to 364 or amino acid residue positions 365 to 591 of SEQ ID NO: 1). In another specific embodiment, the FAR enzyme has an amino acid sequence that is identical to SEQ ID NO:1 as disclosed in US 2012/0184006. In certain embodiments, the FAR is a variant of the wild-type FAR of SEQ ID NO:1 disclosed in US2012/0184006 that has at least 1, at least 2, at least 3, at least 4, at least 5, at least 6, at least 7, at least 8, at least 9, at least 10, at least 12, at least 14, at least 16, at least 18, at least 20, at least 25, at least 30 or more amino acid alterations (e.g., substitutions, deletions and/or insertions) relative to SEQ ID NO:1. In certain embodiments, the FAR is encoded by a polynucleotide sequence having at least 85% (at least 90%, 91%, 92%, 93%, 94%, 95%, 96%, 97%, 98%, 99% sequence identity to SEQ ID NO:2 as disclosed in US 2012/0184006.

In certain embodiments, the FAR is obtained from a marine bacterium selected from the group of *Meptuniibacter caesariensis* strain MED92, *Reinekea* sp. strain MED297, *Marinomonas* sp. strain MED121, unnamed gammaproteobacterium strain HTCC2207, and *Marinobacter* sp. strain ELB 17, as well as equivalents and synonymous species thereof. In certain embodiments, the FAR is obtained from the genus *Oceanobacter*. In some embodiments, the FAR is obtained from the *Oceanobacter* species strain RED65 and has an amino acid sequence that is at least about 30% identical, at least about 40% identical, at least about 50% identical, at least about 60% identical, at least about 65%, at least about 70% identical, at least about 75% identical, at least about 80% identical, at least about 85% identical, at least about 90% identical, at least about 93% identical, at least about 95% identical, at least about 97% identical, and/or at least about 98% identical to SEQ ID NOs:6 and/or 8 as disclosed in WO 2011/008535. In another specific embodiment, the FAR enzyme for use in the methods disclosed herein comprises or consists of a sequence having about 100% identity to the sequence of SEQ ID NO:6 ("FAR_Ocs"). In other specific embodiments, the isolated FAR enzyme or functional fragment is obtained or derived from *Oceanobacter kriegii*. In still other specific embodiments, the isolated FAR enzyme or functional fragment is obtained or derived from *Oceanobacter* strain WH099.

In various embodiments, the FAR is encoded by a polynucleotide selected from the group of FAR Hch (*Hahella chejuensis* KCTC 2396 GenBank YP_436183.1); FAR_Mac (from marine *Actinobacterium* strain PHSC20C1); FAR_JVC (JCVI_ORF_1096697648832, GenBank Accession No. EDD40059.1); FAR_Fer (JCVI_S-CAF_1101670217388); FAR Key (JCVI_S-CAF_1097205236585; FAR_Gal (JCVI_S-CAF_1101670289386); *Vitis vinifera* FAR (GenBank Accession No. CAO22305.1 or CAO67776.1); *Desulfatibacillum alkenivorans* FAR (GenBank Accession No. NZ_ABII01000018.1); *Stigmatella aurantiaca* FAR (NZ_AAMD01000005.1); *Phytophthora ramorum* FAR (GenBank Accession No.: AAQX01001105.1); GenBank Accession no. AAD38039.1; gi|5020215|gb|AAD38039.1|AF149917_1 acyl CoA reductase [*Simmondsia chinensis*]; GenBank Accession no. BAC79425.1; gi|33146307|dbj|BAC79425.1|fatty-acyl reductase [*Bombyx mori*]; GenBank Accession no. DQ446732.1 or NM_115529.1; gi|91806527|gb|DQ446732.1|*Arabidopsis thaliana* clone pENTR221-At3g44560; gi|18410556|ref|NM_115529.1|; and (GenBank Accession no. EU817405.1; gi|210063138|gb|EU817405.1|*Ostrinia scapulalis*.

As indicated herein, "heterologous FAR" encompasses wild-type FARs, variants and functional fragments thereof. In various embodiments, a functional fragment of a full-length wild-type FAR or a variant FAR comprises at least about 70%, at least about 75%, at least about 80%, at least about 90%, at least about 91%, at least about 92%, at least about 93%, at least about 94%, at least about 95%, at least about 96%, at least about 97%, at least about 98%, or at least about 99% identity to the wild-type or reference amino acid sequence. In certain embodiments, a functional fragment comprises about 75%, about 80%, about 85%, at about 90%, about 91%, about 92%, about 93%, about 94%, about 95%, about 96%, about 97%, about 98%, or about 99% of the amino acid sequence of a full-length FAR polypeptide (such as bit not limited to FAR-V1, FAR-V2 or FAR-V3).

In some embodiments, the preferred substrates for the heterologous FAR are fatty acyl-ACP substrates comprising carbon chain lengths of C10 to C20. In certain embodiments, the fatty acyl-ACP substrates comprise carbon chain lengths of C12 to C18, and in other embodiments, the fatty acyl-ACP substrates comprise carbon chain lengths of C12 to C16. In certain embodiments, the substrate comprises a majority of saturated hydrocarbons. In certain embodiments, the substrate pool for the heterologous FAR comprises over about 80% (e.g., 85%, 90%, 92%, 94%, 95%, 96%, 97%, and 98%) C12 to C18 fatty acyl-ACP substrates. In other embodiments, the heterologous FAR catalyzes the reduction of fatty acyl CoA substrates to the corresponding fatty alcohol. In certain embodiments, the fatty acyl CoA substrate pool comprises over about 70% (e.g., about 75%, 80%, 85%, 88%, 90%, 92%, 94%, 95%, 96%, 97%, 98% and 99%) C10 to C18 fatty acyl CoA substrates, over about 70% (e.g., about 75%, 80%, 85%, 88%, 90%, 92%, 94%, 95%, 96%, 97%, 98% and 99%) C10 to C16 fatty acyl-CoA substrates; and also over about 70% (e.g., about 75%, 80%, 85%, 88%, 90%, 92%, 94%, 95%, 96%, 97%, 98% and 99%) C12 to C16 fatty acyl-CoA substrates. In certain embodiments, the substrate pool for the heterologous FAR comprises over about 80% (e.g., about 85%, about 90%, or about 95%) C12 to C18 fatty acyl-CoA substrates. In certain embodiments, the C10 to C18 fatty acyl substrates comprises a majority of saturated hydrocarbons.

In some embodiments, the engineered bacterial microorganisms comprise i) a polynucleotide sequence encoding a heterologous FAR, wherein the heterologous FAR has at least 90% (e.g., at least 90%, at least 91%, at least 92%, at least 93%, at least 94%, at least 95%, at least 96%, at least 97%, at least 98% and at least 99%) sequence identity to SEQ ID NO: 28; ii) optionally a first polynucleotide sequence encoding a heterologous FabI, wherein the heterologous FabI has at least 90% (e.g., at least 90%, at least 91%, at least 92%, at least 93%, at least 94%, at least 95%, at least 96%, at least 97%, at least 98% and at least 99%) sequence identity to SEQ ID NO:12 and iii) optionally a second polynucleotide sequence encoding a heterologous FabZ, wherein the heterologous FabZ has at least (e.g., at least 90%, at least 91%, at least 92%, at least 93%, at least 94%, at least 95%, at least 96%, at least 97%, at least 98% and at least 99%) sequence identity to SEQ ID NO: 8 or SEQ ID NO: 26. In some embodiments, the engineered bacterial microorganism comprises either the first polynucleotide encoding a heterologous FabI or the second polynucleotide encoding a heterologous FabZ. In some embodiments, the engineered bacterial microorganism includes both the first polynucleotide encoding FabI and the second polynucleotide encoding FabZ.

4. EMBODIMENTS INCLUDING THIOESTERASE

Thioesterase:

According to one embodiment of the invention, a microbial host cell is engineered to express a heterologous thioesterase ("TE"). The thioesterase may be one that preferentially uses C12, C14 or C16 ACPs. Depending on the TE used a homogenous population of fatty alcohols may be produced. For example, if the TE is one that predominantly uses C12 ACPs then the fatty alcohol composition produced by a recombinant microbial cell according to the invention will predominantly comprise fatty alcohols having a carbon chain length of C12. In some embodiments, preferred TEs are those that are classified as TE from the Family TE14 in the ThYme database. These sequences may be downloaded from GenBank and UniProt databases (Nucleic Acid Res 201038:D142-D148).

Some nonlimiting examples of TEs that may be used include the "class I" and "class II" acyl-ACP TE fat genes (e.g. fatA or fatB genes and reference is made to A. Jones et al., 1995, Plant Cell 7:359-371). In particular, FatB are preferred TEs (e.g. plant acyl-ACP TEs) useful in the invention. In some embodiments, the TE may be a bacterial acyl-ACP TE. FatB may be obtained for example from *Umbellularia california* having Accession number Q41635; and AAA34215; *Ulmus americana* having Accession number AAB71731, *Cuphea hookeriana* Accession numbers Q39513; AAC49269; AAC49269; and AAC72881; *Cinnamonum camphorum* having Accession number Q39473; AAC49151; and acyl-ACP thioesterases from *Cuphea palustris* (AAC49179; and U.S. Pat. No. 5,955,329). Other TEs include without limitation CnFatB (*Cocos nucifera*, e.g. JF338903; JF338904 and JF338905); ccFAT (*Cinnamomum camphora*); pdFat (*Parabacteroides distasonis*, ATCC 8503); gsFat (*Geobacillus* sp. Y412MC10); pvFAT (*Paenibacillus vortex* V453); pm FAT (*Parabacteroides merdae* ATCC 43184); cvFatB (*Cuphea viscosissima*, JF338906; JF338907; and JF338908); eoFat (*Elaeis oleifera*) AAD42220 (*Elaeis guineensis*) and mlFat (*Madhuca longofolia* var. *latifolia*).

In some embodiments, homologous or analogous TE genes will be used for the heterologous expression of a TE enzyme.

It is known that different acyl-ACP TE have different degrees of chain length specificity. In some preferred embodiments, the TE useful in the invention is a TE having a preference for cleaving chain lengths of any one of C12, C14 and/or C16 fatty acids from ACP. In some embodiments, having a preference for cleaving chain lengths of any one of C12, C14 and/or C16 fatty acids from ACP means that the thioester hydrolysis will produce fatty acids having at least 85%, (such as at least 88%, 90%, 93%, 95%, 96% or more) of any one of C12, C14 and/or C16 carbon chain lengths.

In one embodiment, the TE is encoded by a gene comprising the polynucleotide sequence having at least 70%, (at least 75%, 80%, 85%, 90%, 93%, 95%, 97%, 99%, and even 100%) sequence identity to the polynucleotide sequence of SEQ ID NO: 21. In some embodiments, the TE enzyme will comprise at least 70%, (at least 75%, 80%, 85%, 90%, 93%, 95%, 97%, 99%, and even 100%) sequence identity to the polypeptide sequence of SEQ ID NO: 22. In some embodiments, the TE gene will comprise at least 85% sequence identity to the polynucleotide sequence of SEQ ID NO: 21. In some embodiments, the TE enzyme will comprise at least 85% sequence identity to the polypeptide sequence of SEQ ID NO: 22. In some embodiments, the TE gene will comprise at least 97% sequence identity to the polynucleotide sequence of SEQ ID NO: 21. In some embodiments, the TE enzyme will comprise at least 97% sequence identity to the polypeptide sequence of SEQ ID NO: 22. In some embodiments, the TE gene will comprise at least 99% sequence identity to the polynucleotide sequence of SEQ ID NO: 21. In some embodiments, the TE enzyme will comprise at least 99% sequence identity to the polypeptide sequence of SEQ ID NO: 22. In some embodiments, the TE gene will comprise the polynucleotide sequence of SEQ ID NO: 21. In some embodiments, the TE enzyme will comprise the polypeptide sequence of SEQ ID NO: 22. In some embodiments the gene encoding the TE enzyme is derived from *Umbelluria californica* (California Bay) and in other embodiments the gene encoding the TE enzyme is derived from *Cinnamomum camphorum*.

In some embodiments, the TE enzyme will be a functional fragment of a reference (e.g. native) TE, such as a TE having deletions at the N-terminal amino acid positions. In certain embodiments, the functional fragment will comprise at least 95% of the reference enzyme. In certain embodiments, the functional fragment will include a deletion of at least 1, 2, 3, 4, 5, 6, 7, 8, 9, 10 or more amino acid residues. In some embodiments, the TE is a variant enzyme having at least 1, at least 5, at least 10, at least 15 or more amino acid modifications, such as substitutions. Non-limiting examples include the TE FatB genes from California Bay, *Cinnamomun camphora*, or from various *Cuphea* species such as those disclosed in WO 2011/008565 and reference is made to SEQ ID NOs. 21, 48, 52, 56, 60, 64, 66, 70, 72, 76, 80, 82, 86, 90, 92, 94, 96 and 100 described therein.

Further acyl-ACP TEs that are useful according to the invention are described in the following references: U.S. Pat. No. 5,344,771; U.S. Pat. No. 5,512,482; U.S. Pat. No. 6,150,512; U.S. Pat. No. 5,723,761; U.S. Pat. No. 5,910,631 and WO2010/075483.

Various assays are known which can be used to test for TE activity in a recombinant microorganism transformed with a vector comprising a polynucleotide encoding a TE according to the invention (See, Voelker and Davies, 1994, J. Bacteriol. 76:7320).

Acyl-CoA Synthetase:

As described above, the term "acyl-CoA synthetase" is used synonymously with ACS, acyl-CoA synthetase and FadD. These enzymes mediate the formation of acyl-CoA esters (see FIG. 1). According to an embodiment of the invention, a microbial host cell is engineered to express a recombinant ACS. ACSs that can be expressed to produce acyl-CoA include the *E. coli* fadD gene comprising the polynucleotide sequence of SEQ ID NO: 19 which encodes the ACS comprising the polypeptide sequence of SEQ ID NO: 6. In some embodiments, the fadD gene will comprise at least 70%, (at least 75%, 80%, 85%, 90%, 93%, 95%, 97%, 99%, and even 100%) sequence identity to the polynucleotide sequence of SEQ ID NO: 19. In some embodiments, the ACS enzyme will comprise at least 70%, (at least 75%, 80%, 85%, 90%, 93%, 95%, 97%, 99%, and even 100%) sequence identity to the polypeptide sequence of SEQ ID NO: 20. In some embodiments, the fadD gene will comprise at least 85% sequence identity to the polynucleotide sequence of SEQ ED NO: 19. In some embodiments, the ACS enzyme will comprise at least 85% sequence identity to the polypeptide sequence of SEQ ID NO: 20. In some embodiments, the fadD gene will comprise at least 97% sequence identity to the polynucleotide sequence of SEQ ID NO: 19. In some embodiments, the ACS enzyme will comprise at least 97% sequence identity to the polypeptide sequence of SEQ ID NO: 20. In some embodiments, the fadD gene will comprise the polynucleotide sequence of SEQ ID NO: 19. In some embodiments, the ACS enzyme will comprise the polypeptide sequence of SEQ ID NO: 20.

In some embodiments, fadD encodes an ACS variant enzyme having at least 1, at least 5, at least 10, at least 15 or more amino acid modifications, such as substitutions. Non-limiting examples include modifications to the gene encoding the ACS of SEQ ID NO: 20.

In some embodiments, homologous fadD genes will be used for the heterologous expression of an ACS enzyme to produce acyl-CoAs. These fadD genes include without limitation, fadD from *Acinetobacter* sp. NCBI ID YP_045024; fadD from *Haemophilus influenza* NCBI ID NP_438551; fadD from *Pseudomonas aeruginosa* NCBI ID_251989 and 251990; BH3101 from *Bacillus halodurans* NP_243969; yhfL from *Bacillus subtilis* NP_388908; and fadD from *Rhizobium etli* CFN NCBI ID_ 533919; fadD from *Marinobacter algicola* ZP_01892995; fadD from *Marinobacter aquaeolei* YP_958864; fadD from *Mycobacterium tuberculosis* NP_215722; fadD15 from *Mycobacterium tuberculosis* NP 216703; fadD19 from *Mycobacterium tuberculosis* YP_177983; fadD from *Rhodopseudomonas palustris* YP_00993712; fadD from *Pseudomonas fluorscens* PfO-1 YP_350081; fadD from *Pseudomonas putida* ACC77300; fadK from *E. coli* strain W ZP_07590374; putative fadK from *Salmonella typhimurium* LT2 NP 460316; and putative fadK from *Thermomonospora fusca* YP_290214.

In some embodiments, the engineered bacterial cell according to the invention comprises (i) one or more heterologous polynucleotides encoding a polypeptide selected from a) a FabZ enzyme comprising a polypeptide sequence having at least about 95%, about 96%, about 97%, about 98%, about 99%, or even about 100% sequence identity to SEQ ID NO:8; b) a FabI enzyme comprising a polypeptide sequence having at least about 95%, about 96%, about 97%, about 98%, about 99%, or even about 100% sequence identity to SEQ ID NO:12; c) a FabA enzyme comprising a polypeptide sequence having at least about 95%, about 96%, about 97%, about 98%, about 99%, and even about 100% sequence identity to SEQ ID NO:10, and d) a FabZ enzyme comprising a polypeptide sequence having at least about 95%, about 96%, about 97%, about 98%, about 99% or even 100%) sequence identity to SEQ ID NO: 26; (ii) a heterologous polynucleotide sequence encoding a TE comprising at least 70%, (at least 75%, 80%, 85%, 90%, 93%, 95%, 97%, 99%, and even 100%) sequence identity to the polypeptide sequence of SEQ ID NO: 22 and (iii) optionally a heterologous polynucleotide sequence encoding a FadD enzyme comprising at least 70%, (at least 75%, 80%, 85%, 90%, 93%, 95%, 97%, 99%, and even 100%) sequence identity to the polypeptide sequence of SEQ ID NO: 20.

5. DNA CONSTRUCTS, VECTORS AND TRANSFORMATION

In another aspect, the present invention provides polynucleotides encoding the enzymes as described above (e.g. FAR, Fab, Fad and TE enzymes). The polynucleotide can be a DNA or RNA and can be single-stranded or double-stranded. The polynucleotide can be isolated from a naturally occurring microorganism, or prepared wholly or partially via synthetic means. Indeed, it is intended that the polynucleotides of the present invention be produced using any suitable methods and components as known in the art.

In various aspects of the invention, the availability of a polypeptide sequence of a specific enzyme (such as a FAR, fab, fad or TE enzyme) provides a description of all polynucleotides capable of encoding the polypeptide of the known sequence because of the known correspondence of particular codons and the amino acids they encode. In certain embodiments, the degeneracy of the genetic code is used to produce a large number of polynucleotides that encode the polypeptides described herein. In some embodiments, the polynucleotides encoding the desired enzyme are codon-optimized. In some embodiments, the FAR polynucleotides encoding the FAR enzymes described herein are codon-optimized for expression in a recombinant host cells. In particular embodiments, the polynucleotides that encode the FAR enzymes described herein are codon-optimized for expression in a bacterial host cell. In some embodiments, the polynucleotides are codon-optimized for any desired property.

In certain embodiments, the present disclosure provides a vector or DNA construct comprising a polynucleotide encoding a FAR enzyme as described above, wherein the FAR is produced in a host cell. In some embodiments, the polynucleotide is a codon-optimized polynucleotide, such as a polynucleotide having at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or even about 100% sequence identity to SEQ ID NO:1, SEQ ID NO:3, SEQ ID NO:5, SEQ ID NO: 17 and/or SEQ ID NO:27 and further hybridizes with SEQ ED NO:1, SEQ ID NO: 3, SEQ ID NO:5, SEQ ID NO: 17 and/or SEQ ID NO:27 under medium, medium-high, high or very high stringency conditions.

Any suitable DNA construct and vector finds use in the invention (See e.g., WO 2011/008535 which is here in incorporated by reference). In some embodiments, the polynucleotide encodes for a variant FAR enzyme and the polynucleotide sequence will have at least about 90%, at least about 91%, at least about 92%, at least 93%, at least about 94%, at least about 95%, at least about 96%, at least about 97%, at least about 98%, at least about 99%, or even about 100%) sequence identity to SEQ ID NO:3, SEQ ID NO: 5 and/or SEQ ID NO:27. In some other embodiments, the variant FAR encoded by the polynucleotide sequence has at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or even about 100%) sequence identity to SEQ ID NO:4, SEQ ID NO: 6 and/or SEQ ID NO:28.

In other embodiments, a FAR enzyme is encoded by a polynucleotide sequence that has at least about 70%, at least about 75%, at least about 80%, at least about 85%, at least about 90%, at least about 93%, at least about 95%, at least about 96%, at least about 97%, or at least about 99% sequence identity to SEQ ID NO:1, SEQ ID NO:3, SEQ ID NO:5, SEQ ID NO: 17 and/or SEQ ID NO:27 and further hybridizes with SEQ ID NO:1, SEQ ID NO:3, SEQ ID NO:5, SEQ ID NO: 17 and/or SEQ ID NO:27 under medium, medium-high, high or very high stringency conditions.

In some embodiments, the polynucleotide encodes for a FabZ enzyme and the polynucleotide sequence will have at least about 90%, at least about 91%, at least about 92%, at least about 93%, at least about 94%, at least about 95%, at least about 96%, at least about 97%, at least about 98%, at least about 99%, or even about 100%) sequence identity to SEQ ID NO:7 and/or SEQ ID NO:25. In some embodiments, the polynucleotide encodes for a FabA enzyme and the polynucleotide sequence will have at least about 90%, at least about 91%, at least about 92%, at least about 93%, at least about 94%, at least about 95%, at least about 96%, at least about 97%, at least about 98%, at least about 99%, or even about 100%) sequence identity to SEQ ID NO:9. In some embodiments, the polynucleotide encodes for a FabI enzyme and the polynucleotide sequence will have at least about 90%, at least about 91%, at least about 92%, at least about 93%, at least about 94%, at least about 95%, at least about 96%, at least about 97%, at least about 98%, at least about 99%, or even about 100%) sequence identity to SEQ ID NO:11. In some embodiments, the polynucleotide encodes for a TE enzyme and the polynucleotide sequence will have at least about 90%, at least about 91%, at least about 92%, at least about 93%, at least about 94%, at least about 95%, at least about 96%, at least about 97%, at least about 98%, at least about 99%, or even about 100%) sequence identity to SEQ ID NO:21.

In some embodiments, polynucleotides encoding any of the enzymes as described herein (such as but not limited to FabZ, FabI, FabA, FAR and TE) for expression in the recombinant host cells are operably linked to a promoter, and optionally, to other control sequences.

Suitable promoters include, but are not limited to constitutive promoters, regulated promoters, and inducible promoters. Appropriate promoter sequences can be obtained from genes encoding extracellular or intracellular polypeptides which are either endogenous or heterologous to the host cell. Methods for the isolation, identification and manipulation of promoters of varying strengths are available in or readily adapted from the art. See e.g., Nevoigt et al. (2006) *Appl. Environ. Microbiol.* 72:5266-5273, the disclosure of which is herein incorporated by reference in its entirety.

In certain embodiments, the DNA constructs, vectors and polynucleotides are suitable for expression of a heterologous FabZ, FabI, FabA, FAR or TE enzyme in bacteria. For bacterial host cells, suitable promoters for directing transcription of the nucleic acid constructs of the present disclosure, include, but are not limited to the promoters obtained or derived the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, *Bacillus megaterium* promoters, and prokaryotic beta-lactamase gene (Villa-Kamaroff et al., *Proc. Natl Acad. Sci. USA* 75: 3727-3731(1978)), as well as the tac promoter (DeBoer et al., *Proc. Natl Acad. Sci. USA* 80: 21-25(1993)). Additional promoters include trp promoter, phage lambda PL, T7 promoter, promoters found at PromEC (http://margalit.huji.ac.il/promec/index.html) and the like. Particularly useful promoters include the Trc promoter (Brosius J. et al., (1985) J. Biol. Chem. 260: 3539-3541). Additional promoters suitable for use in the present disclosure are described in Terpe H., 2006, Appl. Microbiol. Biotechnol. 72:211-222 and in Sambrook et al (2001) *Molecular Cloning: A Laboratory Manual*, 3$^{rd}$ ed., Cold Spring Harbor Laboratory Press, New York. In some instances it may be advantageous to express the heterologous enzymes, such as the FAR and/or FabZ, FabI or FabA at certain stages during the engineered microorganisms growth cycle. In these cases the heterologous gene may be operably linked to an inducible promoter. Inducible promoters are known in the art. The lac, tac and trc promoters mentioned above are inducible promoters which are induced by the addition of isopropyl β-D-1-thiogalactopyranoside (IPTG).

In various embodiments, an expression vector optionally contains a ribosome binding site (RBS) for translation initiation, and a transcription terminator, such as the transcriptional terminators $T_1$ and $T_2$ derived from the rrnB operon from *E. coli* (See e.g., Orosz et al., (1991) Eur. J. Biochem. 201: 653-659). The vector also optionally includes appropriate sequences for amplifying expression, e.g., translational enhancers.

In various embodiments, the polynucleotides useful for expressing the heterologous enzymes in recombinant host cells are operably linked to other control sequences, including but not limited to, a transcription terminator sequence, a signal sequence that when translated directs the expressed polypeptide into the secretory pathway of the recombinant host cell, and/or a polyadenylation sequence (eukaryotes). The choice of appropriate control sequences for use in the polynucleotide constructs of the present disclosure is within the skill in the art and in various embodiments is dependent on the recombinant host cell used and the desired method of recovering the fatty alcohol compositions produced. Indeed, it is not intended that the present invention be limited to any particular control sequence(s).

A recombinant expression vector according to the invention can be any suitable vector, e.g., a plasmid or a virus, which can be manipulated by recombinant DNA techniques to facilitate expression of at least one heterologous enzyme in the recombinant host cell. In certain embodiments, the expression vector is integrated into the chromosome of the recombinant host cell and comprises one or more heterologous genes operably linked to one or more control sequences useful for production of at least one heterologous enzyme. In other embodiments, the expression vector is an extra chromosomal replicative DNA molecule, e.g., a linear or closed circular plasmid, that is found either in low copy number (e.g., from about 1 to about 10 copies per genome equivalent) or in high copy number (e.g., more than about 10 copies per genome equivalent). In various embodiments, the expression vector includes a selectable marker, such as a gene that confers antibiotic resistance (e.g., ampicillin, kanamycin, chloramphenicol or tetracycline resistance) to the recombinant host organism that comprises the vector.

Expression vectors which, in certain embodiments, are useful for expressing enzymes as disclosed herein (for example FabZ, FabI, FAR and TE) are commercially available, e.g., from Sigma-Aldrich Chemicals, St. Louis Mo. and Stratagene, LaJolla Calif. In some embodiments, examples of suitable expression vectors are plasmids which are derived from pBR322 (Gibco BRL), pUC (Gibco BRL), pREP4, pCEP4 (Invitrogen) or pPoly (Lathe et al., 1987, *Gene* 57:193-201). In some embodiments, the expression vector comprising a polynucleotide sequence encoding the FAR enzyme and the expression vector comprising a polynucleotide sequence encoding one or more other enzymes, such as but not limited to, a Fab enzyme (e.g., FabZ or FabI) are on separate vectors. In other embodiments, the polynucleotide sequence encoding a heterologous FAR enzyme and the polynucleotide sequence encoding one or more other enzymes such as but not limited to a Fab enzyme are encoded on the same expression vector, and expression of each enzyme is may be independently regulated by a different promoter. In some further embodiments, the polynucleotide sequence encoding the heterologous FAR enzyme and the heterologous Fab enzyme are found on the same expression vector, and expression of each enzyme is regulated by the same promoter.

In certain embodiments, the present disclosure provides a plasmid for expression of heterologous genes in *E. coli*. Expression vector pCK110900, which comprises a P15A origin of replication "ori" (P15A ori), lac a CAP binding site, a lac promoter, a T7 ribosomal binding site (T7g10 RBS) and a chloramphenicol resistance gene (camR) is an exemplary vector that finds use in the present invention. This expression vector is depicted in FIG. 3 of U.S. Patent Publication No. 2006/0195947, which is incorporated herein by reference in its entirety. Other suitable plasmid vectors include, but are not limited to derivatives of pCL1920 and pCL1921 (Lerner and Inouye, 1990; NAR 18:4631). These vectors contain the pSC101 ori and confer resistance to spectinomycin (GenBank:AB236930). In some embodiments, the vector is an expression vector derived from pCL1920 including the Trc promoter and the lacIq gene from *E. coli*.

Methods, reagents and tools for transforming host cells described herein, such as bacteria, yeast (including oleaginous yeast) and filamentous fungi are known in the art. General methods, reagents and tools for transforming, e.g., bacteria can be found, for example, in Sambrook et al (2001) *Molecular Cloning: A Laboratory Manual*, 3$^{rd}$ ed., Cold Spring Harbor Laboratory Press, New York. Methods, reagents and tools for transforming yeast are described in "Guide to Yeast Genetics and Molecular Biology," C. Guthrie and G. Fink, Eds., *Methods in Enzymology* 350 (Academic Press, San Diego, 2002). Methods, reagents and tools for transforming *Y. lipolytica* are found in "*Yarrowia lipolytica*," C. Madzak, J. M. Nicaud and C. Gaillardin in "Production of Recombinant Proteins Novel Microbial and Eucaryotic Expression Systems," G. Gellissen, Ed. 2005. In some embodiments, introduction of the DNA construct or vector of the present invention into a host cell is accomplished by calcium phosphate transfection, DEAE-dextran mediated transfection, electroporation, or other common techniques (See Davis et al., 1986, *Basic Methods in Molecular Biology*, which is incorporated herein by reference). In one embodiment, a preferred method used to transform *E. coli* strains is electroporation and reference is made to Dower et al., 1988) NAR 16: 6127-6145. Indeed, any suitable method for transforming host cells finds use in the present invention. It is not intended that the present invention be limited to any particular method for introducing nucleic acids such as constructs into host cells.

The present invention also provides a method for producing a recombinant host cell, comprising: (a) providing at least one nucleic acid construct comprising at least one polynucleotide sequence encoding a) a FabZ, a FabA and/or FabI enzyme operably linked to a promoter; and (b) transforming a host cell with the nucleic acid construct(s) to produce a recombinant cell. In some embodiments, the host cell is a bacterial cell and in other embodiments, the host cell is *E. coli*. In some embodiments, the host cell already comprises a polynucleotide sequence encoding a heterologous FAR enzyme as described herein (i.e., the host cell comprises the FAR sequence prior to transformation). In some other embodiments, the FAR polynucleotide and the fab genes (e.g. fabZ, fabZ-fabI, fabA or fabA-fabI) will be on the same DNA construct or vector.

6. METHODS FOR GENE INACTIVATION AND EMBODIMENTS INCLUDING INACTIVATED FAB AND FAD GENES

In some embodiments, endogenous genes of the engineered microorganism of the present invention have been inactivated. For example in some embodiments, engineered microorganisms have been genetically modified to at least partially delete a gene encoding an endogenous enzyme (e.g., FabF, FadE or FadR). Typically, these modifications of the gene reduce or eliminate the total amount of endogenous enzyme produced by the host cell. In some embodiments, complete or near-complete deletion of the gene sequence is contemplated. However, a deletion mutation need not completely remove the entire gene sequence encoding the enzyme, in order to reduce the amount of endogenous enzyme produced by the engineered cell. For example, in some embodiments, there is a partial deletion that removes one or more nucleotides encoding a portion of an enzyme that plays a role in endogenous enzyme activity by the host cell (See, U.S. Pat. No. 8,110,670).

A deletion in a gene encoding an enzyme (e.g., FabF, FadE or FadR) in accordance with the embodiments provided herein includes a deletion of one or more nucleotides in the gene encoding the target enzyme. In some embodiments, there is a deletion of at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or about 100%, of the gene (e.g. a gene encoding for example FabF, FadE or FadR), wherein the amount of enzyme produced by the cell is reduced.

Thus, in some embodiments, the deletion results in at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about a 99% reduction in the enzyme activity produced by the cell, relative to the enzyme activity of a corresponding enzyme produced by an unmodified organism grown or cultured under essentially the same culture conditions and including the gene coding for the corresponding enzyme which had not be inactivated or deleted. In some embodiments, deletion is of a fabB gene or fadR gene.

Inactivation, such as a deletion, of a gene of interest (e.g., a fadE, a fabF, a fabB gene or a fadR gene) can be detected and confirmed by any of a variety of methods known in the art, including the methods provided herein. For example, gene deletion can be confirmed using PCR amplification of the modified genomic region. It will be appreciated that additional suitable techniques for confirming deletion can be used and are well known, including but not limited to Southern blot techniques, DNA sequencing of the modified genomic region, and screening for positive or negative markers incorporated during recombination events.

Some additional methods for complete and/or partial deletion of a gene are well-known. The genetically modified cells described herein can be generated using any of a variety of deletion methods known in the art that result in the complete inactivation or at least a reduction in the amount of at least one endogenous gene expressed by the cells. There are numerous approaches to create genetic modifications in bacteria (See e.g., Court et al., (2002) Annual Rev. Genet 36:361-388; and Datsenko and Wanner (2000) PNAS 97:6640-6645).

In certain embodiments the inactivation is of a fabF polynucleotide sequence encoding a FabF enzyme, For example, in one embodiment, the polynucleotide sequence encoding a FabF enzyme is set forth herein as SEQ ID NO: 13 and the encoded amino acid sequence is set forth as SEQ ID NO: 14. In some embodiments, the FabF is encoded by a nucleic acid sequence that is at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to SEQ ID NO:13. In some embodiments, the FabF is encoded by a nucleic acid sequence that can selectively hybridize to SEQ ID NO:13 under moderately stringent or highly stringent conditions, as described hereinabove. In some embodiments, the FabF enzyme has an amino acid sequence that is at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to SEQ ID NO:14. FabF sequences can be identified by any of a variety of methods known in the art. For example, a sequence alignment can be conducted against a database, for example against the NCBI database, and sequences with the lowest HMM E-value can be selected.

In certain embodiments the inactivation is of a fadR polynucleotide sequence encoding a FadR enzyme. For example, in one embodiment, the polynucleotide sequence encoding a FadR enzyme is set forth herein as SEQ ID NO:15, and the encoded amino acid sequence is set forth as SEQ ID NO:16. In some embodiments, the FadR is encoded by a nucleic acid sequence that is at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to SEQ ID NO:15. In some embodiments, the FadR is encoded by a nucleic acid sequence that can selectively hybridize to SEQ ID NO:15 under moderately stringent or highly stringent conditions, as described hereinabove. In some embodiments, the FadR has an amino acid sequence that is at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to SEQ ID NO:16. FadR sequences can be identified by any of a variety of methods known in the art. For example, a sequence alignment can be conducted against a database, for example against the NCBI database, and sequences with the lowest HMM E-value can be selected.

In certain embodiments, an engineered cell of the invention (e.g., *E. coli*) comprises a polynucleotide sequence encoding a FAR enzyme comprising an amino acid sequence that is at least about 30% identical, at least about 40%, at least about 50% identical, at least about 60% identical, at least about 70% identical, at least about 75%, at least about 80% identical, at least about 85% identical, at least about 90% identical, at least about 93% identical, at least about 95% identical, at least about 97% identical, at least about 98% identical, and/or at least about 99% identical to SEQ ID NO:2 and/or a functional fragment thereof and an inactivated gene encoding a FabF enzyme having at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% sequence identity to SEQ ID NO:14. In another embodiment, the engineered cell of the invention comprises a polynucleotide sequence encoding a FAR enzyme comprising an amino acid sequence that is at least about 95% identical, at least about 97% identical, at least about 98% identical, and/or at least about 99% identical to SEQ ID NOS:4 or 6 or a functional fragment thereof, and an inactivated gene encoding a FabF enzyme having at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% sequence identity to SEQ ID NO:14.

In certain embodiments, an engineered cell of the invention (e.g., *E. coli*) comprises a polynucleotide sequence encoding a FAR enzyme comprising an amino acid sequence that is at least about 30% identical, at least about 40% identical, at least about 50% identical, at least about 60% identical, at least about 70% identical, at least about 75%, at least about 80% identical, at least about 85% identical, at least about 90% identical, at least about 93% identical, at least about 95% identical, at least about 97% identical, at least about 98% identical and/or at least about 99% identical to SEQ ID NO:2, and/or a functional fragment thereof and an inactivated gene encoding a FadR enzyme having at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% sequence identity to SEQ ID NO:16. In another embodiment, the engineered cell of the invention comprises a polynucleotide sequence encoding a FAR enzyme comprising an amino acid sequence that is at least about 95% identical, at least about 97% identical, at least about 98% identical, and/or at least about 99% identical to SEQ ID NOS:4 and/or 6, and/or a functional fragment thereof and an inactivated gene encoding a FadR enzyme having at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to SEQ ID NO:16.

In certain embodiments, an engineered cell of the invention (e.g., *E. coli*) comprises a polynucleotide sequence encoding a FAR enzyme comprising an amino acid sequence that is at least about 30% identical, at least about 40%, at least about 50% identical, at least about 60% identical, at least about 70% identical, at least about 75%, at least about 80% identical, at least about 85% identical, at least about 90% identical, at least about 93% identical at least about 95% identical, at least about 97% identical, at least about 98% identical, and/or at least about 99% identical to SEQ ID NO:2 and/or a functional fragment thereof; an inactivated gene encoding a FadR enzyme having at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% sequence identity to SEQ ID NO:16; and in activated gene encoding a FabF enzyme having at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% sequence identity to SEQ ID NO:14. In another embodiment, the engineered cell of the invention comprises a polynucleotide sequence encoding a FAR enzyme comprising an amino acid sequence that is at least about 95% identical, at least about 97% identical, at least about 98% identical, and/or at least about 99% identical to SEQ ID NOS:4 and/or 6, and/or a functional fragment thereof; an inactivated gene encoding a FadR enzyme having at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% sequence identity to SEQ ID NO:16; and an inactivated FabF enzyme having at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% sequence identity to SEQ ID NO:14.

In some embodiments, an engineered bacteria microorganism according to the invention encompasses a polynucleotide sequence encoding a heterologous FAR; one or more heterologous polynucleotide sequences encoding i) a FabZ enzyme, ii) a FabI enzyme, and/or iii) a FabA enzyme; and one or more inactivated genes such as a fabF or fadR. gene. For example, in certain embodiments, an engineered bacterial microorganism according to the invention comprises (a) an heterologous FabZ comprising an amino acid sequence that is a least about 80%, about 85%, about 88%, about 90%, about 93%, about 95%, about 97%, about 98%, about 99%, or even about 100% identical to the amino acid sequence set forth in SEQ ID NO:8 and/or a functional fragment thereof; and/or (b) an heterologous FabI comprising an amino acid sequence that is a least about 80%, about 85%, about 88%, about 90%, about 93%, about 95%, about 97%, about 98%, about 99%, or even about 100% identical to the amino acid sequence set forth in SEQ ID NO:12 and/or a functional fragment thereof; and/or (c) an heterologous FabA comprising an amino acid sequence that is a least about 80%, about 85%, about 88%, about 90%, about 93%, about 95%, about 97%, about 98%, about 99%, or even about 100% identical with the amino acid sequence set forth in SEQ ID NO:10 and/or a functional fragment thereof; and (d) an inactivated gene selected from a gene encoding (i) a FadR enzyme having at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% sequence identity to SEQ ID NO:16; and/or (ii) a FabF enzyme having at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% sequence identity to SEQ ID NO:14; and (e) a heterologous polynucleotide sequence encoding a FAR enzyme comprising an amino acid sequence that is at least about 30% identical, at least about 40%, at least about 50% identical, at least about 60% identical, at least about 70% identical, at least about 75% identical, at least about 80% identical, at least about 85% identical, at least about 90% identical, at least 91% identical, at least 92% identical, at least about 93% identical, at least about 95% identical, at least 96% identical, at least about 97% identical, at least about 98% identical, and/or at least about 99% identical to SEQ ID NO:2.

7. ENGINEERED HOST CELLS

In some embodiments, the engineered host cell is a prokaryotic cell. Suitable prokaryotic cells include Gram-positive, Gram negative and Gram-*variable* bacterial cells. In certain embodiments, host cells include, but are not limited to, species of a genus selected from the group of *Acetobacter, Acinetobacter, Agrobacterium, Arthrobacter, Bacillus, Clostridium, Corynebacterium, Desulfovibrio, Escherichia, Erwinia, Geobacillus, Klebsiella, Lactobacillus, Mycobacterium, Pantoea, Rhodococcus, Rhotobacter, Streptomyces, Vibrio,* and *Zymomonas*. In certain embodiments, the recombinant host cell is an industrial bacterial strain.

Numerous bacterial industrial strains are known and suitable for use in the methods disclosed herein. In some embodiments, the bacterial host cell is a species of the genus *Bacillus*, e.g., *B. thuringiensis, B. anthracis, B. megaterium, B. subtilis, B. lentos, B. circulans, B. pumilus, B. lautus, B. coagulans, B. brevis, B. firmus, B. alkaophius, B. licheniformis, B. clausii, B. stearothermophilus, B. halodurans, B. subtilis, B. pumilus,* and *B. amyloliquefaciens*. In some embodiments, the bacterial host cell is a species of the genus *Erwinia*, e.g., *E. uredovora, E. carotovora, E. ananas, E. herbicola, E. punctata* and *E. terreus*. In other embodiments the bacterial host cell is a species of the genus *Pantoea*, e.g., *P. citrea* or *P. agglomerans*. In still other embodiments, the bacterial host cell is a species of the genus *Streptomyces*, e.g., *S. ambofaciens, S. achromogenes, S. avermitilis, S. coelicolor, S. aureofaciens, S. aureus, S. fungicidicus, S. griseus* or *S. lividans*. In further embodiments, the bacterial host cell is a species of the genus *Zymomonas*, e.g., *Z. mobilis* or *Z. lipolytica*. In further embodiments, the bacterial host cell is a species of the genus *Rhodococcus*, e.g. *R. opacus*.

In some embodiments, the bacterial host cell is a species of the genus *Escherichia*, e.g., *E. coli*. In various embodiments, the engineered *E. coli* bacterial strains useful in the processes described herein are derived from strain W3110, strain MG1655, strain B766 (*E. coli* W) and strain BW25113. In some further embodiments, the W3110 strain finds use in the present invention; the genome of this strain has been fully sequenced and annotated (See e.g., Hayashi et al., (2005) Mol. Syst. Biol. 2:2006.0007). For industrial applications, phage-resistant strains are particularly useful. In this sense, deletion of the fhuA gene (also known as tonA) confers resistance to phages T1, T5 and phi80 (Link et al., 1997, J. Bact. 179: 6228-8237). Another useful strain is *E. coli* W (Archer et al., 2011, BMC Genomics, 12:9.doi: 10.1186/1471-2164-12-9). Also reference is made to Elben et al. (2005) J. of Food Protection 68(2):282-291.

Other examples of useful *E. coli* strains include, but are not limited to, *E. coli* strains found in the *E. coli* Stock Center from Yale University (http://cgsc.biology.yale.edu/index.php); the Keio Collection, available from the National BioResource Project at NBRP *E. coli*, Microbial Genetics Laboratory, National Institute of Genetics 1111 Yata, Mishima, Shizuoka, 411-8540 Japan (www at shigen.nig.ac.jp/ecoli/strain/top/top.jsp); or strains deposited at the American Type Culture Collection (ATCC).

The disclosed invention further contemplates the use of other organism such as photosynthetic organisms including but not limited to algae (e.g., cyanobacteria (blue green algae) and photosynthetic bacteria. Non-limiting examples include strains of *Synechococcus*, *Synechocystis*, *Rhodobacter*, *Rhodococcus*, *Chlamydomonas*, *Chlorella*, *Prototheca*, and *Cyanobacterium*. Additional heterotrophic species which may be used as host strains that are transformed with genes encoding enzymes involved in the synthesis of fatty alcohols include yeast cells such as but not limited to *Saccharomyces* (e.g., *S. cerevisiae*), *Yarrowia* (e.g., *Y. lipolytica*), *Candida* (e.g., *C. troplicalis*) and *Schizosaccharomyces* (e.g., *S. pombe*).

8. FERMENTATION/CULTURING

Any suitable means for culturing the recombinant host cells finds use in the present invention. Indeed, any suitable fermentation protocol finds use in the production of the fatty alcohols provided herein. In some embodiments, fermentation of the recombinant host cells as described hereinabove comprises fermenting host cells comprising: 1) a heterologous polynucleotide encoding a FabZ and a heterologous polynucleotide encoding a FAR enzyme; 2) a heterologous polynucleotide encoding a FabI and a heterologous polynucleotide encoding a FAR enzyme; 3) a heterologous polynucleotide encoding a FabZ; a heterologous polynucleotide encoding a FabI; and a heterologous polynucleotide encoding a FAR enzyme; 4) a heterologous polynucleotide encoding a FabA and a heterologous polynucleotide encoding a FAR enzyme; 5) a heterologous polynucleotide encoding a FabA; a heterologous polynucleotide encoding a FabI; and a heterologous polynucleotide encoding a FAR enzyme; 6) a heterologous polynucleotide encoding a FAR enzyme and an inactivated fabF encoding a FabF polypeptide; or 7) a heterologous polynucleotide encoding a FAR enzyme and an inactivated fadR encoding a FadR polypeptide; under suitable conditions and for a time sufficient for production of fatty alcohols, as desired. Conditions for the culture and production of cells, including bacterial and yeast cells, are readily available and well-known in the art. Cell culture media in general are set forth in Atlas and Parks (eds.) *The Handbook of Microbiological Media* (1993) CRC Press, Boca Raton, Fla., which is incorporated herein by reference. Additional information for cell culture is found in available commercial literature such as the *Life Science Research Cell Culture Catalogue* (1998) from Sigma-Aldrich, Inc (St Louis, Mo.) ("Sigma-LSRCCC") and, for example, *The Plant Culture Catalogue* and supplement (1997) also from Sigma-Aldrich, Inc (St Louis, Mo.) ("Sigma-PCCS"), all of which are incorporated herein by reference. Also reference is made to the Manual of Industrial Microbiology and Biotechnology. A. Demain and J. Davies Eds. ASM Press. 1999.

In some embodiments, the recombinant cells encompassed by the invention are grown under batch or continuous fermentations conditions. Classical batch fermentation is a closed system, wherein the compositions of the medium is set at the beginning of the fermentation and is not subject to artificial alterations during the fermentation. A variation of the batch system is a fed-batch fermentation which also finds use in the present invention. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation is a system where a defined fermentation medium is added continuously to a bioreactor and an equal amount of conditioned medium (e.g., containing the desired end-products) is removed simultaneously for processing. Continuous fermentation generally maintains the cultures at a constant high density where cells are primarily in the growth phase where production of end products is enhanced. Continuous fermentation systems strive to maintain steady state growth conditions. Methods for modulating nutrients and growth factors for continuous fermentation processes as well as techniques for maximizing the rate of product formation are well known in the art of industrial microbiology.

In some embodiments, fermentations are carried out a temperature within the range of from about 10° C. to about 60° C., from about 15° C. to about 50° C., from about 20° C. to about 45° C., from about 25° C. to about 45° C., from about 30° C. to about 45° C. and from about 25° C. to about 40° C. Indeed, it is intended that any suitable fermentation temperature will be used in the present invention.

In some other embodiments, the fermentation is carried out for a period of time within the range of from about 8 hours to 240 hours, from about 8 hours to about 168 hours, from about 16 hours to about 144 hours, from about 16 hours to about 120 hours, or from about 24 hours to about 72 hours. Indeed, it is intended that any suitable fermentation time will find use in the present invention.

In some other embodiments, the fermentation will be carried out at a pH in the range of about 4 to about 8, in the range of about 4.5 to about 7.5, in the range of about 5 to about 7, or in the range of about 5.5 to about 6.5. Indeed, it is intended that any suitable pH range will find use in the present invention.

Carbon sources useful in the aqueous fermentation medium (e.g., broth) in which the recombinant microorganisms are grown are those that can be assimilated by the recombinant host strain. Such carbon sources are available in many forms and include renewable carbon sources, including but not limited to cellulosic and starch feedstock substrates obtained therefrom. Such examples include for example fermentable sugars such as monosaccharides, disaccharides, and short chain oligosaccharides (e.g., glucose, fructose, xylose, galactose, arabinose, maltose, mannose, arabinose, and sucrose, as well as numerous other sugars; it is not intended that the present invention be limited to any particular fermentable sugar). Other carbon sources include, but are not limited to saturated and unsaturated fatty acids, glycerol, lactose, succinate, acetate and mixtures thereof.

In some embodiments, the assimilable carbon source is from cellulosic and/or starch feedstock derived from but not limited to, wood, wood pulp, paper pulp, grain (e.g., corn grain), corn stover, corn fiber, rice, paper and pulp processing waste, woody or herbaceous plants and residue, fruit or vegetable pulp, distillers grain, grasses, rice hulls, wheat straw, cotton, hemp, flax, sisal, corn cobs, sugar cane bagasse, sugar beets, sorghum, barely, barely straw, switch grass, wood chips, municipal solid wastes, aquatic crops, and mixtures thereof.

In some embodiments, the cellulosic feedstock useful as an assimilable carbon source has been derived from a biomass substrate that has been pretreated. The term "biomass" is broadly used herein to encompasses any living or dead biological material that contains a polysaccharide substrate, including but not limited to cellulose, starch, other forms of long-chain carbohydrate polymers, and mixtures of such sources. Examples of biomass include, but are not limited to, wood, wood pulp, paper pulp, corn fiber, corn grain, corn cobs, sugar cane, sugar beet, crop residues such as corn husks, corn stover, grasses, wheat, wheat straw, barley, barley straw, hay, rice, rice straw, switchgrass, waste paper, paper and pulp processing waste, woody or herbaceous plants, fruit or vegetable pulp, distillers grain, grasses, rice hulls, cotton, hemp, flax, sisal, sugar cane bagasse, sorghum, soy, switchgrass, components obtained from milling of grains, trees, branches, roots, leaves, wood chips, sawdust, shrubs and bushes, vegetables, fruits, and flowers and any suitable mixtures thereof. In some embodiments, the biomass comprises, but is not limited to cultivated crops (e.g., grasses, including C4 grasses, such as switch grass, cord grass, rye grass, miscanthus, reed canary grass, or any combination thereof), sugar processing residues, for example, but not limited to, bagasse (e.g., sugar cane bagasse, beet pulp [e.g., sugar beet], or a combination thereof), agricultural residues (e.g., soybean stover, corn stover, corn fiber, rice straw, sugar cane straw, rice, rice hulls, barley straw, corn cobs, wheat straw, canola straw, oat straw, oat hulls, corn fiber, hemp, flax, sisal, cotton, or any combination thereof), fruit pulp, vegetable pulp, distillers' grains, forestry biomass (e.g., wood, wood pulp, paper pulp, recycled wood pulp fiber, sawdust, hardwood, such as aspen wood, softwood, or a combination thereof). Furthermore, in some embodiments, the biomass comprises cellulosic waste material and/or forestry waste materials, including but not limited to, paper and pulp processing waste, municipal paper waste, newsprint, cardboard and the like. In some embodiments, biomass comprises one species of fiber, while in some alternative embodiments the biomass comprises a mixture of fibers that originate from different biomasses. In some embodiments, the biomass may also comprise transgenic plants that express ligninase and/or cellulase enzymes (See e.g., US 2008/0104724 A1).

In some embodiments, the biomass substrate is "pretreated," using methods known in the art, such as chemical pretreatment (e.g., ammonia pretreatment, dilute acid pretreatment, dilute alkali pretreatment, or solvent exposure), physical pretreatment (e.g., steam explosion or irradiation), mechanical pretreatment (e.g., grinding or milling) and biological pretreatment (e.g., application of lignin-solubilizing microorganisms) and combinations thereof, to increase the susceptibility of cellulose to hydrolysis. In some embodiments, the substrate is slurried prior to pretreatment. The following references described various means of pretreatment. Steam explosion performing acid pretreatment of biomass substrates is described in U.S. Pat. No. 4,461,648. Continuous pretreatment using a slurry is described U.S. Pat. No. 7,754,457. Methods of alkali pretreatment is such as Ammonia Freeze Explosion, Ammonia Fiber Explosion or Ammonia Fiber Expansion ("AFEX") are described in U.S. Pat. Nos. 5,171,592; 5,037,663; 4,600,590; 6,106,888; 4,356,196; 5,939,544; 6,176,176; 5,037,663 and 5,171,592. Alternative methods to AFEX utilizing a dilute ammonia pretreatments are described in WO2009/045651 and US 2007/0031953. Chemical pretreatments with organic solvents are disclosed in U.S. Pat. No. 4,556,430. Other pretreatments methods are disclosed in U.S. Pat. No. 7,465,791, and Weil et al. (1997) Appl. Biochem. Biotechnol., 68(1-2): 21-40 [1997].

9. PRODUCTION OF FATTY ALCOHOLS AND SATURATION LEVELS

In various embodiments, fatty alcohols produced by the methods of the invention are further recovered or isolated. Recovery or isolation of the produced fatty alcohols refers to substantially separating the fatty alcohols from other components of the culture medium or fermentation process. Recovery or isolation may be accomplished by solvent extraction of the aqueous nutrient medium with a suitable water immiscible solvent. Extraction may occur simultaneously with fatty alcohol production and in some embodiments, extraction is continuous. Phase separation followed by solvent removal provides the fatty alcohol which may then be further purified and fractionated using methods and equipment known in the art. In some other aspects of the invention, the secreted fatty alcohols coalesce to form a water immiscible phase that can be directly separated from the aqueous nutrient medium either during the fermentation process or after its completion.

In certain embodiments of the invention, at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, of the fatty alcohols produced by the methods described herein are secreted into the culture medium by the recombinant host cells.

In certain embodiments, fatty alcohols are isolated by separating the host cells from the aqueous nutrient medium, for example by centrifugation, resuspension and extraction of the fatty alcohols from the recombinant host cells using an organic solvent or solvent mixture. Suitable protocols for recovering fatty alcohols from recombinant host cells and/or culture medium are known to the skilled artisan. In some embodiments, fatty alcohols may be recovered by first lysing the cells to release the fatty alcohols and then extracting the fatty alcohol from the lysate using conventional means. Reference is also made to Yeast Protocols Handbook, (2009) Clontech Laboratories, Inc. A Takara Bio Company, Mt. View Calif. 94043; PNAS 2003 Vol. 100, 16:9156-9161; and Doan et al., (2009) J. Plant Physiol. 166: 787-796 which discloses methods to isolate and measure fatty alcohols produced in *E. coli* using FARs from *Arabidopsis*. Indeed, it is intended that any suitable method will find use in the present invention and it is not intended that the present invention be limited to any particular method(s) for separating host cells from the nutrient medium.

In various embodiments, the compositions produced by the engineered cells and methods described herein comprise both saturated and unsaturated fatty alcohols. In certain embodiments, the unsaturated fatty alcohols are monounsaturated fatty alcohols. In some embodiments, the fatty alcohol compositions comprise both saturated and unsaturated fatty alcohols, and the amount of unsaturated fatty alcohols compared to saturated fatty alcohols in the total fatty alcohol composition is less than about 40%, less than about 35%, less than about 30%, less than about 20%, less than about 15%, less than about 10%, less than about 5%, or less than about 1% of the fatty alcohols present in the composition.

In some embodiments, the fatty alcohol compositions comprise both saturated and unsaturated fatty alcohols. In some embodiments, the percentage of saturated fatty alcohols in the fatty alcohol compositions produced by the engineered bacterial cells encompassed by the invention is greater than about 50%, greater than about 55%, greater than about 60%, greater than about 65%, greater than about 70%, greater than about 75%, greater than about 80%, greater than about 85%, greater than about 90%, greater than about 95%, or greater than about 97%.

In some embodiments, the fatty alcohol compositions produced by the engineered cells and the methods described herein comprise one or more alcohols selected from 1-decanol (C10:0), 1-dodecanol (C12:0), 1-tetradecanol (C14:0), 1-hexadecanol (C16:0), and 1-octadecanol (C18:0).

In some typical embodiments, C10 to C18 fatty alcohols comprise at least about 95%, at least about 96%, at least about 97%, at least about 98%, or at least about 99% by weight of the total fatty alcohols produced by the recombinant host cells. In some embodiments, C12 to C16 fatty alcohols comprise at least about 85%, at least about 90%, at least about 92%, at least about 93%, at least about 94%, at least about 95%, at least about 96%, at least about 97%, or at least about 98% by weight of the total fatty alcohols produced by the recombinant host cells. In certain embodiments, C14 to C16 fatty alcohols comprise at least about 80%, at least about 85%, at least about 90%, at least about 92%, at least about 95%, at least about 97%, or at least about 99% by weight of the total produced fatty alcohols. It is understood that a reference to a "Cx fatty alcohol" (e.g., C12) includes both saturated and unsaturated fatty alcohols having "x" carbon atoms.

In some typical embodiments, C10:0 to C18:0 fatty alcohols comprise at least about 95%, at least about 96%, at least about 97%, at least about 98%, or at least about 99% by weight of the total produced fatty alcohols. In some embodiments, C12:0 to C16:0 fatty alcohols comprise at least about 85%, at least about 90%, at least about 92%, at least about 93%, at least about 94%, at least about 95%, or at least about 98% by weight of the total produced fatty alcohols. In certain embodiments, C14:0 to C16:0 fatty alcohols comprise at least about 80%, at least about 85%, at least about 90%, at least about 92%, at least about 95%, at least about 97%, or at least about 99% by weight of the total produced fatty alcohols. The proportions of saturated and unsaturated fatty alcohols produced by the strains may be calculated after quantifying all the fatty alcohol species using any suitable method known in the art (e.g., GC-FID as described in US 2011/0000125SA1). The saturated fraction represents the sum of all C12:0-OH; C14:0-OH; C16:0-OH and C18:0-OH. While the unsaturated fraction is composed of the sum of C12:1-OH: C14:1-OH: C16:1-OH and C18:1-OH.

In some embodiments, the fatty alcohol compositions produced by the engineered cells comprise a % of saturated fatty alcohols that is greater than about 10%, greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75%, greater than about 80%, greater than about 85%, greater than about 90%, greater than about 95%, or greater than about 97%. In some additional embodiments, the fatty alcohol compositions further comprise at least about 85%, at least about 88%, at least about 90%, at least about 91%, at least about 92%, at least about 93%, at least about 94%, at least about 95%, at least about 96%, at least about 97%, or at least about 98% C12 to C16 fatty alcohols.

In certain embodiments, the present invention provides a recombinant bacterial cell comprising: a) a heterologous fabZ polynucleotide encoding a FabZ enzyme comprising a sequence having at least about 80%, about 85%, about 88%, about 90%, about 93%, about 95%, about 97%, about 98%, about 99%, or even about 100% sequence identity to SEQ ID NO:8 or SEQ ID NO: 26 and b) a heterologous polynucleotide encoding a FAR polypeptide having at least about 80%, about 85%, about 90%, about 93%, about 95%, about 97%, about 98%, about 99%, or even about 100% sequence identity to SEQ ID NO:2, SEQ ID NO: 4; SEQ ID NO: 6, SEQ ID NO: 18 or SEQ ID NO: 28; and wherein the recombinant bacterial host cell produces a fatty alcohol composition that comprises at least about 70%, about 75%, about 80%, about 82%, about 84%, about 86%, about 88%, or about 90% C14:0 to C16:0 fatty alcohols wherein the % saturation of the fatty alcohol composition is greater than about 50%, about 55%, about 60%, about 70%, about 75%, about 80%, about 85%, or about 90%. In some embodiments, the recombinant bacterial cell produces a fatty alcohol composition comprising at least about 70%, about 75%, about 80%, about 82%, about 84%, about 86%, about 88%, or about 90% C12:0 to C16:0 fatty alcohols wherein the % saturation of the fatty alcohol composition is greater than about 50%, about 55%, about 60%, about 70%, about 75%, about 80%, about 85%, about 90% and about 95%.

In certain aspects of this embodiment, the amount of saturated fatty alcohols produced by the engineered bacterial cell is at least about 1%, at least about 2%, at least about 5%, at least about 8%, at least about 10%, at least about 12%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% greater than the amount of saturated fatty alcohol produced by a corresponding engineered bacterial cell grown under essentially the same culture conditions. In some embodiments, the engineered bacterial cell is one that produces a heterologous FAR and a heterologous FabZ and/or FabI wherein the corresponding bacterial cell to which the engineered bacterial cell of the invention is compared to does not included a heterologous FabZ and/or FabI and the engineered bacterial cell of the invention produces a fatty alcohol composition that is at least 5%, at least 10%, at least 15%, at least 20% or greater than the corresponding bacterial cell to which is it compared to. In some embodiments, the engineered bacterial cell is one that produces a heterologous FAR; a heterologous FabZ and/or a heterologous FabI; and further expresses or overexpresses a heterologous TE and a FadD wherein the corresponding bacterial cell to which the engineered bacterial cell it is compared to does not included a heterologous FabZ and/or heterologous FabI and the engineered bacterial cell of the invention produces a fatty alcohol composition that is at least 5%, at least 10%, at least 15%, at least 20% or greater than the corresponding bacterial cell to which is it compared to. In some embodiments, the engineered bacterial cell is one that produces a heterologous FAR and a heterologous FabA and/or a heterologous FabI wherein the corresponding bacterial cell to which the engineered bacterial cell of the invention is compared to does not included a heterologous FabA and/or FabI and the engineered bacterial cell of the invention produces a fatty alcohol composition that is at least 5%, at least 10%, at least 15%, at least 20% or greater than the corresponding bacterial cell to which is it compared to. In some embodiments, the engineered bacterial cell is one that produces a heterologous FAR and further has an inactivated FadR gene wherein the corresponding bacterial cell to which the engineered bacterial cell is compared to does not included an inactivated FadR gene and the engineered bacterial cell of the invention produces a fatty alcohol composition that is at least 5%, at least 10%, at least 15% at least 20% or greater than the corresponding bacterial cell to which is it compared to. In some embodiments, the engineered bacterial cell is one that produces a heterologous FAR and further has an inactivated FabF gene wherein the corresponding bacterial cell to which the engineered bacterial cell is compared to does not included an inactivated FabF gene and the engineered bacterial cell of the invention produces a fatty alcohol composition that is at least 5%, at least 10%, at least 15% at least 20% or greater than the corresponding bacterial cell to which is it compared to. In some embodiments, the culturing is carried out a temperature within the range of from about 25° C. to about 45° C.

In certain embodiments, the present invention provides a recombinant bacterial cell comprising: a) a heterologous fabI polynucleotide encoding a FabI enzyme comprising a sequence having at least about 80%, about 85%, about 88%, about 90%, about 93%, about 95%, about 97%, about 98%, about 99%, or even about 100% sequence identity to SEQ ID NO:12 and b) a heterologous polynucleotide encoding a FAR polypeptide having at least about 80%, about 85%, about 90%, about 93%, about 95%, about 97%, about 98%, about 99%, or even about 100% sequence identity to SEQ ID NO:2, SEQ ID NO: 4, SEQ ID NO: 6, SEQ ID NO: 18 or SEQ ID NO: 28. In some embodiments, the recombinant bacterial cell produces a fatty alcohol composition comprising at least about 70%, about 75%, about 80%, about 82%, about 84%, about 86%, about 88%, or about 90% C14:0 to C16:0 fatty alcohols wherein the % saturation of the fatty alcohol composition is greater than about 50%, about 55%, about 60%, about 70%, about 75%, about 80%, about 85%, about 90% and about 95%. In some embodiments, the recombinant bacterial cell produces a fatty alcohol composition comprising at least about 70%, about 75%, about 80%, about 82%, about 84%, about 86%, about 88%, or about 90% C12:0 to C16:0 fatty alcohols wherein the % saturation of the fatty alcohol composition is greater than about 50%, about 55%, about 60%, about 70%, about 75%, about 80%, about 85%, 90% and 95%. In certain aspects of this embodiment, the amount of saturated fatty alcohols produced by the engineered bacterial cell is at least about 1%, at least about 2%, at least about 5%, at least about 8%, at least about 10%, at least about 12%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% greater than the amount of saturated fatty alcohol produced by a corresponding engineered bacterial cell grown under essentially the same culture conditions. In some embodiments, the culturing is carried out a temperature within the range of from about 25° C. to about 45° C.

In certain embodiments, the present invention provides a recombinant bacterial cell comprising: a) a heterologous fabZ polynucleotide encoding a FabZ enzyme comprising a sequence having at least about 80%, about 85%, about 88%, about 90%, about 93%, about 95%, about 97%, about 98%, about 99%, or even about 100% sequence identity to SEQ ID NO:8 or SEQ ID NO: 26; b) a heterologous fabI1 polynucleotide encoding a FabI1 enzyme comprising a sequence having at least about 80%, about 85%, about 88%, about 90%, about 93%, about 95%, about 97%, about 98%, about 99%, or even about 100% sequence identity to SEQ ID NO:12; and/or c) a heterologous polynucleotide encoding a FAR polypeptide having at least about 80%, about 85%, about 90%, about 93%, about 95%, about 97%, about 98%, about 99%, or even about 100% sequence identity to SEQ ID NO:2, SEQ ID NO: 4, SEQ ID NO: 6, SEQ ID NO: 18 or SEQ ID NO: 28. In some embodiments, the recombinant bacterial cell produces a fatty alcohol composition comprising at least about 70%, about 75%, about 80%, about 82%, about 84%, about 86%, about 88%, or about 90% C14:0 to C16:0 fatty alcohols. In some embodiments, the recombinant bacterial cell produces a fatty alcohol composition comprising at least about 70%, about 75%, about 80%, about 82%, about 84%, about 86%, about 88%, or about 90% C12:0 to C16:0 fatty alcohols wherein the % saturation of the fatty alcohol composition is greater than about 50%, about 55%, about 60%, about 70%, about 75%, about 80%, about 85%, about 90% and about 95%. In some embodiments, the % saturation of the fatty alcohol composition is greater than about 50%, about 55%, about 60%, about 70%, about 75%, about 80%, about 85%, 90% and 95%. In certain aspects of this embodiment, the amount of saturated fatty alcohols produced by the engineered bacterial cell is at least about 1%, at least about 2%, at least about 5%, at least about 8%, at least about 10%, at least about 12%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% greater than the amount of saturated fatty alcohol produced by a corresponding engineered bacterial cell grown under essentially the same culture conditions. In some embodiments, the culturing is carried out a temperature within the range of from about 25° C. to about 45° C.

In certain embodiments, the present invention provides a recombinant bacterial cell comprising: a) a heterologous fabA polynucleotide encoding a FabA enzyme comprising a sequence having at least about 80% about 85%, about 88%, about 90%, about 93%, about 95%, about 97%, about 98%, about 99%, or even about 100% sequence identity to SEQ ID NO:10; and b) a polynucleotide encoding a FAR polypeptide having at least about 80%, about 85%, about 90%, about 93%, about 95%, about 97%, about 98%, about 99%, or even about 100% sequence identity to SEQ ID NO:2; SEQ ID NO: 4, SEQ ID NO: 6, SEQ ID NO: 18 or SEQ ID NO: 28, wherein the recombinant bacterial cell produces a fatty alcohol composition that comprises at least about 70%, about 75%, about 80%, about 82%, about 84%, about 86%, about 88%, or about 90% C14:0 to C16:0 fatty alcohols, wherein the % saturation of the fatty alcohol composition is greater than about 50%, about 55%, about 60%, about 70%, about 75%, about 80%, about 85%, or about 90% or wherein the recombinant bacterial cell produces a fatty alcohol composition comprising at least about 70%, about 75%, about 80%, about 82%, about 84%, about 86%, about 88%, or about 90% C12:0 to C16:0 fatty alcohols wherein the % saturation of the fatty alcohol composition is greater than about 50%, about 55%, about 60%, about 70%, about 75%, about 80%, about 85%, 90% and 95%. In certain aspects of this embodiment, the amount of saturated fatty alcohols produced by the engineered bacterial cell is at least about 1%, at least about 2%, at least about 5%, at least about 8%, at least about 10%, at least about 12%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% greater than the amount of saturated fatty alcohol produced by a corresponding engineered bacterial cell grown under essentially the same culture conditions. In some embodiments, the culturing is carried out a temperature within the range of from about 25° C. to about 45° C.

In certain embodiments, the amount of fatty alcohols produced by the methods described herein comprise saturated and/or unsaturated C8 to C18 alcohols produced by a recombinant host cell comprising a heterologous gene encoding a FAR as described herein in a range of about 10 mg/L to about 50 g/L of aqueous nutrient medium, such as in a range of about 10 mg/L to about 5 g/L, or in a range of about 10 mg/L to about 2 g/L of medium, using routine modification of culturing conditions. In some embodiments, the amount of fatty alcohols produced by the methods described herein is at least about 0.5 g/L, at least about 1 g/L, at least about 1.5 g/L, at least about 2.0 g/L, at least about 2.5 g/L, at least about 3 g/L, at least about 3.5 g/L, at least about 4 g/L, at least about 4.5 g/L, at least about 5 g/L, or at least about 10 g/L of medium. In various embodiments, the amount of fatty alcohols produced by the methods described herein is at least about 20 g/L, at least about 30 g/L, at least about 40 g/L, or at least about 50 g/L of medium. In some embodiments, a recombinant bacteria (e.g., *E. coli*) encompassed by the invention produces C12 to C16 fatty alcohols in an amount of at least about 1.0 g/L, at least about 5.0 g/L, at least about 10 g/L, at least about 15 g/L, at least about 20 g/L, at least about 25 g/L, or at least about 30 g/L of medium. In some embodiments, a recombinant bacteria (e.g., *E. coli*) encompassed by the invention produces C12 to C14 fatty alcohols in an amount of at least about 1.0 g/L, at least about 5.0 g/L, at least about 10 g/L, at least about 15 g/L, at least about 20 g/L, at least about 25 g/L, or at least about 30 g/L of medium. One method to extract and quantify fatty alcohols is provided in US Patent Application 2011/0000125. However, it is not intended that the present invention be limited to any particular method(s) for extracting and/or quantifying the fatty alcohols produced using the present invention, as any suitable methods find use.

In some embodiments, the amount of fatty alcohols produced by the methods described herein is in the range of about 100 mg/g to about 5 g/g of dry cell weight. In other embodiments, the amount of fatty alcohols produced by the methods described herein is in the range of about 1 g/g to about 4 g/g of dry cell weight, such as in the range of about 2 g/g to about 3 g/g of dry cell weight.

In certain embodiments, the amount of fatty alcohols produced by the methods described herein is in the range of about 10% to about 20% of dry cell weight, about 20% to about 30% of dry cell weight, about 30% to about 40% of dry cell weight, about 40% to about 50% of dry cell weight, about 50% to about 60% of dry cell weight, about 60% to about 70% of dry cell weight, or about 70% to about 80% of dry cell weight.

In some embodiments, the fatty alcohol compositions produced by the engineered cells and methods described herein may also comprise fatty acid-derived compounds. Fatty acid-derivative compounds include compounds such as but not limited to esters (e.g. acetyl, methyl or ethyl esters and waxes) and fatty acids.

10. COMPOSITIONS

In yet another aspect, the present invention relates to the use of the engineered organisms as described herein for the production of various compositions, including but not limited to, fuel compositions (e.g., biodiesels and petrodiesels), cleaning compositions including detergent compositions (e.g., laundry detergents in liquid gel, spray, and powder form, hard surface cleaners, dishwashing detergents, and the like); industrial compositions (e.g., lubricants, solvents, and industrial cleaners); and personal care compositions (e.g., soaps, cosmetics, shampoos, gels, etc.).

Detergent Compositions

In some embodiments, the fatty alcohol compositions described herein, and compounds derived therefrom, can be used as components of detergent compositions. Detergent compositions comprising fatty alcohols and fatty alcohol derivatives produced by the methods of the present invention include compositions used in cleaning applications, including, but not limited to, laundry detergents, handwashing agents, dishwashing detergents, rinse-aid detergents, household detergents, and household cleaners, in liquid, gel, granular, powder, or tablet form. In some embodiments, the fatty alcohols produced by the methods described above are used directly in detergent compositions. In some embodiments, the fatty alcohols and fatty alcohol derivatives are reacted with a sulfonic acid group to produce sulfate derivatives that can be used as components of detergent compositions. Detergent compositions that can be generated using the fatty alcohols and fatty alcohol derivatives produced by the methods of the present invention include, but are not limited to, hair shampoos, rinses, and conditioners for humans and other animals, carpet shampoos, hard surface cleaners, light-duty household cleaners, light-duty household detergents, heavy-duty household cleaners, and heavy-duty household detergents. Detergent compositions generally include, in addition to fatty alcohols and derivative thereof, one or more builders (e.g., sodium carbonate, complexation agents, soap, and zeolites), enzymes (e.g., proteases, lipases, cellulases, and/or amylases); carboxymethyl cellulose, optical brighteners, fabric softeners, colourants and perfumes (e.g., cyclohexyl salicylate). Indeed, it is not intended that the present invention be limited to any particular detergent, detergent formulation, nor detergent use.

In some embodiments, sulfate derivatives (e.g., C12-15) derived from fatty alcohols are used in products such as hair shampoos, carpet shampoos, light-duty household cleaners, and light-duty household detergents. In some embodiments, sulfate derivatives (e.g., C16-C18) derived from fatty alcohols are used in products such as hair shampoos and conditioners. In some embodiments, sulfate derivatives (e.g., C16-18) derived from fatty alcohols are used in products such as heavy-duty household cleaners and heavy-duty household detergents. Indeed, it is not intended that the present invention be limited to any particular detergent, detergent formulation, nor detergent use.

Personal Care Compositions

In some embodiments, fatty alcohol compositions as described herein, and compounds derived therefrom, are used as components in personal care compositions. In some embodiments, the fatty alcohols produced by the methods described above are used directly in personal care compositions. Personal care compositions containing fatty alcohols or fatty alcohol derivatives produced by the methods of the present invention include compositions used for application to the body (e.g., for application to the skin, hair, nails, or oral cavity) for the purposes of grooming, cleaning, beautifying, or caring for the body, including but not limited to lotions, balms, creams, gels, serums, cleansers, toners, masks, sunscreens, soaps, shampoos, conditioners, body washes, styling aids, and cosmetic compositions (e.g., makeup in liquid, cream, solid, anhydrous, or pencil form). In some embodiments, the fatty alcohols or fatty alcohol derivatives can be reacted with a sulfonic acid group to produce sulfate derivatives that can be used as components of said compositions. In some embodiments, sulfate derivatives (e.g., C12-14) derived from the fatty alcohol compositions produced by the methods described herein are used in products such as toothpastes. Indeed, it is not intended that the present invention be limited to any particular formulation, nor use.

In some embodiments, fatty alcohol compositions (e.g., C12) produced by the methods described herein are used in products such as lubricating oils, pharmaceuticals, and as an emollient in cosmetics. In some embodiments, fatty alcohol compositions (e.g., C14) produced by the methods described herein are used in products such as cosmetics (e.g., cold creams) for its emollient properties. In some embodiments, fatty alcohol compositions (e.g., C16) produced by the methods described herein are used in products such as cosmetics (e.g., skin creams and lotions) as an emollient, emulsifier, or thickening agent. In some embodiments, fatty alcohol compositions (e.g., C18) produced by the methods described herein are used in products such as lubricants, resins, perfumes, and cosmetics, e.g., as an emollient, emulsifier, or thickening agent. Indeed, it is not intended that the present invention be limited to any particular formulation, nor use.

Other Compositions:

In some embodiments, fatty alcohol compositions (e.g., C12) produced by the methods described herein are used in products such as lubricating oils, pharmaceuticals, and as an emollient in cosmetics. In some embodiments, fatty alcohol compositions (e.g., C14) produced by the methods described herein are used in products such as cosmetics (e.g., cold creams) for its emollient properties. In some embodiments, fatty alcohol compositions (e.g., C16) produced by the methods described herein are used in products such as cosmetics (e.g., skin creams and lotions) as an emollient, emulsifier, or thickening agent. In some embodiments, fatty alcohol compositions (e.g., C18) produced by the methods described herein are used in products such as lubricants, resins, perfumes, and cosmetics, e.g., as an emollient, emulsifier, or thickening agent. In some embodiments, sulfate derivatives (e.g., C12-14) derived from the fatty alcohol compositions produced by the methods described herein are used in products such as toothpastes.

In some instances, fatty alcohols (especially cetyl alcohol, stearyl alcohol and myristyl alcohol) may be used as food additives (e.g., adjuvants and production aids).

Alkane and/or Alkene Compositions

In some embodiments, fatty alcohols produced according to the methods described herein can be reduced to yield alkanes and/or alkenes having the same carbon chain length as the fatty alcohol starting materials. Without being bound by any particular theory, the hydroxyl group of an alcohol is a poor leaving group, and therefore, in principle a chemical moiety that binds to the oxygen atom of the hydroxyl group to make it a better leaving group can be used to reduce the fatty alcohols described herein.

Any suitable method known in the art can be used to reduce the fatty alcohols. In some embodiments, reduction of fatty alcohols is carried out chemically, for example, by a Barton deoxygenation (or Barton-McCombie deoxygenation), a two-step reaction in which the alcohol is first converted to a methyl xanthate or thioimidazoyl carbamate, and the xanthate or thioimidazoyl carbamate is reduced with a tin hydride or trialkylsilane reagent under radical conditions to produce the alkane and/or alkene. See Li et al., 2007, *Modern Organic Synthesis in the Laboratory*, p. 81-83. In another embodiment, alkanes are produced by hydrogenation of fatty alcohols.

The alkanes can be isolated from the reaction mixture (which may contain unreduced fatty alcohols) to yield a composition comprising substantially all alkanes Alternatively, the alkanes and un-reduced fatty alcohols can be isolated from the reaction mixture to yield a composition comprising alkanes and fatty alcohols. In some embodiments, the fatty alcohol compositions comprise at least about 10%, at least about 20%, at least about 30%, at least about 40%, at least about 50%, at least about 60%, at least about 70%, at least about 80%, at least about 85%, at least about 90%, at least about 92%, at least about 95%, at least about 96%, at least about 97%, at least about 98%, or at least about 99% alkanes by weight of the composition after reduction. In some embodiments, the alkane is octane, decane, dodecane, tetradecane, hexadecane, octadecane, icosane, docosane, tetracosane, or mixtures thereof.

Ester Compositions:

In other embodiments, fatty alcohols are reacted with a carboxylic acid to form acid esters. Esterification reactions of fatty alcohols are well-known in the art. In certain embodiments, the transesterification reaction is carried out in the presence of a strong catalyst, e.g., a strong alkaline such as sodium hydroxide. In other embodiments, the esterification reaction is carried out enzymatically, using an enzyme that catalyzes the conversion of fatty alcohols to acid esters, such as lipoprotein lipase. See, e.g., Tsujita et al., 1999, "Fatty Acid Alcohol Ester-Synthesizing Activity of Lipoprotein Lipase" *J. Biochem.* 126:1074-1079.

The following examples are offered to illustrate, but not to limit, the claimed invention.

EXAMPLES

The present invention is described in further detail in the following Examples, which are not in any way intended to limit the scope of the invention as claimed. In the experimental disclosure below, the following abbreviations apply: ppm (parts per million); M (molar); mM (millimolar), uM and μM (micromolar); nM (nanomolar); mol (moles); gm and g (gram); mg (milligrams); ug and μg (micrograms); L and 1 (liter); ml and mL (milliliter); cm (centimeters); mm (millimeters); um and µm (micrometers); sec. (seconds); min(s) (minute(s)); h(s) (hour(s)); U (units); MW (molecular weight); rpm (rotations per minute); ° C. (degrees Centigrade); wt % (weight percent); w.r.t. (with regard to); DNA (deoxyribonucleic acid); RNA (ribonucleic acid); gDNA (genomic DNA); cDNA (complementary DNA); Sigma (Sigma Aldrich, St. Louis, Mo.); Qiagen (Qiagen, Inc., Valencia, Calif.); Invitrogen (Invitrogen, Corp., Carlsbad, Calif.); and Promega (Promega, Corp., Madison, Wis.).

Example 1

Construction of Plasmid pLS8379

To overproduce the FAR enzyme having SEQ ID NO:2 in *E. coli*, a low copy vector carrying the strong Trc promoter was constructed. A DNA fragment containing the lacI$^q$ gene, the Trc promoter, and the multiple cloning sites present in pTrcHis2-B (Invitrogen, Carlsbad, Calif.) was PCR amplified using the following primers:

```
1920TrcM-F:
                                         (SEQ ID NO: 30)
5' GACCTTAAAACCCTAAAGGCTTAAGGGCATCCGCTTACAGACA
and 1920TrcM-R:
                                         (SEQ ID NO: 31)
5'GGAGAAAATACCGCATCAGGCGCCTCAGGAGAGCGTTCACCGAC.
```

The PCR reaction was carried out using the enzyme Phusion (New England BioLabs, Ipswich, Mass.) with an initial denaturation step at 98° C. for 30 sec, followed by 25 cycles of the steps: 98° C. for 10 sec; 65° C. for 15 sec and 72° C. for 15 sec. This was followed by a final elongation step at 72° C. for 5 min.

The primers used for this PCR reaction carry regions of homology to plasmid pCL1920. Because of this, the PCR product described above can be used as a megaprimer to amplify a defined region of pCL1920 (Lerner and Inouye (1990) NAR 18: 4631) which contains the pSC101 origin of replication and confers resistance to Spectinomycin (GenBank: AB236930). This PCR reaction was carried out using the Pfu Ultra enzyme (Agilent Technologies, Santa Clara, Calif.) with an initial denaturation step at 95° C. for 2 min, followed by 16 cycles of the steps: 95° C. for 30 sec; 55° C. for 30 sec and 68° C. for 7 min. This was followed by a final elongation step at 68° C. for 7 min.

The outcome of the second PCR reaction was sequence-verified and the resulting plasmid was named pLS8379 (SEQ ID NO: 29).

Example 2

Construction of Plasmids pCL3079 and Plasmid pCL5019

Two synthetic genes (SEQ ID NO: 3 and SEQ ID NO: 5) encoding the FAR polypeptides having SEQ ID NO: 4 (V1) and SEQ ID NO: 6 (V2) were ligated as NcoI-SalI fragments to pLS8379 digested with the same restriction enzymes. Ligation reactions were incubated overnight at 16° C. and then transformed into *E. coli* DH10B-T1 electrocompetent cells (Invitrogen, Carlsbad, Calif.) following the manufacturer's protocols. Cells were plated on LB agar plates containing 100 ug/ml of Spectinomycin. Plates were incubated overnight at 37° C. Obtained clones were sequence verified.

Example 3

Construction of the Plasmids pCL3079-fabA; pCL3079-RBSfabA; pCL5019-fabA and pCL3079-RBSfabA The *E. coli* fabA gene (SEQ ID NO: 9) (encoding FabA comprising SEQ ID NO:10) including its natural ribosome binding site (RBS) sequence was PCR amplified from genomic DNA isolated from *E. coli* strain W3110, using primers:

```
ampFabA-Fwd:
                                         (SEQ ID NO: 32)
5'-TACAGAGAACATGGTAGATAAAC-3'
and ampFabA-Rev:
                                         (SEQ ID NO: 33)
5'-TAGAAGGCAGACGTATCCTG-3'.
```

Primer ampFabA-Rev was designed to replace the normal TGA stop codon of fabA with the TAA stop codon.

The PCR reaction was carried out using the enzyme Phusion (New England BioLabs, Ipswich, Mass.) with an initial denaturation step at 98° C. for 30 sec, followed by 25 cycles of the steps: 98° C. for 10 sec; 58° C. for 20 sec and 72° C. for 15 sec. This was followed by a final elongation step at 72° C. for 5 min.

The PCR product obtained was cloned using the TOPO kit from Invitrogen (Carlsbad, Calif.) following manufacturer instructions. Topo cloning reaction was transformed into commercial electrocompetent TOP10 *E. coli* cells and cells were plated on LB agar plates containing 100 micrograms/ml of Carbenicillin. Plates were incubated overnight at 37° C. The sequence of the cloned fabA gene was verified.

A variant of the fabA gene, where its native ribosome binding site (RBS)/spacing was replaced with a strong RBS/spacing with the sequence: AGGAAACAGCTATG (SEQ ID NO: 34), was obtained by PCR using primer RBS-fabA with the new RBS sequence incorporated on it:

```
RBS-fabA:
                                         (SEQ ID NO: 35)
5'-AGGAAACAGCTATGGTAGATAAACGCGAATC-3'.
```

This PCR reaction was carried out using the enzyme Phusion (New England BioLabs, Ipswich, Mass.) with an initial denaturation step at 98° C. for 30 sec, followed by 25 cycles of the steps: 98° C. for 10 sec; 58° C. for 20 sec and 72° C. for 15 sec. This was followed by a final elongation step at 72° C. for 5 min.

pCL3079-fabA and pCL5019-FabA were constructed as follow:

pCL3079 and pCL5019 were linearized by digestion with the PmeI restriction enzyme. To facilitate cloning, the ends of the DNA fragments were dephosphorylated using Antartic phosphatase (New England BioLabs, Ipswich, Mass.) following manufacturer recommendations.

The two different versions of the fabA genes were PCR amplified from the clones described above using primers containing 20 bp homology to the vector on forward and reverse primer described below:

Pme-inF-RBS-FabA:
(SEQ ID NO: 36)
TCATCATCATCATTGAGTTTAGGAAACAGCTATGGTAGATAAAC;

Pme-inF-FabA_Fwd:
(SEQ ID NO: 37)
TCATCATCATCATTGAGTTTTACAGAGAACATGGTAGATAAAC;
and Pme-inF-FabA-Rev:
(SEQ ID NO: 38)
AGCCAAGCTGGAGACCGTTTTTAGAAGGCAGACGTATCCTG.

This PCR reaction was carried out using the enzyme Phusion (New England BioLabs, Ipswich, Mass.) with an initial denaturation step at 98° C. for 30 sec, followed by 25 cycles of the steps: 98° C. for 10 sec; 58° C. for 20 sec and 72° C. for 15 sec. This was followed by a final elongation step at 72° C. for 5 min.

Obtained PCR products were gel purified using Nucleo-Spin Extract II Kit (Clontech Laboratories Inc. Mountain View, Calif.) and cloned into linearized pCL3079 or pCL5019 using the In-Fusion Kit (Clontech Laboratories Inc. Mountain View, Calif.) according to manufacturer's protocol. In-Fusion reaction mixture was transformed into DH10B-T1 cells plated on LB agar plates containing 100 micrograms/ml of Spectinomycin. Plates were incubated overnight at 37° C. Resulting plasmids were sequence-verified and named pCL3079-fabA, pCL3079-RBS-fabA, pCL5019-fabA or pCL5019-RBS-fabA respectively.

Example 4

Construction of the pCL3079-fabZ and pCL5019 fabZ

The *E. coli* fabZ gene (SEQ ID NO: 7) including its natural RBS/spacing sequence was PCR amplified from genomic DNA isolated from *E. coli* strain W3110, using primers:

ampFabZ-Fwd:
(SEQ ID NO: 39)
5'-ACAGGAAGAGTATCATGACTACTAAC-3'
and ampFabZ-Rev:
(SEQ ID NO: 40)
5'-TTAGGCCTCCCGGCTACGAGCAC-3'.

The PCR reaction was carried out as described above in Example 3. These primers were also used to replace the original TTG start and TGA stop codons present in fabZ, with ATG and TAA codons respectively. The obtained PCR product was cloned using the TOPO cloning kit as described in Example 3. The sequence of fabZ gene was verified.

The fabZ gene was cloned downstream of FAR in plasmid pCL3079 and pCL5019 using the same approach described above for fabA. The sequence of the primers used to amplify fabZ for the In-Fusion reactions were:

Pme-inF-FabZ-Fwd:
(SEQ ID NO: 41)
ATCATCATCATCATTGAGTTTAGGAAGAGTATCATGACTAC
and

Pme-inF-FabZ-Rev:
(SEQ ID NO: 42)
CAGCCAAGCTGGAGACCGTTTTTAGGCCTCCCGGCTACGAG.

Example 5

Construction of pCL5019-fabI1-fabZ pCL5019 comprising the polynucleotide encoding the FAR variant having the amino acid sequence of SEQ ID NO:6 (FAR-V2) was digested with restriction enzymes SalI-PmeI (New England BioLabs, Ipswich, Mass.) following the manufacturer recommendations. A synthetic linker containing a multi-cloning site (MCS) was ligated into this vector to facilitate further cloning. pCLlinker_Fwd: TCGA-CATAGATCTAGAACTTACTCGGAAGCTTCTTAAT-TAAGAGG  ATCCATTGACGTCTATGAATTCGTTT (SEQ ID NO:43) and pCLlinker_Rev: AAACGAAT-TCATAGACGTCAATGGATCCTCTTAAT-TAAGAAGCTT CCGAGTAAGTTCTAGATCTATG (SEQ ID NO:44). After ligation, the obtained plasmid pCL5019 linker was sequence verified.

The protein sequence of FabI-1 from *Rhodobacter sphaeroides* SB103 (GenBank: ADE86080. SEQ ID NO: 12) was utilized to design an *E. coli* codon-optimized gene (SEQ ID NO: 11). This gene was synthesized and cloned in pUC57 by GenScript (Piscataway, N.J.). The gene was PCR amplified from plasmid pUC57-FabI-1, using Phusion polymerase, with primers containing a SalI site and RBS/spacing in front of fabI-1 and a HindIII site on the 3' end primer.

Primers Sequences:

5019-FabI-1Fwd:
(SEQ ID NO: 45)
5'-ACTAAGTCGACATAAGGAGATATACATATGACC

5019-FabI-1Rev:
(SEQ ID NO: 46)
5'-AGGTCAAGCTTATTAGTCTTTACG

The PCR reaction was carried out using the enzyme Phusion (New England BioLabs, Ipswich, Mass.) with an initial denaturation step at 98° C. for 10 sec, followed by 25 cycles of the steps: 98° C. for 20 sec; 56° C. for 20 sec and 72° C. for 30 sec. This was followed by a final elongation step at 72° C. for 5 min.

After the PCR reaction, the PCR product was purified through a PCR purification column and eluted with water. This DNA was digested with the restriction enzymes SalI and HindIII (New England BioLabs, Ipswich, Mass.) following manufacturer recommendations.

The fabZ gene was PCR amplified from TOPO-fabZ plasmid described in Example 5 with primers containing HindIII site on 5'end primer and AatII site on 3'end primer.

FabZ_Fwd:
(SEQ ID NO: 47)
AGTAAGCTTGAGTTTAGGAAGAGTATCATG
and

FabZ_Rev:
(SEQ ID NO: 48)
AAGCTGACGTCTTAGGCCTCCCGGCTACG

The resulting PCR product was purified through a PCR purification column; eluted with water. The DNA was digested with the restriction enzymes HindIII and AatII (New England BioLabs, Ipswich, Mass.) following manufacturer recommendations.

The final plasmid pCL5019-FabI-1-fabZ was obtained by a three way ligation between FabI-1/SalI-HindII, FabZ/

HindIII-AatII fragments and pCL5019 linker vector digested with SalI-AatII. The ligation reaction was performed overnight at 16° C.

The product of the ligation reaction was transformed into *E. coli* DH10B-T1 electrocompetent cells and plated on LB agar plates containing 100 micrograms/ml of Spectinomycin. Plates were incubated overnight at 37° C. The obtained construct was sequence verified.

Example 6

Construction of pCL5019-FabI1-FabA and pCL5019-FabI1-RBSFabA

A plasmid which overexpresses FAR, the FabI-1 from *R. sphaeroides* SB103 and the *E. coli* fabA or RBS-fabA was constructed as described above in Example 5, except that the following primers were used to PCR-amplify fabA:

```
FabA_Fwd:
                                    (SEQ ID NO: 49)
AGTAAGCTTGAGTTTTACAGAGAACATGG
and FabA_Rev:
                                    (SEQ ID NO: 50)
AAGCTGACGTCTTAGAAGGCAGACGTATCC
or for RBS-fabA:
rbsFabA_Fwd:
                                    (SEQ ID NO: 51)
AGTAAGCTTGAGTTTAGGAAACAGCTATG
and FabA_Rev:
                                    (SEQ ID NO: 52)
AAGCTGACGTCTTAGAAGGCAGACGTATCC
```

Example 7

Construction of FadR Deletion (ΔFadR) Strains

Strain JW1176-1 in which the fadR gene (SEQ ID NO:15 and SEQ ID NO: 16) was deleted and replaced by a $Km^R$ cassette was obtained from the Coli Genetic Stock Center (Yale University, New Haven, Conn.). This strain is part of the Keio collection constructed by Baba et al., 2006. Mol Syst Biol 2:1-11.

To generate a PCR product containing large regions of homology flanking the fadR::kan region the following primers were used:

```
FadR-Fwd1:
                                    (SEQ ID NO: 53)
5'-GCCATCGCCAGAGTGAAAATAAATTCCG
and FadR-Rev1:
                                    (SEQ ID NO: 54)
5'-GATTTCAAAGATGAGAGTTTTATCAGCCAGTTCCT.
```

This PCR reaction was carried out using the enzyme Phusion (New England BioLabs, Ipswich, Mass.) with an initial denaturation step at 98° C. for 30 sec, followed by 34 cycles of the steps: 98° C. for 10 sec; 56° C. for 20 sec and 72° C. for 1 min. This was followed by a final elongation step at 72° C. for 5 min.

After PCR, the resulting DNA fragment was gel-purified using a QIAquick Gel extraction kit (Qiagen Inc. Valencia, Calif.) following the manufacturer recommended protocol.

Strain W3110-fhuA was transformed with plasmid pKD46 (Coli Genetic Stock Center. Yale University, New Haven, Conn.) and cells were induced with arabinose and electrocompetent cells were prepared as described by Datsenko and Wanner (2000. PNAS 97: 6640-6645). The PCR product obtained above was transformed into the competent cells by electroporation. After 3 hr recovery in SOC media, plated on LB agar plates containing 30 micrograms/ml of Kanamycin. Plates were incubated overnight at 37° C. Resulting colonies were analyzed by colony-PCR using the following verification primers:

```
FadR-Fwd2:
                                    (SEQ ID NO: 55)
5' TTGGAGCGAATGCTTAACAGCAAACGGG
and FadR-Rev2:
                                    (SEQ ID NO: 56)
5' TGCGCCACTGCTGGAATCATGGCAGCGT.
```

A colony where the original fadR gene was replaced by the $Km^R$ cassette was purified and used for subsequent experiments. This strain was named W3110 ΔfhuA, ΔfadR::kan.

Example 8

Deletion of fabF in Strain W3110-ΔfhuA

A derivative of strain W3110-ΔfhuA was constructed with a deletion of the fabF gene (SEQ ID NO:13) and this strain was named W3110ΔfhuA, ΔfabF::kan. The method used was the same as described above with the following differences:

Strain JW1081-4 (Coli Genetic Stock Center. Yale University, New Haven, Conn.) was used as the source of the ΔfabF::kan mutation. Primers to generate the PCR product were: FabF-U3: 5' GAAAATTATCGGCGAACAGC (SEQ ID NO:57) and FabF-D3: 5' GTTAATTAAGAACATACCG-GCTCCTTAT (SEQ ID NO:58). Primers to verify the replacement of fabF with the $Km^R$ cassette were: FabF-U2: 5' CTTACATCACGGGTGAAACT (SEQ ID NO:59) and FabF-D2: 5' ATCTGCCTGCAACGACTCTT (SEQ ID NO:60).

Example 9

Construction of Deleted fabF (ΔfabF) and fadR (ΔfadR)

Construction of an *E. coli* strain containing both ☐fabF and fadR deletions were accomplished by removing the $Kan^R$ resistance marker present in the W3110ΔfhuA ☐ΔfadR::kan strain described above in Example 8. Plasmid pCP20 (Coli Genetic Stock Center. Yale University, New Haven, Conn.) is transformed into the strain. The kanamycin marker is removed following the protocol described by Datsenko and Wanner (2000. PNAS 97: 6640-6645). Following this protocol, the $Kan^R$ is eliminated and a scar with the FRT sequence is left in the chromosome (Datsenko and Wanner, 2000 PNAS 97: 6640-6645)) and (Baba et al., 2006 Mol Sys Biol 2:1-11) resulting in a $Kan^s$ strain. The fabF gene is then deleted following the procedure described in Example 8. The genotype of this strain is W3110ΔfhuA, ΔfadR::FRT, ΔfabF::kan.

Example 10

Production of Saturated Fatty Alcohols in *E. coli* Strains Described Above

The proportions of saturated and unsaturated fatty alcohols ("FOHs") produced by the strains described above were calculated after quantifying all the fatty alcohol species using GC-FID as described in US 2011/0000125SA1.

TABLE 1

% Fatty Alcohol Saturation with Over-expressed fabA.

| *E. coli* strain (W3110 ΔfhuA) + indicated plasmid (p) | % FOH saturation in the FOH composition |
|---|---|
| pCL3079 | 62.5 |
| pCL3079-fabA | 66.7 |
| pCL3079-RBS-fabA | 68.6 |
| pCL5019 | 57.9 |
| pCL5019-fabA | 62 |
| pCL5019-RBS-fabA | 63.6 |

TABLE 2

% Fatty Alcohol Saturation with Over-expressed fabZ.

| *E. coli* strain (W3110 ΔfhuA) + indicated plasmid (p) | % FOH saturation in the FOH composition |
|---|---|
| pCL3079 | 62.5 |
| pCL3079-fabZ | 87.2 |
| pCL5019 | 57.9 |
| pCL5019-fabZ | 84.0 |

TABLE 3

% Fatty Alcohol Saturation with Over-expressed fabI1.

| *E. coli* strain (W3110 ΔfhuA) + indicated plasmid (p) | % FOH saturation in the FOH composition |
|---|---|
| pCL5019 | 58.5 |
| pCL5019-fabI1 | 52.5 |
| pCL5019-fabI1-fabA | 61.0 |
| pCL5019-fabI1-RBSfabA | 65.4 |
| pCL5019-fabI1-fabZ | 91.6 |

TABLE 4

% Fatty Alcohol Saturation in a strain with deleted fabF::Km mutation

| *E. coli* strain (W3110ΔfhuA) | % FOH saturation in the FOH composition |
|---|---|
| pCL5019 | 57.5 |
| ΔfabF::Km/pCL5019 | 67.7 |

TABLE 5

% Fatty Alcohol Saturation in a strain with inactivated (Δ) fadR

| *E. coli* strain (W3110ΔfhuA) | % FOH saturation in the FOH composition |
|---|---|
| pCL5019 | 57.6 |
| pCL5019-ΔfadR | 69.8 |

Example 11

Construction of Plasmid pCK110900-FabI1-fabZ

FabI-1-fabZ genes were PCR amplified from pCL-5019-fabI-1-fabZ described in Example 5 above, with the following primers: 488: 5'-GATACGACCCGTAAACTTGCAAC-CATTTTTGGC-3' (SEQ ID NO: 61) and 8379_R CGCTTCTGCGTTCTGATTT-3' (SEQ ID NO: 62). The PCR reaction was carried out using the enzyme Phusion (New England BioLabs, Ipswich, Mass.) with an initial denaturation step at 98° C. for 30 sec, followed by 25 cycles of the steps: 98° C. for 10 sec; 56° C. for 20 sec and 72° C. for 40 sec. This was followed by a final elongation step at 72° C. for 5 min. The obtained PCR product was purified using a NucleoSpin Gel and PCR clean-up Kit (Clontech Laboratories Inc. Santa Clara Calif.), digested with NdeI and EcoRI enzymes, gel purified and ligated with pCK110900-I-Bla (described in U.S. Pat. No. 7,790,432) and digested with the same restriction endonucleases. The ligation reaction was incubated ON at 16° C. and then transformed into *E. coli* DH10B-T1 strain. 1 ml of SOC media was added to the transformed cells and cells were allowed to recover for 1 h at 37° C. with shaking at 250 rpm. Cells were plated on LB agar plates containing 30 microgram ml of chloramphenicol. Plates were then incubated overnight at 37° C. The presence of insert was verified by colony PCR with GoTaq GreenMix (Promega Corporation Madison, Wis.) following manufacturer recommendations. The obtained clone was sequence verified. The resulting plasmid was named pCK110900-fabI1-fabZ.

Example 12

Construction of pCDX11

The PTRC promoter present in pLS8379 described in Example 1, was replaced with a synthetic DNA fragment containing a PTRC variant where a symmetrical Lac operator [Sadler et al., 1983, PNAS. 80: 6785-6789] was introduced upstream of the −35 region of PTRC. This promoter was synthesized as an EcoRV-NcoI DNA fragment (GeneScript, Piscataway, N.J.) (SEQ ID NO: 63) and used to replace the EcoRV-NcoI region from pLS8379 previously cut with the same restriction enzymes.

```
SEQ ID NO: 63:
GATATCTCGGTAGTGGGATACGACGATACCGAAGACAGCTCA

TGTTATATCCCGCCGTTAACCACCATCAAACAGGATTTTCGC

CTGCTGGGGCAAACCAGCGTGGACCGCTTGCTGCAACTCTCT

CAGGGCCAGGCGGTGAAGGGCAATCAGCTGTTGCCCGTCTCA

CTGGTGAAAAGAAAAACCACCCTGGCGCCCAATACGCAAACC

GCCTCTCCCCGCGCGTTGGCCGATTCATTAATGCAGCTGGCA

CGACAGGTTTCCCGACTGGAAAGCGGGCAGTAATAATTTAAA

TTGGTTTGACAGCTTATCATCGACTGCACGGTGCACCAATGC

TTCTGGCGTCAGGCAGCCATCGGAAGCTGTGGTATGGCTGTG

CAGGTCGTAAATCACTGCATAATTCGTGTCGCTCAAGGCGCA

CTCCCGTTCTGGATAATGTTTTTTGCGCCGACATAATTGTGA
```

```
GCGCTCACAATTTCTGAAATGAGCTGTTGACAATTAATCATC

CGGCTCGTATAATGTGTGGAATTGTGAGCGGATAACAATTTC

ACACAGGAAACAGCGCCGCTGAGAAAAAGCGAAGCGGCACTG

CTCTTTAACAATTTATCAGACAATCTGTGTGGGCACTCGACC

GGAATTATCGATTAACTTTATTATTAAAAATTAAAGGAGGAA

TAAACCATGG
```

A ligation reaction containing the two DNA fragments was incubated overnight at 16° C. and then transformed into *E. coli* Top10 electrocompetent cells (Invitrogen, Carlsbad, Calif.) following the manufacturer's protocols. Cells were plated on LB agar plates containing 100 ug/ml of Spectinomycin. Plates were incubated overnight at 37° C. Obtained clones were sequence verified. The resulting plasmid was named pCDX11.

Example 13

Chromosomal Integration fabI1 and fabZ (1) The entire lacI structural gene and lacZ promoter were deleted from *E. coli* strain W3110K using lambda RED-mediated homologous recombination. Cells were transformed with plasmid pSIM5 (Gene. 2006 Sep. 1; 379:109-15). A single colony was grown to log-phase at 32° C., induced at 42° C. for 15 minutes and electrocompetent cells were prepared as described by Datta, Costantino, and Court (2006) Gene 379: 109-115. Competent cells were transformed with 500 ng of the synthetic oligonucleotide lac_del_F:
5'-G*G*A*A*GGCGAAGCGGCATGCATTTACGTTGA CACCATCGAATT CACTGGCCGTCGTTTTA-CAACGTCGTGACTGGGAAAAC-3' (SEQ ID NO: 102), wherein *=phosphorothioate bond modifications incorporated into the synthetic oligonucleotide (IDT Technologies, Coralville, Iowa).

After transformation, cells were recovered at 32° C. for five hours, plated on LB agar plates supplemented with 50 ug/ml of X-Gal (Promega, Madison, Wis.), and incubated overnight at 37° C. A white colony from the plate was sequence verified to have a deletion of the lad gene and lacZ promoter and was named strain W3110K-lac-del. Next a double-stranded DNA cassette for inserting the lacIq and pCDX11 sequences into the strain above was generated in two steps:

(a) A dsDNA cassette was PCR amplified from the plasmid pCDX11-5019 described in Example 2, using the following primers: lac-intro_F: 5'-CGCAGGCTATTCTG-GTGGCCGGAAGGCGAAGCG GCATGCATTTA-3' (SEQ ID NO: 64) and lac-intro_R2: 5'-AACGACGGCCA-GTGAATCCGTAA TCATGGTCATGGTTTATTCCTC-CTTTAATTTTTAATA-3' (SEQ ID NO: 65). The PCR reaction was carried out using Phusion DNA polymerase (New England BioLabs, Ipswich, Mass.) with an initial denaturation step at 98° C. for 30 sec, followed by 30 cycles of the steps: 98° C. for 5 sec; 63° C. for 20 sec and 72° C. for 30 sec. A final elongation step was conducted at 72° C. for 5 min. After the PCR reaction, the PCR products were purified through a purification column and eluted with water.

(b) Homology to lacZ was added to the cassette described in part (a) using the following primers: lac-intro_F: 5'-CGCAGGCTATTCTGGTGGCCGGAAGGCGAAGCG-GCATGCATTTA-3' (SEQ ID NO: 66) and lac-intro_R1: 5'-AGTTGGGTAACGCCAGGGTTTTCCCAGTCAC-GACGTTGTAAAAC GA CGGCCAGTGAATCC-3' (SEQ ID NO:67). The second PCR was carried out with the same conditions as in part (a). After the PCR reaction, the PCR product was purified through a PCR purification column and eluted with water. This product was named lacIq-PCDX11 cassette.

Strain W3110K-lac-del (see above) was transformed with the plasmid pSIM5. Recombination proficient cells were generated as described above, and the cells were transformed with 500 ng of the lacIq-pCDX11 cassette. After recovery at 32° C. for five hours, the cells were plated on M9 minimal media agar (Difco™ M9 Minimal Salts, Cat. No. 248510) supplemented with MgSO₄, CaCl₂, and 0.5% lactose. After several days, lactose proficient colonies emerged on the minimal media plates. One colony was purified by streaking to single colonies and a clone was confirmed to have the lacIq-pCDX11 insertion by sequence verification. The purified clone was named W3110K-lacIq-pCDX11-lacZ.

(2) A fabI-1-fabZ-cat cassette was obtained by PCR using the plasmid pCK110900-fabI-1-fabZ plasmid described in Example 11 above. In this plasmid, the chloramphenicol resistance marker (cat) is located downstream of the fabI1-fabZ genes. The PCR reaction was carried out using the primers and conditions listed below. Nucleotides in italics are homologous to targeted sequences in genomic DNA, while those in underline are homologous to amplification of cassettes.

```
124.ptrc60.fabI-1.F
                                  (SEQ ID NO: 68)
5'-GGGCACTCGACCGGAATTATCGATTAACTTTATTATTAAAAATTA AAGGAGGAATAAACCATGACCGCAGGACTGATGGC
and 125.Y550-CAT.R
                                  (SEQ ID NO: 69)
3'-CAAACTGATTATTGATGGTGAACATGATGCCGACAATCGAGG

CACACAGCGCCCAGAAAGGACAAGTTTTGGTGA
```

The PCR reaction was carried out using the Phusion polymerase (New England BioLabs, Ipswich, Mass.) with an initial denaturation step at 98° C. for 30 sec, followed by 25 cycles of the steps: 98° C. for 10 sec; 60° C. for 20 sec and 72° C. for 15 sec/kb. The final extension step was conducted at 72° C. for 5 min. After PCR, the resulting DNA fragment was digested with DpnI and purified by gel-extraction using a Zymoclean Gel DNA Recovery Kit (Zymo Research, Irvine, Calif.) following the manufacturer recommended protocol. Strain W3110ΔhuA-lacIq-CDX11p-lacZ described in above was transformed with plasmid pKD46 (*E. coli* Genetic Stock Center. Yale University, New Haven, Conn.) and cells were induced with arabinose as described by Datsenko and Wanner (PNAS 97: 6640-6645. 2000). Electrocompetent cells were prepared by repeated pelleting and resuspension in cold sterile dH₂O at least twice, concentrated 20-fold into 50 ul. The PCR product obtained above was electroporated with a BioRad GenePulser (BioRad, Hercules, Calif.) using a 1 mm gap cuvette at 1.8 kV, 25 μF and 200Ω. Electroporated cells were immediately added to 1 ml SOC and incubated for 2 hours at 37° C. prior to plating on LB agar plates containing 30 μg/ml chlroamphenicol. Colonies were streaked to isolate single colonies. Insertion of the fabI-1-fabZ cassette was verified by colony PCR and by sequencing the PCR product obtained with the following primer set: 138. lacY lacI-q.ver.F1 5'-GGCTGGGATCAGGAGGAGAAG-3' (SEQ ID NO:70) and 137. lacY949.R 5'-AATGATCAGTGGCG-CAAAGAACATA-3' (SEQ ID NO: 71). The colony confirmed to have the fabI1 and fabZ genes inserted was named W3110ΔfhuA::pCDX11-fabI1-fabZ-cat.

Example 14

Generating W3110K-pCDX11-fabI-1-fabZ-cat-frt

A further version of the fabI1-fabZ-cat cassette was constructed. The cat gene was looped out using the Flp-recombinase as described by Datsenko and Wanner (PNAS 97: 6640-6645, (2000).

Construction and integration was as follows:

The fabI-1-fabZ operon under the pCDX11 promoter was amplified from the genomic DNA of W3110ΔfhuA::pCDX11-fabI1-fabZ-cat using the following primers: 156. Proms-F1 5'-CCAGC GTGGACCGCTTGCTGCAAC-3' (SEQ ID NO: 72) and 170. fabZtm99 R 5'-CCCGGAGT-GATCTTATTTC-3' (SEQ ID NO: 73). The chloramphenicol resistant cassette (cat-frt) was amplified from pKD32 plasmid (Coli Genetic Stock Center. Yale University, New Haven, Conn.) using the following primers: 171. Z-cat.frt.F 5'-GAAATAAGATCACTCCGGGATTCCGGGGATCCGT CGACC-3' (SEQ ID NO: 103 and 172.cat.frt-Y551.R 5'-CAAACTGATTATTGATGGTGA ACATGATGCCGA-CAATCGAGGCACACAGCGCCCAGTGTAGGCTG-GAGCTGCTTC-3' (SEQ ID NO: 104).

The PCR reactions were carried out using the Phusion polymerase (New England BioLabs, Ipswich, Mass.) with an initial denaturation step at 98° C. for 30 sec, followed by 25 cycles of the steps: 98° C. for 10 sec; 60° C. for 20 sec and 72° C. for 15 sec/kb. A final extension step was conducted at 72° C. for 5 min. The PCR amplified fragments were digested with DpnI, and purified by gel-extraction using a Zymoclean Gel DNA Recovery Kit (Zymo Research, Irvine, Calif.) following the manufacturer recommended protocol, and then combined using SOE PCR (Splicing by Overlap Extension PCR, Warrens et al., Gene 1997, 186(1):29-35) standard protocol to obtain full-length of cdx11p-fabI-1-fabZ-cat-frt cassette. The PCR product was purified using gel-extraction using a Zymoclean Gel DNA recovery Kit.

In the final step, the cassette was inserted in the chromosome of 2 different strains; W3110K (E. coli Stock Center strain #7167, New Haven, Conn.) and W3110ΔfhuA by first transforming plasmid pSIM6 (Datta, Costantino, and Court (2006) Gene 379: 109-115). A purified colony from this transformation was used to prepare competent cells by growing the cells to log-phase at 30° C. reaching OD600 of 0.6 and then induced at 42° C. for 15 minutes. Cells were immediately chilled on ice and electrocompetent cells were prepared by repeated pelleting and resuspension in cold sterile dH$_2$O at least twice, concentrated 20-fold into 50 ul. The PCR cassette obtained above was electroporated with a BioRad GenePulser (BioRad, Hercules, Calif.) using a 1 mm gap cuvette at 1.8 kV, 25 μF and 200Ω. Electroporated cells were immediately added to 1 ml SOC and incubated for 2 hours at 37° C. prior to plating on LB agar plates containing 30 μg/ml chlroamphenicol. Colonies were streaked to isolate single colonies, and the insertion of PCDX11-fabI1-fabZ-cat-frt cassette was verified by sequencing the PCR product obtained with the following primer sets: 138. lacY lacI-q.ver.F1 GGCTGGGATCAGGA GGAGAAG (SEQ ID NO: 74); 143. FabI-1.Rev TCAGCAGGCTACCACGTTCG (SEQ ID NO: 75) and 141. FabI-1Fwd TGCGGAACTG-GCGTTTTCTTACC (SEQ ID NO: 76) and 183.C3. Rev GTAG AAACTGCCGGAAATCG (SEQ ID NO:77).

The colony confirmed to have the PCDX11-fabI1-fabZ-cat-frt insertion was named W3110K-PCDX11-fabI1-fabZ-cat-frt and W3110ΔfhuA-PCDX11-fabI1-fabZ-cat-frt Example 15

Chromosomal Integration of fabI1 and fabZ Genes

To express the fabI1 and fabZ constitutively in the chromosome of the E. coli W3110K strain (E. coli Stock Center strain #7167, New Haven, Conn.), a synthetic promoter (see below) was used. These 2 genes were amplified by PCR using 2 primers with the following relevant properties: Primer oJN-1.-F TCTTTCATACAATGACATAT-TAAAATATCAGCAAGAATTCCAAAGGGTTTTTT-TAGGCC TTTGACAGCTAGCTCAGTCCTAGG-TATACTGCTAGCATACTAGAGGCCAGCCTGGCCATA AGGAGATATACAT (SEQ ID NO: 78) Nucleotides 1-44 provide a region of homology with the E. coli pseudogene yhiS-2. Nucleotides 45-107 encode a synthetic promoter sequence and the first 12 bases of the mRNA. Nucleotides 108-132 provide a region of homology with plasmid pCK110900-fabI-1-fabZ (see example 11 above) and allow the amplification of the 5'-end of the fabI1-fabZ genes. Primer pCK-chlor_R. TTGAAATACTTCGAATTGATAT-TCAGACATTTCTGCCCATGTTTGCTGAAA GGA-CAAGTTTTGGTGACTG (SEQ ID NO: 79). Nucleotides 1-45 provide a region of homology with the E. coli pseudogene yhiS-2. Nucleotides 46-70 provide a region of homology with plasmid pCK110900-fabI-1-fabZ (see Example 11 above) and allow the amplification of the 3'-end of the cat gene present in the plasmid. PCR reaction composition: H$_2$O (33.3 uL); 5x herculase II reaction buffer (10 uL); dNTPmix (10 mM) (1 uL); DNA template 1 uL); FP (1.25 uL); RP (1.25 uL); Herculase II Phusion (0.8 uL); DSMO (1.5 uL) for total volume of 50 uL. PCR Reaction conditions:

| Segment | # of Cycles | Temperature | Duration |
|---------|-------------|-------------|----------|
| 1 | 1 | 95 | 2 min |
| 2 | 10 | 95 | 20 sec |
|   |   | 68 | 20 sec |
|   |   | 68 | 2 min |
| 3 | 20 | 95 | 20 sec |
|   |   | 62 | 20 sec |
|   |   | 68 | 2 min |
| 4 | 1 | 68 | 8 min |

After PCR, the resulting DNA fragment was digested with DpnI and purified by gel-extraction using a Zymoclean Gel DNA Recovery Kit (Zymo Research, Irvine, Calif.) following the manufacturer recommended protocol. The PCR product was used as an integration cassette. For this purpose, strain W3110K was first transformed with plasmid pSIM6 and competent cells were prepared as described by Datta et al., [Gene 379: 109-115 (2006)]. Briefly, cells were grown to log-phase at 30° C. reaching OD600 of 0.6 and then induced at 42° C. for 15 minutes. Cells were then immediately chilled on ice and electrocompetent cells were prepared by repeated pelleting and resuspension in cold sterile dH$_2$O at least twice. After the final wash, cells were concentrated 20-fold by resuspending them in the appropriate dH$_2$O volume. 50 μl aliquots of this concentrate were used for electroporation. The PCR cassette obtained above was electroporated with a BioRad GenePulser (BioRad, Hercules, Calif.) using a 1 mm gap cuvette at 1.8 kV, 25 µF and 200Ω. Electroporated cells were immediately added to 1 ml SOC and incubated for 2 hours at 37° C. prior to plating on LB agar plates containing 30 µg/ml chlroamphenicol. Colonies were streaked to isolate single colonies. The insertion of Pconst-fabI-1-fabZ-cat cassette was verified by colony PCR and by sequencing the PCR product obtained with the following primer set: ins-yhiS_seqF: ACCAGCCTTGGGG-TAAAACG (SEQ ID NO: 80) and ins-yhiS_seqR: TTTTGGGTTAAGC GTCTCGT (SEQ ID NO: 81). The strain confirmed to have PconstI-fabI1-fabZ gene insertion was named W3110K-Pconst-fabI1-fabZ-cat.

Example 16

Construction of pCDX11-8087-fabI-1-RcfabZ

To determine the effect of overexpressing the fabZ gene from *Rhodobacter capsulatus* on fatty alcohol production in *E. coli* which also included a polynucleotide encoding the FAR-V3 (SEQ ID NO: 28), plasmid pCDX11-8087-fabI1-RcfabZ was constructed as described below.

A. The cloning vector pCDX11-8087-MCS was linearized by digestion with SalI and Bsu36I restriction enzymes (New England BioLabs, Ipswich, Mass.), and then gel extracted using Zymoclean Gel DNA Recovery Kit (Zymo Research, Irvine, Calif.) following the manufacturer recommended protocol.

B. The fabI1 gene was amplified from plasmid pCDX11-8087-fabI1-fabZ using the following primers: 237.N-link-fabI-1.F CTGACGATAAAACCGCCTAAGTCGACATAAGGA-GATATACAT (SEQ ID NO: 82) and 238.C-link-fabI-1.R CATGATACTCTTCCTAAACTCAAGCTTATTAGTC (SEQ ID NO: 83).

C. The protein sequence of the fabZ gene from *Rhodobacter capsulatus* (GenBank:ADE85379, also SEQ ID NO: 26) was utilized to design an *E. coli* codon optimized gene. To facilitate further manipulations of the gene, other sequences were included upstream and downstream of the structural fabZ gene. The extra downstream sequences comprised a multicloning site (MCS), a transcriptional terminator sequence, and 15 bp of homologous sequence to pCDX11-8087. The extra sequence upstream of the gene contained a region of homology to fabI1. The sequence of the synthetic DNA is illustrated as SEQ ID NO:25 and was synthesized by GenScript (Piscataway, N.J.), who provided it cloned into pUC57 and named pUC57-RcfabZ. The fabZ gene was amplified from plasmid pUC57-RcfabZ using the following primers: 239.I-1-RcZ.F TCGGCATGAAAGCG-GTTGATG (SEQ ID NO: 84) and 241.Bsu36I.21.R GAGAAAATACCGCATCAGGCG (SEQ ID NO: 85).

The PCR reactions was carried out using the Phusion polymerase (New England BioLabs, Ipswich, Mass.) with an initial denaturation step at 98° C. for 30 sec, followed by 25 cycles of the steps: 98° C. for 10 sec; 60° C. for 20 sec and 72° C. for 15 sec/kb. This was followed by a final extension step at 72° C. for 5 min. The two PCR amplified fragments described in sections B and C above, were digested with DpnI, and purified by gel-extraction using a Zymoclean Gel DNA Recovery Kit, and then combined using SOE PCR (Splicing by Overlap Extension PCR, Warrens et al., Gene 1997, 186(1):29-35) standard protocol using the primers 237.N-link-fabI-1.F and 241.Bsu36I.21.R shown above. These primers contain 20 bp of homologous sequence to the plasmid pCDX11-8087. The PCR product was purified using gel-extraction using a Zymoclean Gel DNA recovery Kit and cloned into linearized pCDX11-8087 described in section A above, using the In-Fusion Kit (Clontech Laboratories Inc. Mountain View, Calif.) according to manufacturer's protocol. In-Fusion reaction mixture was transformed into DH10B-T1 (Invitrogen, CA) cells using electroporation method described in Example 15. Transformed cells were plated on LB agar agar containing 100 µg/ml of spectinomycin. Plates were incubated overnight at 37° C. Resulting plasmid was sequence-verified and named pCDX11-8087-fabI1-RcfabZ.

Example 17

Construction of pCDX11-8087-fabI1-fabZ

Plasmid pCDX11-8087-FabI-1-FabZ overexpressing the fabI1-fabZ genes as part of an operon with the gene encoding the FAR-V3 under control of the CDX11 promoter was constructed as described below.

First, the *E. coli* codon-optimized FabI-1 gene from *Rhodobacter sphaeroides* SB103 and the native *E. coli* fabZ gene were PCR amplified from plasmid pCL-5019-FabI-1-FabZ (see Example 5), using primers 488_F and 8379_R: 488_F GATACGACCCGTAAACTTGCAAC-CATTTTTGGC (SEQ ID NO: 86) and 8379_R CGCTTCT-GCGTTCTGATTT (SEQ ID NO: 87).

The PCR reaction was carried out using Phusion DNA polymerase (New England BioLabs, Ipswich, Mass.) with an initial denaturation step at 98° C. for 30 sec, followed by 30 cycles of the steps: 98° C. for 5 sec; 63° C. for 20 sec and 72° C. for 45 sec. A final elongation step was conducted at 72° C. for 5 min. The PCR products were purified through a PCR purification column and eluted with water.

The FabI-1-FabZ PCR product and the plasmid pCDX11-8087-MCS were digested with the restriction enzymes SalI and AatII (Fermentas, Glen Burnie, Md.) and the resulting products were ligated using Quick T4 DNA Ligase (New England BioLabs, Ipswich, Mass.) following manufacturer recommendations. The reaction was transformed into *E. coli* Top10 electrocompetent cells (Invitrogen, Carlsbad, Calif.) following the manufacturer's protocols. Cells were plated on LB agar plates containing 100 micrograms/ml of spectinomycin and were incubated overnight at 37° C. Obtained clones were sequence verified. This plasmid was named pCDX11-8087-fabI1-fabZ.

Example 19

Construction of pCDX11-8087-fabI1

Plasmid pCDX11-8087-fabI1 was constructed by subcloning the fabI1 gene downstream of the FAR V3 present in plasmid pCDX11-8087-MCS. Plasmid pCDX11-8087-MCS was linearized by digestion with SalI and Bsu36I restriction enzymes (New England BioLabs, Ipswich, Mass.), and then gel extracted using Zymoclean Gel DNA Recovery Kit (Zymo Research, Irvine, Calif.) following the manufacturer recommended protocol.

The fabI1 gene was PCR amplified from pCDX11-8087-fabI1-fabZ described in example 18, using the following primers: 249.fabI-1.F CTGACGATAAAACCGC-CTAAGTCGACAT AAGGAGATATACATATGACCG (SEQ ID NO: 88) and 250. fabI-1-3HA.R AAACGAAT-TCATAGACGTCAAGCTTATTAGTCTTTACGACCCGT-GAC (SEQ ID NO: 89).

For the In-Fusion reaction, the downstream sequence of fabI1 requires a homology region to the cloning vector pCDX11-8087-MCS. The nucleotide sequence for the homology region of the fabI1 gene was obtained from the downstream sequence of RcfabZ present in plasmid pUC57-RcfabZ (see, Example 16 above) and modified using the following primers: 247.I-1-HAEP.F CACGGGTCG-TAAAGACT AATAAGCTTGACGTCTATGAATTCGTT-TAAACGCCAGGC (SEQ ID NO: 90) and 241.Bsu36I.21.R GAGAAAATACCGCATCAGGCG (SEQ ID NO: 91).

The PCR reaction was carried out using the Phusion polymerase (New England BioLabs, Ipswich, Mass.) with an initial denaturation step at 98° C. for 30 sec, followed by 25 cycles of the steps: 98° C. for 10 sec; 60° C. for 20 sec and 72° C. for 15 sec/kb. This was followed by a final extension step at 72° C. for 5 min. These two PCR amplified fragments were digested with DpnI, and purified by gel-extraction using a Zymoclean Gel DNA Recovery Kit, and then combined using SOE PCR (Splicing by Overlap Extension PCR, Warrens et al., Gene 1997, 186(1):29-35) standard protocol using the primers 249.fabI-1.fw and 241.Bsu36I.21.R shown above. These primers contain 20 bp of homologous sequence to the plasmid pCDX11-8087. The PCR product was purified using gel-extraction using a Zymoclean Gel DNA recovery Kit and cloned into linearized pCDX11-8087-MCS (described above) using the In-Fusion Kit (Clontech Laboratories Inc. Mountain View, Calif.) according to manufacturer's protocol. In-Fusion reaction mixture was transformed into DH10B-T1 (Invitrogen, CA) cells using electroporation method shown in example 2. Transformed cells were plated on LB agar agar containing 100 µg/ml of spectinomycin. Plates were incubated overnight at 37° C. The resulting plasmid was sequence-verified and named pCDX11-8087-fabI1.

Example 18

Construction of pCDX11-8087-RcfabZ

The cloning vector pCDX11-8087-MCS was linearized by digestion with SalI and Bsu36I restriction enzymes (New England BioLabs, Ipswich, Mass.), and then gel extracted using Zymoclean Gel DNA Recovery Kit (Zymo Research, Irvine, Calif.) following the manufacturer recommended protocol. The RcfabZ gene was amplified from plasmid pUC57-RcfabZ described in Example 16 using the following primers containing 20 bp of homologous sequence to the cloning vector pCDX11-8087: 248. Far-RcZ.fw GACGA-TAAAACCGCCTAATAAGCTTGAGTTTAGGAAGAG-TATC ATGTCTG (SEQ ID NO:92) and 241.Bsu36I.21.R GAGAAAATACCGCATCAGGCG (SEQ ID NO: 93).

This PCR reaction was carried out using the Phusion polymerase (New England BioLabs, Ipswich, Mass.) with an initial denaturation step at 98° C. for 30 sec, followed by 25 cycles of the steps: 98° C. for 10 sec; 60° C. for 20 sec and 72° C. for 15 sec/kb. This was followed by a final elongation step at 72° C. for 5 min. After PCR, the resulting DNA fragment was digested with DpnI and purified by gel-extraction using a Zymoclean Gel DNA Recovery Kit. The RcfabZ gene fragment was cloned into linearized pCDX11-8087-MCS using the In-Fusion Kit (Clontech Laboratories Inc. Mountain View, Calif.) according to manufacturer's protocol. In-Fusion reaction mixture was transformed into DH10B-T1 (Invitrogen, CA) cells using electroporation method shown in example 2. Transformed cells were plated on LB agar agar containing 100 µg/ml of spectinomycin. Plates were incubated overnight at 37° C. Resulting plasmid was sequence-verified and named pCDX11-8087-RcfabZ.

Example 19

Construction of pCDX11-8087-MCS Plasmid

The plasmid pCDX11-FAR-MCS comprising the polynucleotide encoding FAR-V3 was constructed as follows: A DNA fragment containing the FAR-V3 gene was PCR amplified using the primers: 8087_NcoI_F 5'-TAAAC-CATGGCGACTCAACAACAGAACA (SEQ ID NO: 94) and 8087_SalI_R 5'-CTATGTCGACTTAGGCGGTTT-TATCGTCAGTATCA (SEQ ID NO: 95). The PCR reaction was carried out using the Phusion polymerase (New England BioLabs, Ipswich, Mass.) with an initial denaturation step at 98° C. for 30 sec, followed by 25 cycles of the steps: 98° C. for 10 sec; 60° C. for 20 sec and 72° C. for 15 sec/kb. This was followed by a final extension step at 72° C. for 5 min. After PCR, the resulting DNA fragment was purified by gel-extraction using a Zymoclean Gel DNA Recovery Kit. As the restriction enzyme sites NcoI and SalI were incorporated into the primers 8087_NcoI_F and 8087_SalI_R respectively, this allowed the ligation of this PCR product into pCDX11 digested with NcoI and SalI restriction enzymes accordingly the manufacturer conditions (New England BioLabs, Ipswich, Mass.). Ligation reactions were incubated overnight at 16° C. and then transformed into E. coli TOP10 chemically competent cells (Invitrogen, Carlsbad, Calif.) using standard techniques. Cells were plated on LB agar plates containing 100 ug/ml of Spectinomycin and incubated overnight at 37° C. Obtained clones were sequence verified. A clone with the correct sequence was designated pCDX11-8087-MCS.

Example 20

Construction of pCDX11-8087-BTE1-fadD

To produce fatty alcohols from acyl-CoA intermediates instead of acyl-ACP intermediates, a plasmid to overexpress FAR, the Bay tree thioesterase (BTE) and the E. coli acyl-CoA synthase gene (FadD) was constructed as follows.

The polynucleotide (SEQ ID NO: 27) encoding variant FAR-V3 (SEQ ID NO: 28) was PCR amplified using pCDX11-8087-MCS using the following primers:

```
5' cloning site + RBS1:FAR 8087
                                        (SEQ ID NO: 96)
5' CCGGAATTATCGATTAACTTTATTATTAAAAATT AAAGGAGGAATAAACCATGGCGACTCAACAACAGAAC
and FAR 8087:RBS-ptrc
                                        (SEQ ID NO: 97)
3' TAAGGTCATGGTTTATTCCTCCTTGTCGACTTAGGCG

GTTTTATCGTCAGTATC.
```

The polynucleotide encoding the BTE thioesterase (SEQ ID NO: 21) was synthesized by GenScript (Piscataway, N.J.), and the synthesized gene was amplified by PCR using the following primers:

```
RBS-ptrc:CaBayTES1
                                       (SEQ ID NO: 98)
5' ACCGCCTAAGTCGACAAGGAGGAATAAACCATGACCTTA GAGTGGAAACCAAAA
and CaBayTES1:RBS-pCK
                                       (SEQ ID NO: 99)
3' GCCAAACCTTCTTCATATGTATATCTCCTTTTATACCCG

CGGCTCGG.
```

The native *E. coli* fadD gene (SEQ ID NO: 19) was PCR amplified from *E. coli* genomic DNA using the following primers:

```
RBS-pCK:fadD 5':
                                       (SEQ ID NO: 100)
CGAGCCGCGGGTATAAAAGGAGATATACATATGAAGAAGGTT TGGCTTAACCG
and fadD:3' cloning site 3':
                                       (SEQ ID NO: 101)
TTAAGAAGCTTCCGAGTAAGTTCTAGATCTTCATTAGGCTTT

ATTGTCCACTTTG.
```

PCR amplifications were performed with Herculase II (Agilent Technologies, Santa Clara, Calif.) following manufacturer's protocol with at 60° C. annealing temp. These three PCR amplified fragments were combined using SOE PCR (splicing by overlap extension PCR) standard protocol (see, Warrens et al., 1997 Gene 186(1):29) using primers 5' cloning site+RBS1:FAR 8087 5' and fadD:3' cloning site 3' mentioned above. The final PCR product was inserted into linearized pCDX11 plasmid with ClaI and BglII restriction enzymes from Fermentas (Thermo Scientific, Glen Burnie, Md.), ligated overnight at 16° C. with T4 DNA ligase per manufacturer's protocol (NEB, Ipswich, Mass.), and transformed into electrocompetent W3110 ΔfhuA using standard molecular biology methods (Dower et al., 1988 NAR 16:6127-6145). Cells were plated on LB agar plates containing 100 ug/ml of spectinomycin and plates were incubated overnight at 37° C. Clones were sequence-verified and the plasmid named pCDX11-8087-BTE-fadD.

Example 21

Fatty Alcohol Production from *E. coli* Strains Described Above

The amount of fatty alcohols and saturation level by the strains described above were calculated after quantifying all the fatty alcohols species using GC_ED as described in US2011/0000125SA1.

TABLE 6

Fatty alcohol levels and % saturation produced in *E. coli* W3110ΔfhuA strains with fabI1-fabZ overexpressed with an inducible promoter integrated in the chromosome.

| Plasmid | g/L FOH | % Saturation |
|---|---|---|
| pCDX11-5019 | 2.35 | 63.5 |
| pCDX11-fabI1-fabZ-cat/pCDX5019 | 2.77 | 76.7 |

TABLE 7

Fatty alcohol levels and % saturation produced in *E. coli* W3110ΔfhuA strains with fabI1-fabZ overexpressed with an inducible promoter integrated in the chromosome.

| Plasmids | g/L FOH | % Saturation |
|---|---|---|
| pCDX115019-BTE1-fadD | 1.4 | 67.4 |
| pCDX117076-BTE1-fadD | 3.33 | 82.5 |
| pCDX11-fabI1-fabZ-cat-frt/pCDX5019-BTE1-fadD | 3.18 | 66.7 |
| pCDX11-fabI1-fabZ-cat-frt/pCDX7076-BTE1-fadD | 4.58 | 83.5 |

Plasmid pCDX11-7076-BTE1-fadD was constructed in the same manner as pCDX11-5019 and pCDX11-8086-BTE1-fadD, but with a FAR variant having 2 amino acid residues different than FAR-V3.

TABLE 8

Fatty alcohol levels and % saturation produced in *E. coli* W3110K strains with fabI1-fabZ overexpressed with a plasmid.

| Plasmids | g/L FOH | % Saturation |
|---|---|---|
| pCDX11-8087-BTE-fadD | 3.8 | 53.5 |
| pCDX11-fabI1-fabZ-cat-frt/pCDX8087-BTE-fadD | 4.25 | 70.0 |

TABLE 9

Fatty alcohol levels and % saturation produced in *E. coli* W3110K strains with fabI1-fabZ overexpressed with a constitutive promoter integrated in the chromosome.

| Plasmids | g/L FOH | % Saturation |
|---|---|---|
| pCDX11-8087-BTE1-fadD | 3.8 | 53.5 |
| Pconst-fabI1-fabZ-cat/pCDX8087-BTE1-fadD | 3.6 | 67.7 |

TABLE 10

% saturated fatty alcohols in *E. coli* W3110 ΔfhuA strains overexpressing the *Rhodobacter capsulatus* fabI1 and/or fabZ genes.

| Plasmids | % Saturation |
|---|---|
| pCDX11-8087-fabI1 | 59 |
| pCDX11-8087-RcFabZ | 88 |
| pCDX11-8087-fabI1-FabZ | 82 |
| pCDX11-8087-fabI1-RcFabZ | 90 |

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. An engineered bacterial microorganism comprising at least one polynucleotide encoding at least one heterologous fatty acyl-ACP reductase enzyme (FAR), wherein said FAR comprises an amino acid sequence having at least 80% sequence identity to SEQ ID NO:28 and has fatty alcohol forming acyl-CoA reductase activity, and a first recombinant polynucleotide encoding a FabZ enzyme, wherein said FabZ enzyme comprises the amino acid sequence set forth in SEQ ID NO:8, wherein the engineered bacterial microorganism produces a fatty alcohol composition comprising C10 to C18 fatty alcohols.

2. The engineered bacterial microorganism according to claim 1 further comprising a second recombinant polynucleotide encoding a FabI enzyme.

3. The engineered bacterial microorganism of claim 2, wherein the FabI enzyme comprises an amino acid sequence comprising at least 80% sequence identity to SEQ ID NO:12, and has enoyl ACP-reductase activity.

4. An engineered bacterial microorganism comprising a polynucleotide encoding i) a heterologous fatty acyl-ACP reductase enzyme having at least 95% sequence identity to SEQ ID NO: 28 and fatty alcohol forming acyl-CoA reductase activity, ii) a first recombinant polynucleotide sequence encoding a FabZ enzyme having at least 95% sequence identity to SEQ ID NO:8 and dehydratase activity, and iii) a second recombinant polynucleotide sequence encoding a FabI enzyme having at least 95% sequence identity to SEQ ID NO: 12 and enoyl-ACP reductase activity, wherein the engineered bacterial microorganism is capable of producing a fatty alcohol composition.

5. A method of producing a fatty alcohol composition comprising:
a) providing the engineered microorganism of claim 1;
b) culturing the engineered microorganism in a culture medium under suitable culture conditions for the production of fatty alcohols or derivatives thereof;
c) allowing production of the fatty alcohols or derivatives thereof; and
d) optionally recovering the produced fatty alcohols or derivative thereof from the engineered microorganism.

6. The method according to claim 5, wherein the fatty alcohol composition comprises at least 60% of C12:0, C14:0, C16:0 and C18:0 fatty alcohols.

7. The method according to claim 5, wherein the % of saturated fatty alcohols in the fatty alcohol composition is at least 60%.

8. The method according to claim 5, wherein the culturing is at a temperature of about 25° C. to about 45° C.

9. The method according to claim 5, wherein at least 2 g/L of fatty alcohols are produced.

10. A method for producing a fatty alcohol composition comprising at least 60% saturated fatty alcohols comprising:
a) providing the engineered bacterial microorganisms of claim 1;
b) culturing the engineered microorganism in a culture medium under suitable culture conditions for the production of fatty alcohols;
c) allowing production of the fatty alcohols; and
d) optionally recovering the produced fatty alcohols.

11. The method according to claim 10, wherein the fatty alcohol composition comprises at least 60% of saturated C12, C14, C16 and/or C18 fatty alcohols.

12. The method according to claim 10, wherein at least 2 g/L of fatty alcohols are produced.

* * * * *